United States Patent
Bertoni et al.

(10) Patent No.: US 10,077,260 B2
(45) Date of Patent: Sep. 18, 2018

(54) READ-THROUGH COMPOUND PRODRUGS SUPPRESSING PREMATURE NONSENSE MUTATIONS

(71) Applicant: The Regents of the University of California, Oakland, CA (US)

(72) Inventors: Carmen Bertoni, Los Angeles, CA (US); Jasbir Singh, Naperville, IL (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/112,100

(22) PCT Filed: Jan. 16, 2015

(86) PCT No.: PCT/US2015/011842
§ 371 (c)(1),
(2) Date: Jul. 15, 2016

(87) PCT Pub. No.: WO2015/109248
PCT Pub. Date: Jul. 23, 2015

(65) Prior Publication Data
US 2016/0333003 A1    Nov. 17, 2016

Related U.S. Application Data

(60) Provisional application No. 61/928,334, filed on Jan. 16, 2014.

(51) Int. Cl.
*A61K 31/506*    (2006.01)
*C07D 417/06*    (2006.01)
*C07D 417/14*    (2006.01)

(52) U.S. Cl.
CPC ......... *C07D 417/06* (2013.01); *C07D 417/14* (2013.01)

(58) Field of Classification Search
CPC .............................. C07D 417/06; C07D 417/14
See application file for complete search history.

(56) References Cited

U.S. PATENT DOCUMENTS 9,255,088 B2 * 2/2016 Gatti .................... C07D 413/06

FOREIGN PATENT DOCUMENTS

KR    2012035684 A *    4/2012
WO    2012021707 A2    2/2012
WO    WO-2012021707 A2 *    2/2012    .......... C07D 417/06

OTHER PUBLICATIONS

CAS Regestry No. 340229-15-4 (2001).*
CAS Registry No. 878230-77-4 (2006).*
C. Fan et al., 18 Bioorganic & Medicinal Chemistry, 2141-2151 (2010).*
The Penguin Dictionary of Science (M.G. Clugston ed., 2009).*
CAS Abstract KR 2012035684 (2012).*
F. Kratz et al., 3 ChemMedChem, 20-53 (2008).*
Michael E. Jung, et al., Synthesis and evaluation of compounds that induce readthrough of premature termination codons. Bioorganic & Medicinal Chemistry Letters. Oct. 2011, 21(19), pp. 5842-5848.
Martin F. Lavin, Generating SM(a)RTer Compounds for Translation Termination Suppression in A-T and Other Genetic Disorders. Molecular Therapy. Sep. 2013, 21 (9), pp. 1650-1652.
Refik Kayali et al., Read-through compound 13 restores dystrophin expression and improves muscle function in the mdx mouse model for Duchenne muscular dystrophy. Human Molecular Genetics. 2012, 21 (18), pp. 4007-4020.
Huttunen et al., "Prodrugs—from serendipity to rational design," Pharmacol Rev, 63(3): 750-771 (2011).

* cited by examiner

*Primary Examiner* — Alexander R Pagano
(74) *Attorney, Agent, or Firm* — Foley Hoag LLP; David Halstead; Lucas Watkins

(57) ABSTRACT

Premature termination codon readthrough prodrug compounds, compositions thereof, and methods of making and using the same are provided. In certain embodiments, the compounds are of Formula Ia or a pharmaceutically acceptable salt, solvate, polymorph, hydrate, ester, isomer, stereoisomer, or tautomer thereof,

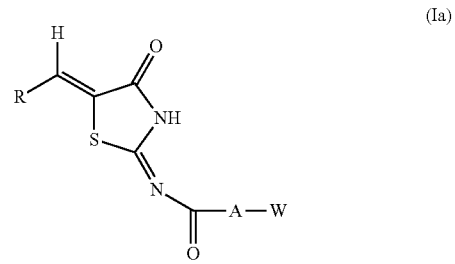

wherein R, A and W are as described herein.

25 Claims, 26 Drawing Sheets

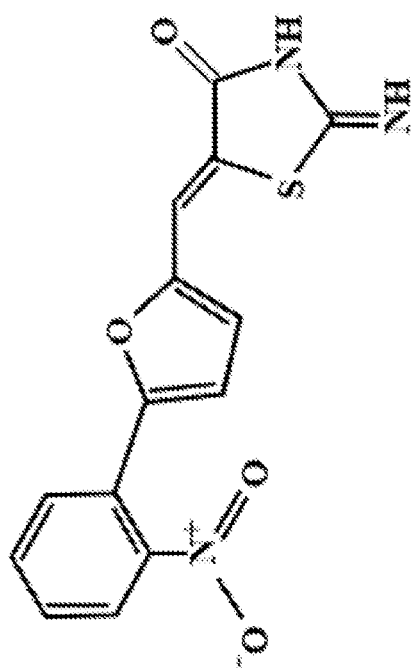
Figure 1. Structure of (Z)-2-imino-5-((5-(2-nitrophenyl)furan-2-yl)methylene)thiazolidin-4-one (RTC13).
RTC13: compound 5

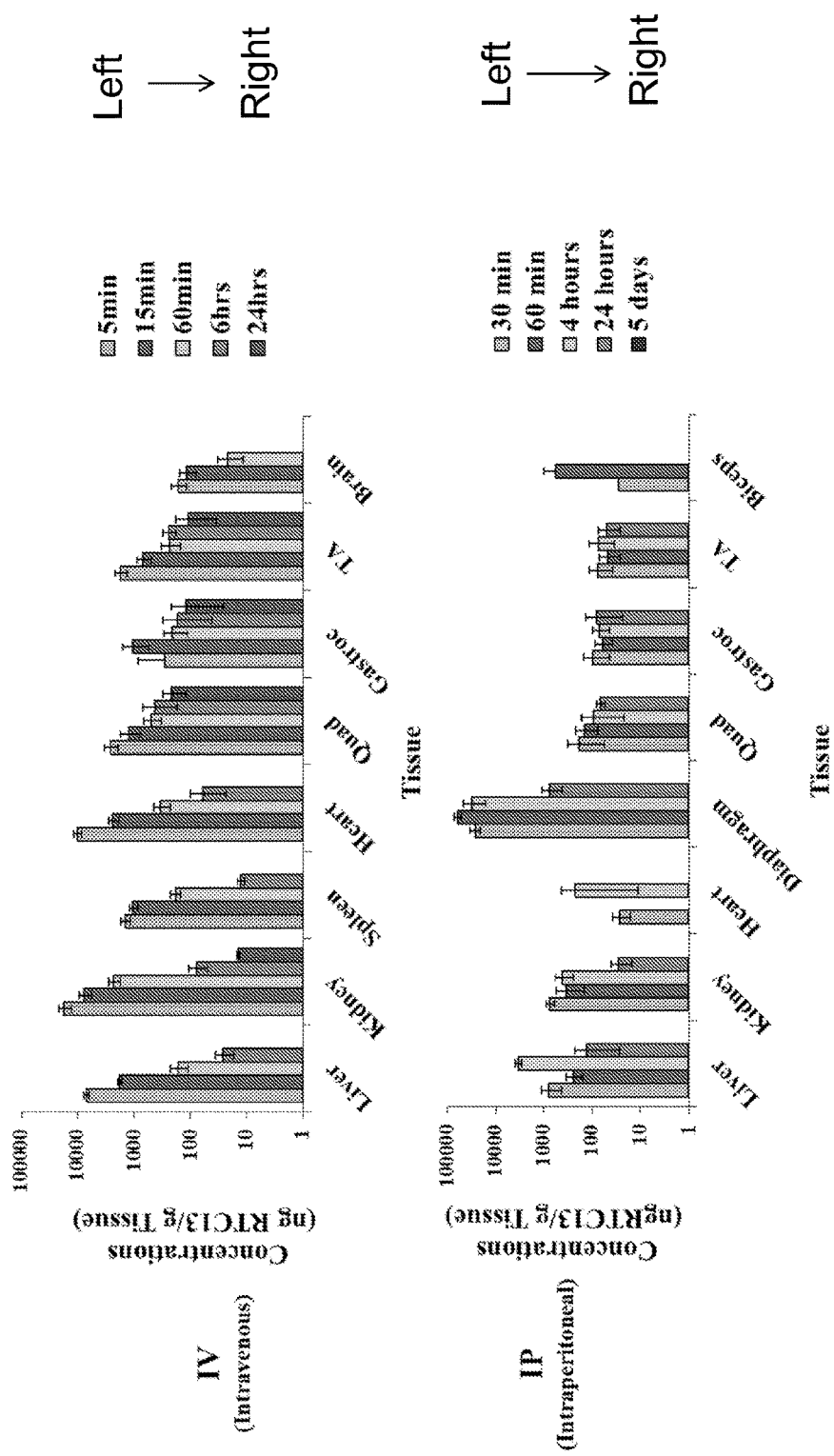

**Fig. 2. Distribution of RTC13 in *mdx* mice after systemic administration.**
Pharmacokinetics and biodistribution of RTC13 after intravenous (IV) and intraperitoneal (IP) injections. Injections were performed at a concentration of 5 mg/kg and f 30 mg/kg for the IV and IP injection respectively.. The predicted effective dose of the parent compound has been computed to be 2 mg/kr.
RTC13: compound 5

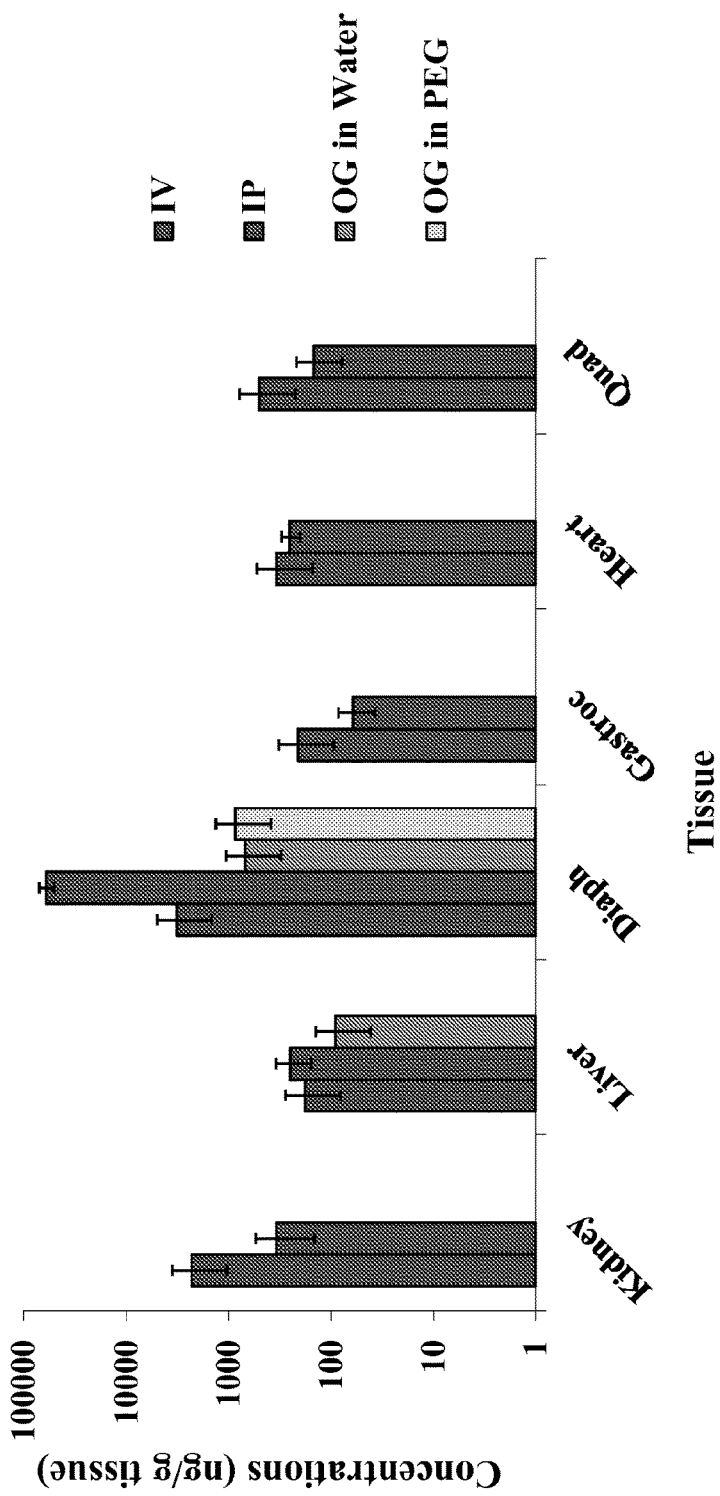
Fig. 3. Distribution of RTC13 in *mdx* mice after systemic administration.
Oral administration of RTC13 was performed at a dose f 60 mg/kg. The distribution of the compound was assessed 60 min after oral gavage (OG) and compared to that achieved after IV injection administered at a dose of 5 mg/kg or IP injection given at a dose of 30 mg/kg.
RTC13: compound 5

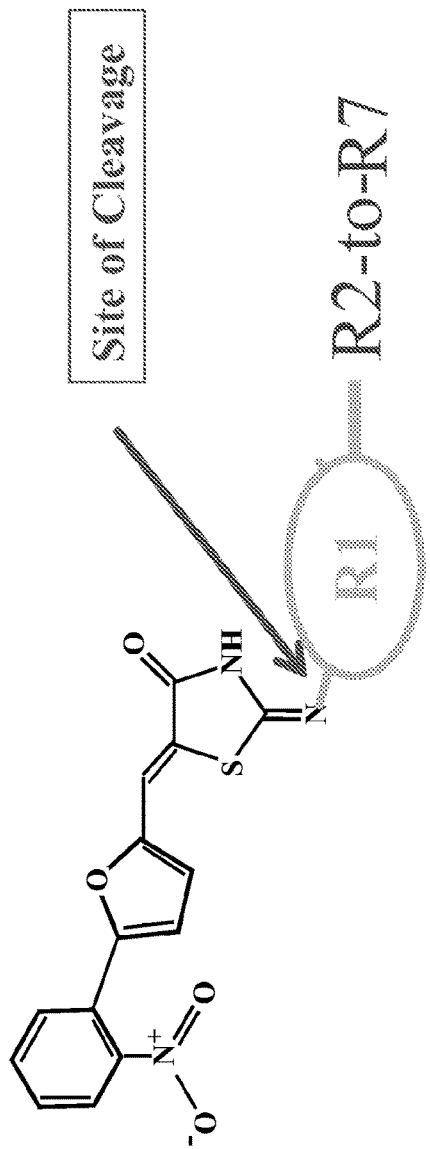

Fig. 4. General structure of RTC13 prodrugs.

The derivatives contain a linker (R1) which is identical for all the analogs and a second group which differs from prodrug to prodrug. The derivatives are designed to increase the solubility of the parent compound and improve its absorption. Groups R2 through R7 represent 6 possible structures that are conjugated to the linker to produce 6 different prodrugs. The predicted site of cleavage in the liver is shown in red.

RTC 13: compound 5

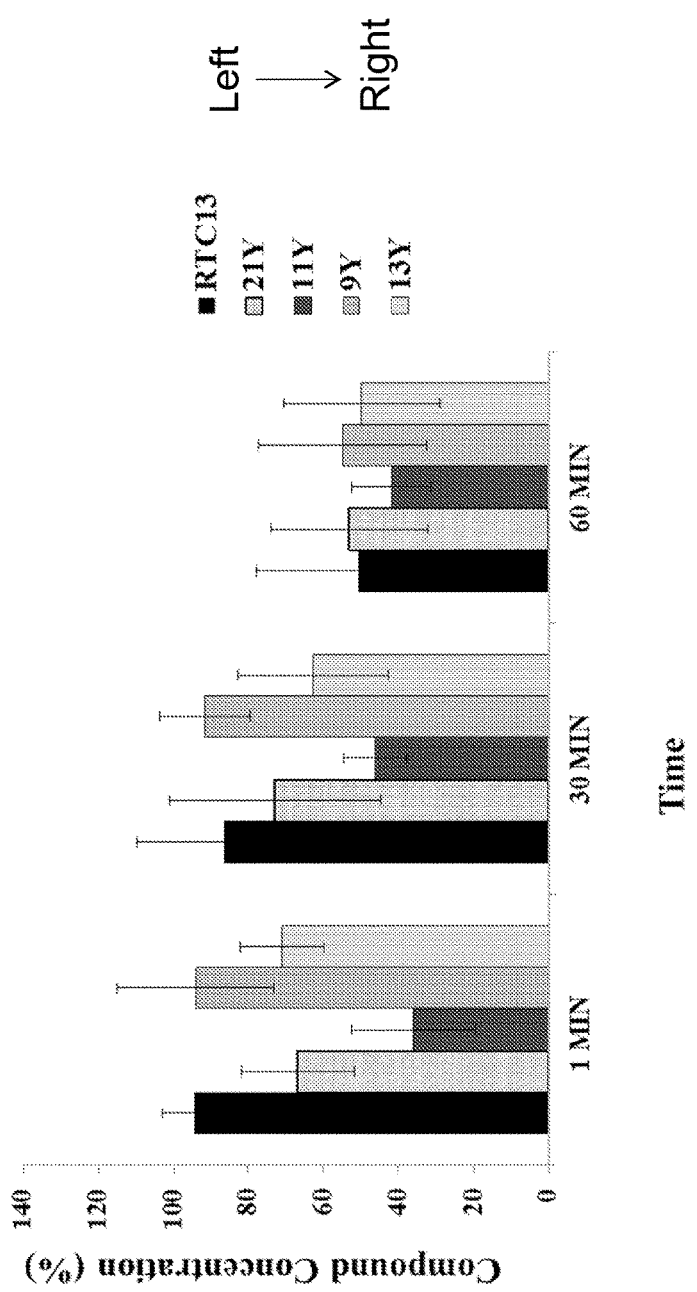
Fig. 5. Microsomal stability assay in liver extracts.
Compounds (5 μg) were incubated at 37°C in fresh liver homogenate (125 mg) isolated from C57 mice in the presence of NADPH (2 mM)
RTC13: compound 5
21Y: compound 16
11Y: compound 20
9Y: compound 12
13Y: compound 8

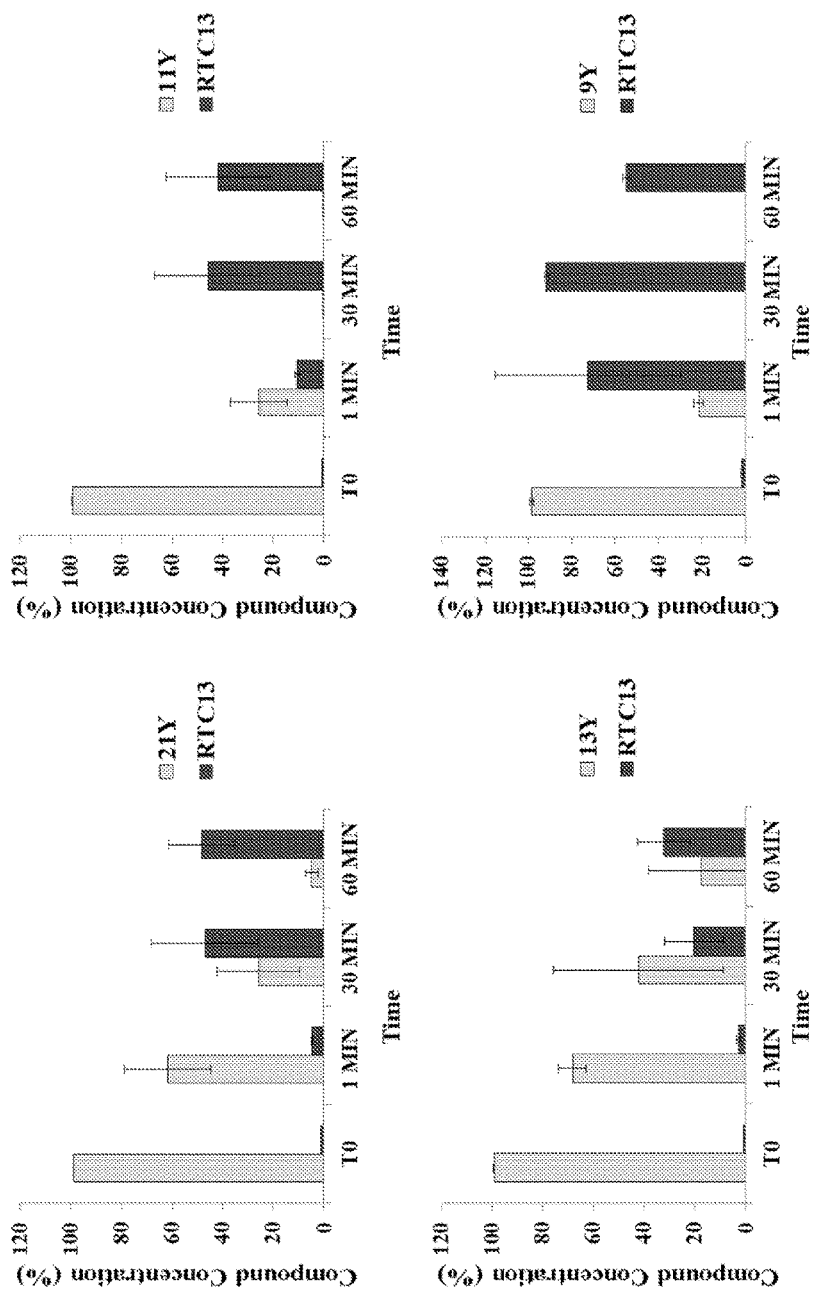
Fig. 6. Rate of conversion of prodrug into parent drug (RTC13) in liver extract.
Compounds (5 μg) were incubated at 37°C in fresh liver homogenate (125 mg) isolated from C57 mice in the presence of NADPH (2 mM). Conversion of the prodrugs into the parent compound was detected in all samples analyzed as early as 1 min after incubation.
RTC13: compound 5; 21Y: compound 16; 11Y: compound 20; 9Y: compound 12; 13Y: compound 8

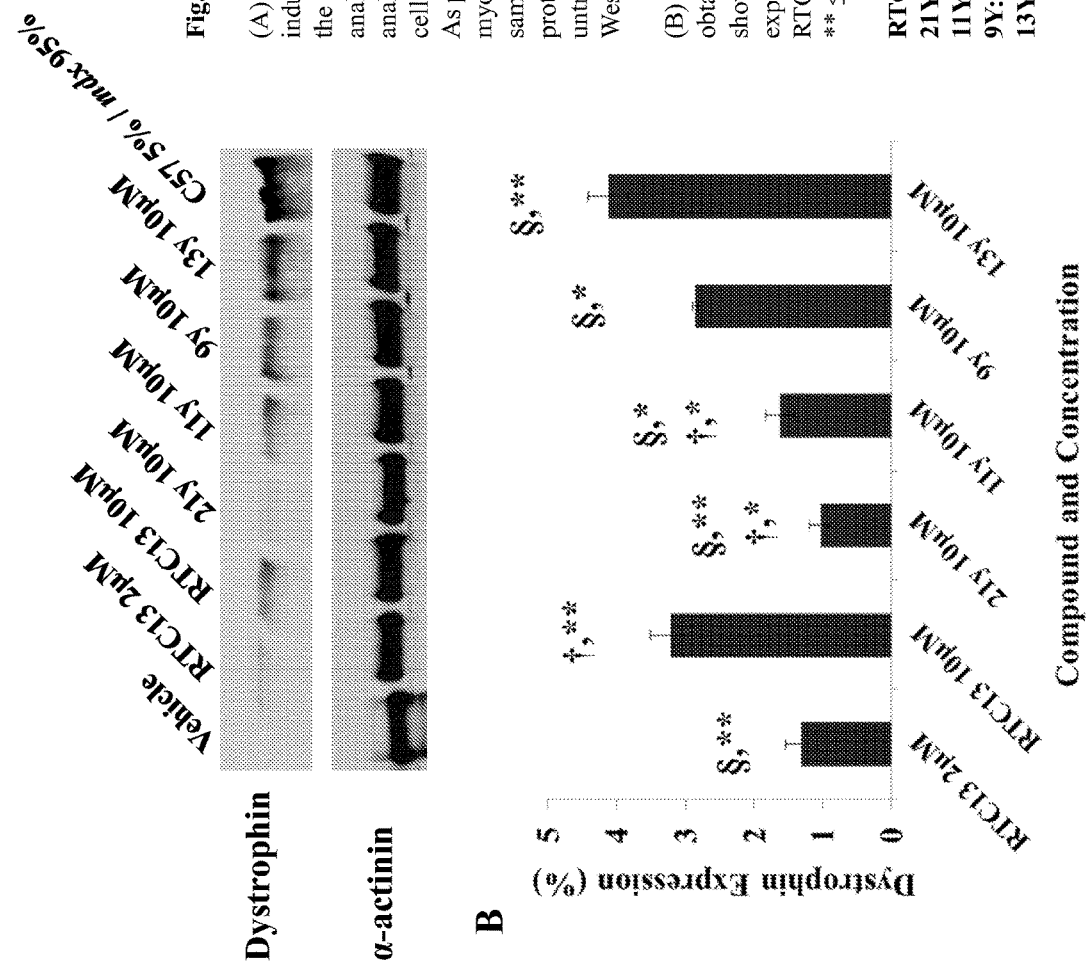

Fig. 7. Dystrophin expression in *mdx* myotubes.

(A) Muscle cells isolated from the *mdx* mouse were induced to differentiate for 16 hrs and then exposed to the compounds for an additional 80 hrs prior to protein analysis. Dystrophin was detected by Western blot analysis in all cells treated with the prodrugs but not in cells exposed to DMSO or in untreated *mdx* myotubes. As positive control, protein isolated from wild type myotubes maintained in differentiation media for the same period of time (corresponding to 5% of total protein) were mixed with proteins isolated from untreated *mdx*. Equal loading was confirmed by Western blot using α-actinin as internal control.

(B) Quantitative analysis of protein levels were obtained from multiple independent experiments and showed a dose response increase in dystrophin expression in all compounds tested. (†: significant to RTC13 2μM; §: significant to RTC13 10μM; *: ≤ 0.03; ** ≤ 0.002)

RTC13: compound 5
21Y: compound 16
11Y: compound 20
9Y: compound 12
13Y: compound 8

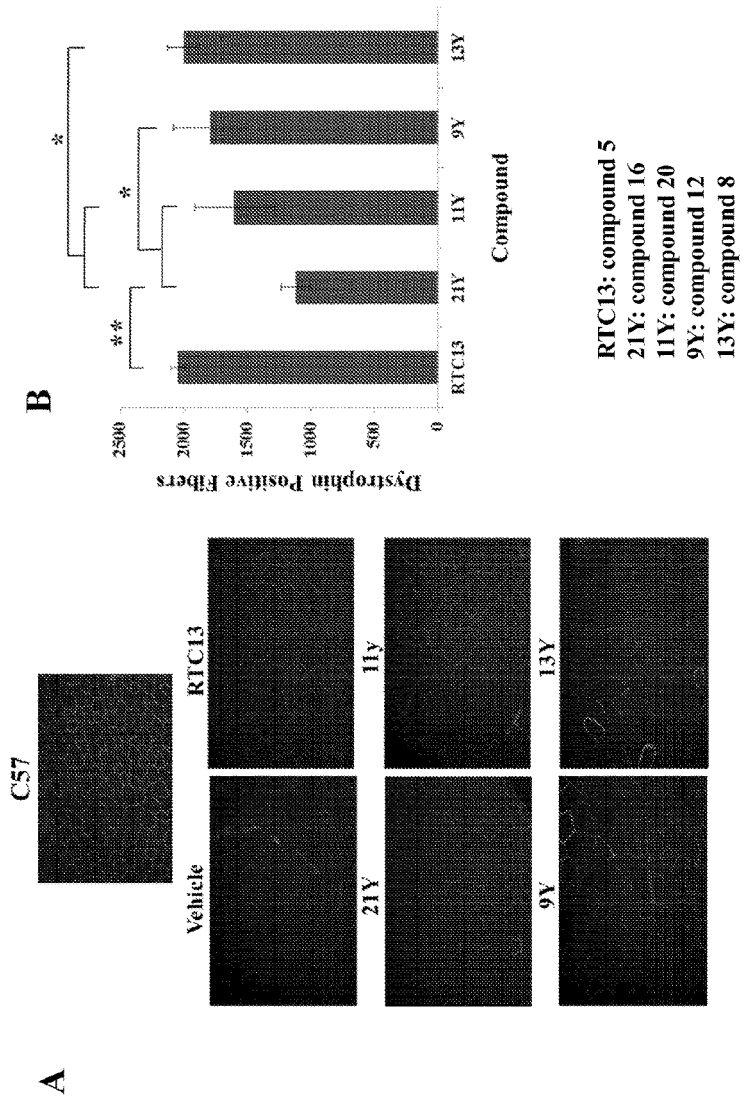

Fig. 8. Dystrophin expression after intramuscular injection.

(A) Dystrophin staining in TA muscles of *mdx* mice injected with RTC13 or its derivatives and analyzed two weeks after delivery of compounds and compared to muscles treated with DMSO alone. Dystrophin expression was evident in muscles that received the compounds but not in sham-injected muscles. Weak expression was detected in TA muscles injected with gentamicin and RTC14. (N = 4 muscles per compound)

(B) The number of dystrophin positive fibers was determined across the length of the muscle. TA injected with RTC13Y showed a significantly higher number of positive fibers than muscles that received 21Y and 11Y. No significant diferneces were detected in muscles that received RTC13 when compared to muscles that received 9Y and 13Y. Shown here is the average number of dystrophin positive fibers per cross-sectional area containing the highest number of positives. (N = 4 muscles per compound; *: p = 0.0008; **: p ≤ 0.04)

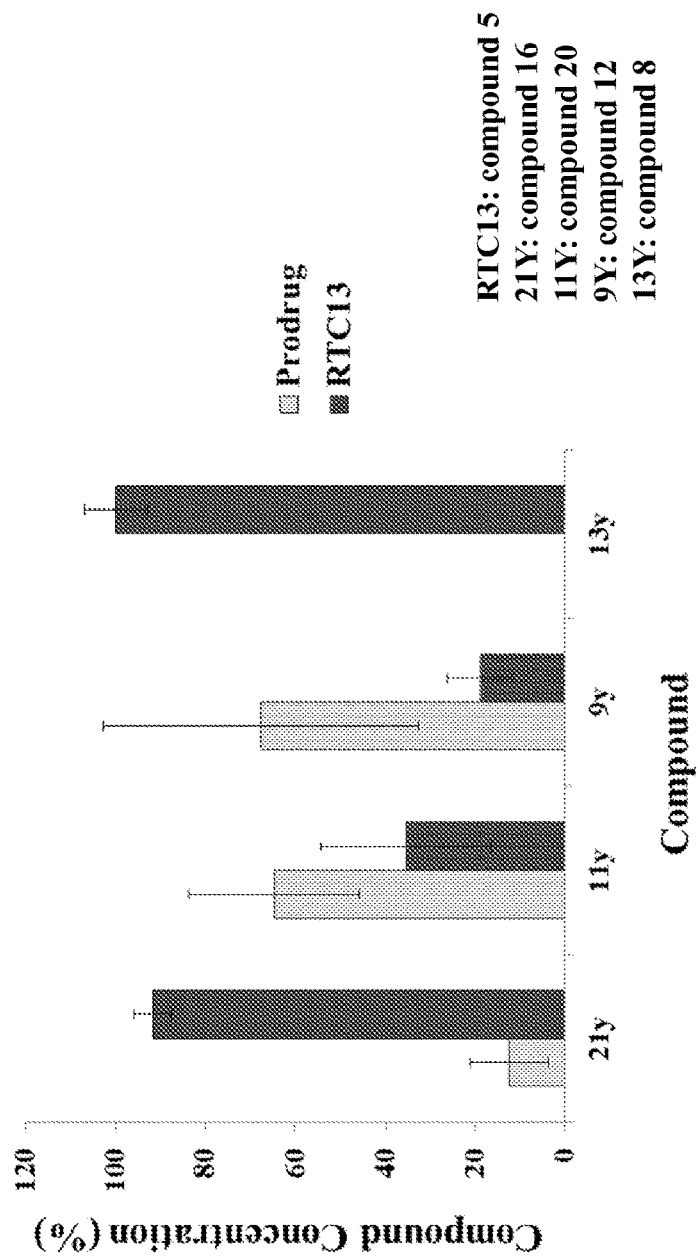
Fig. 9. Rate of conversion of prodrugs into parent drug (RTC13) in muscle *in vivo*.
Prodrugs were injected into Tibialis Anterior and muscles were isolated 24 hrs after intramuscular injection.

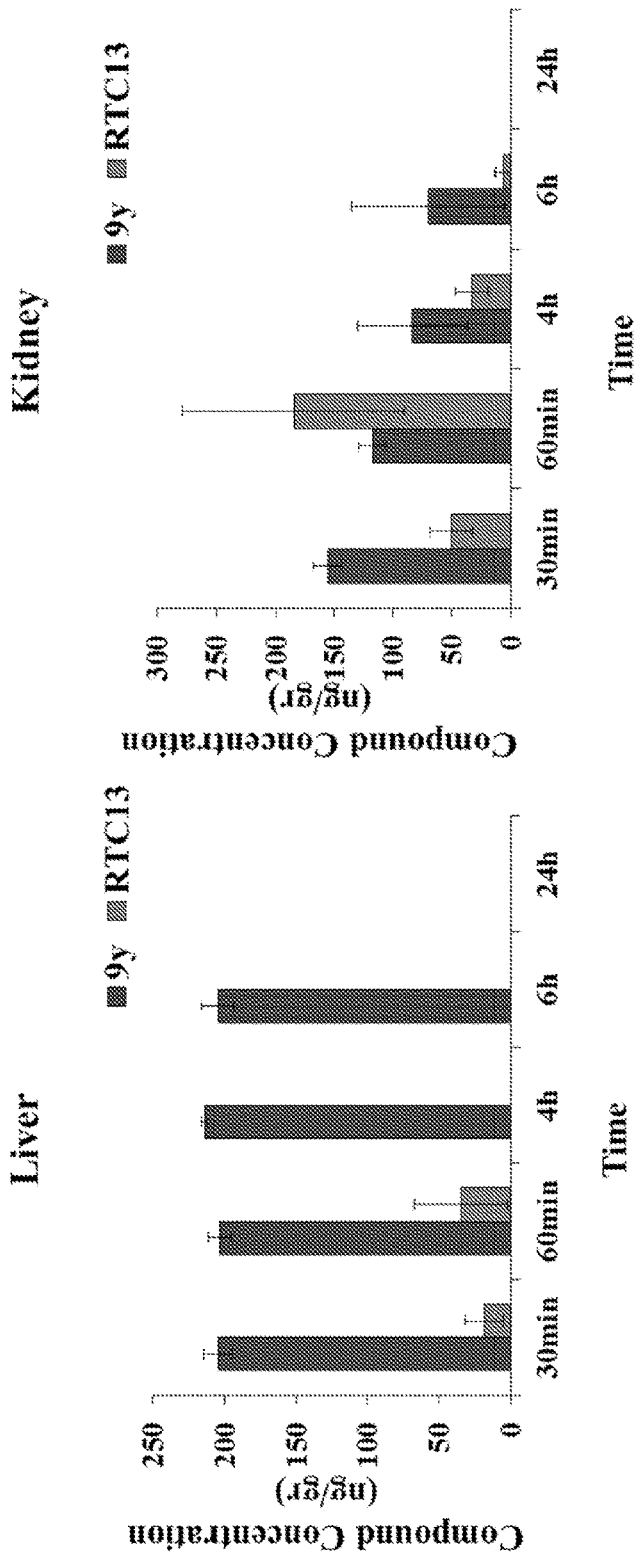
**Figure 10. Pharmacokinetic studies in *mdx* mice after oral administration of 9Y in liver and kidney.**
The compound was administered at a dose of 60 mg/kg in 6-8 weeks old C57 BL/10 mice and tissues were analyzed after oral administration at the time points indicated.
RTC13: compound 5; 9Y: compound 12.

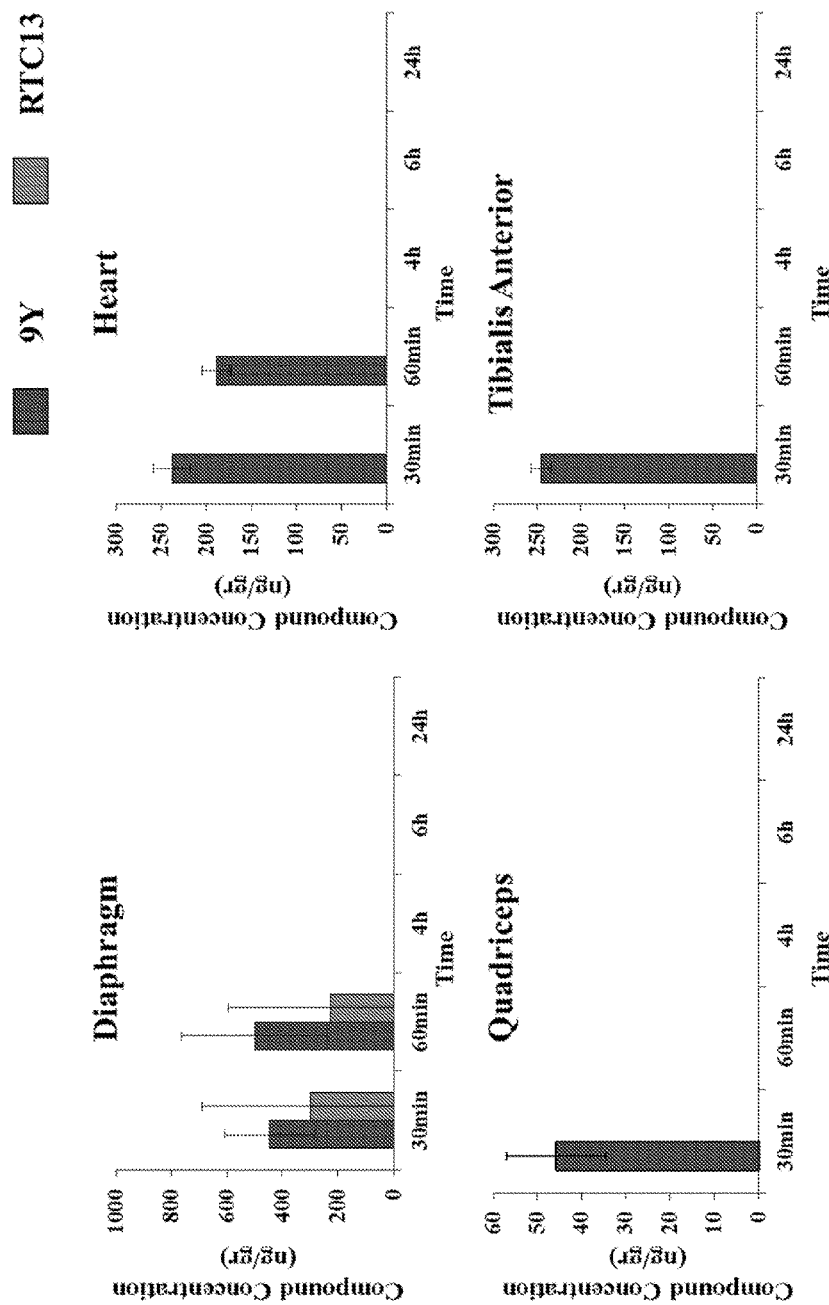
Figure 11. Pharmacokinetics studies in *mdx* mice after oral administration of 9Y in muscle.
The compound was administered at a dose of 60 mg/kg in 6-8 weeks old C57 BL/10 mice and tissues were analyzed after oral administration at the time points indicated.
RTC13: compound 5; 9Y: compound 12.

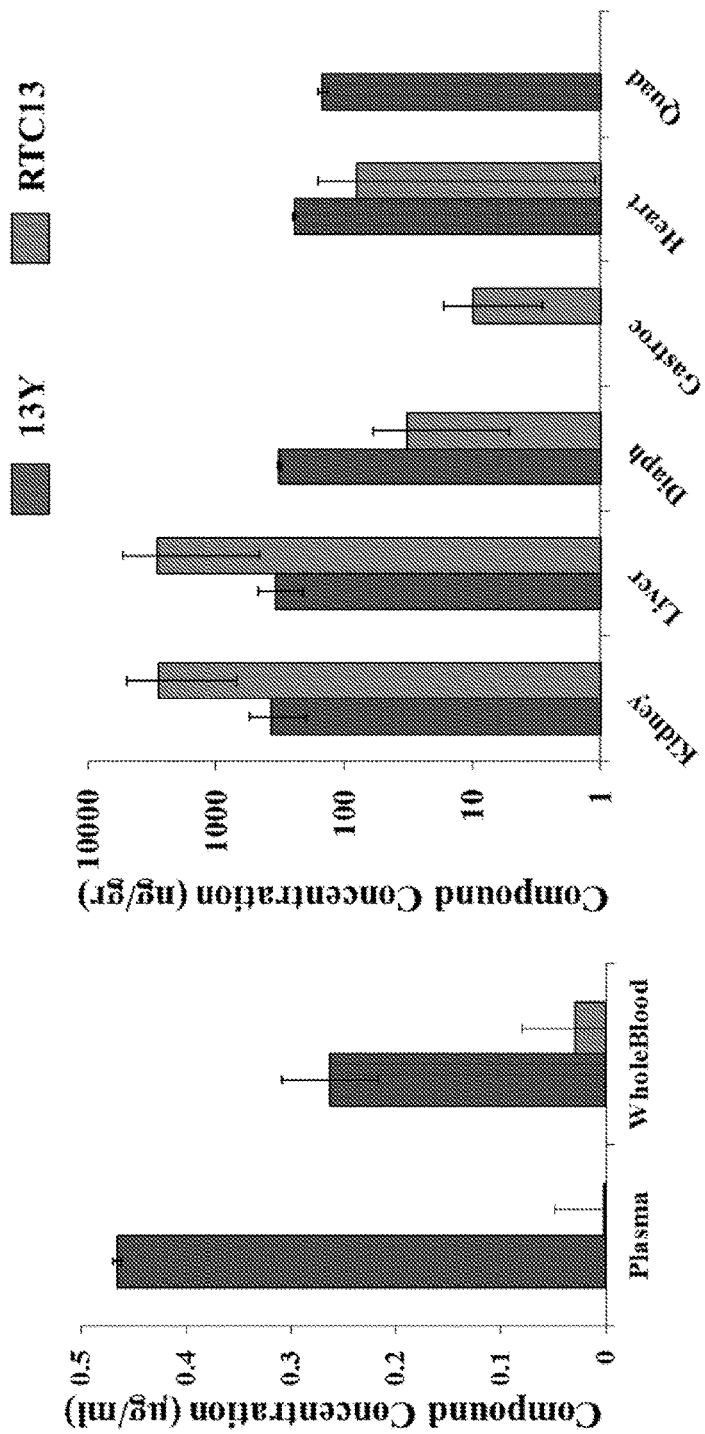
Figure 12. Pharmacokinetics studies in *mdx* mice after oral administration of 13Y.
The compound was administered at a dose of 60 mg/kg in 6-8 weeks old *mdx* mice and tissues were analyzed 60 min after oral administration.
RTC13: compound 5; 13Y: compound 8.

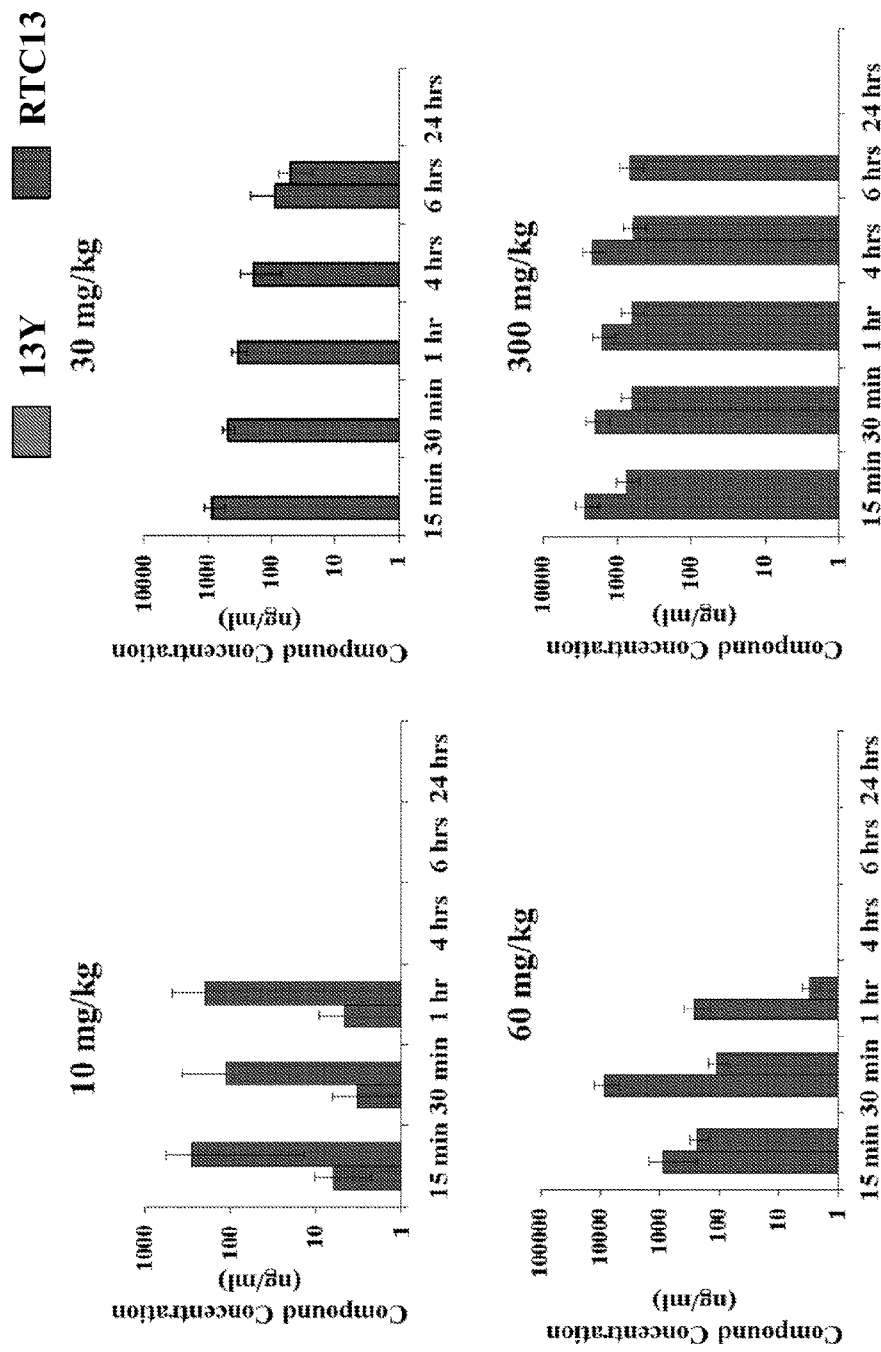
Figure 13. Pharmacokinetics studies in wild type mice after oral administration of 13Y.
The compound was administered at the indicated dosages in 6-8 weeks old C57BL/10 mice and tissues were analyzed in plasma 15 min, 30 min, 1 hr, 4 hrs, 6 hrs and 24 hrs after gavage.
RTC13: compound 5; 13Y: compound 8.

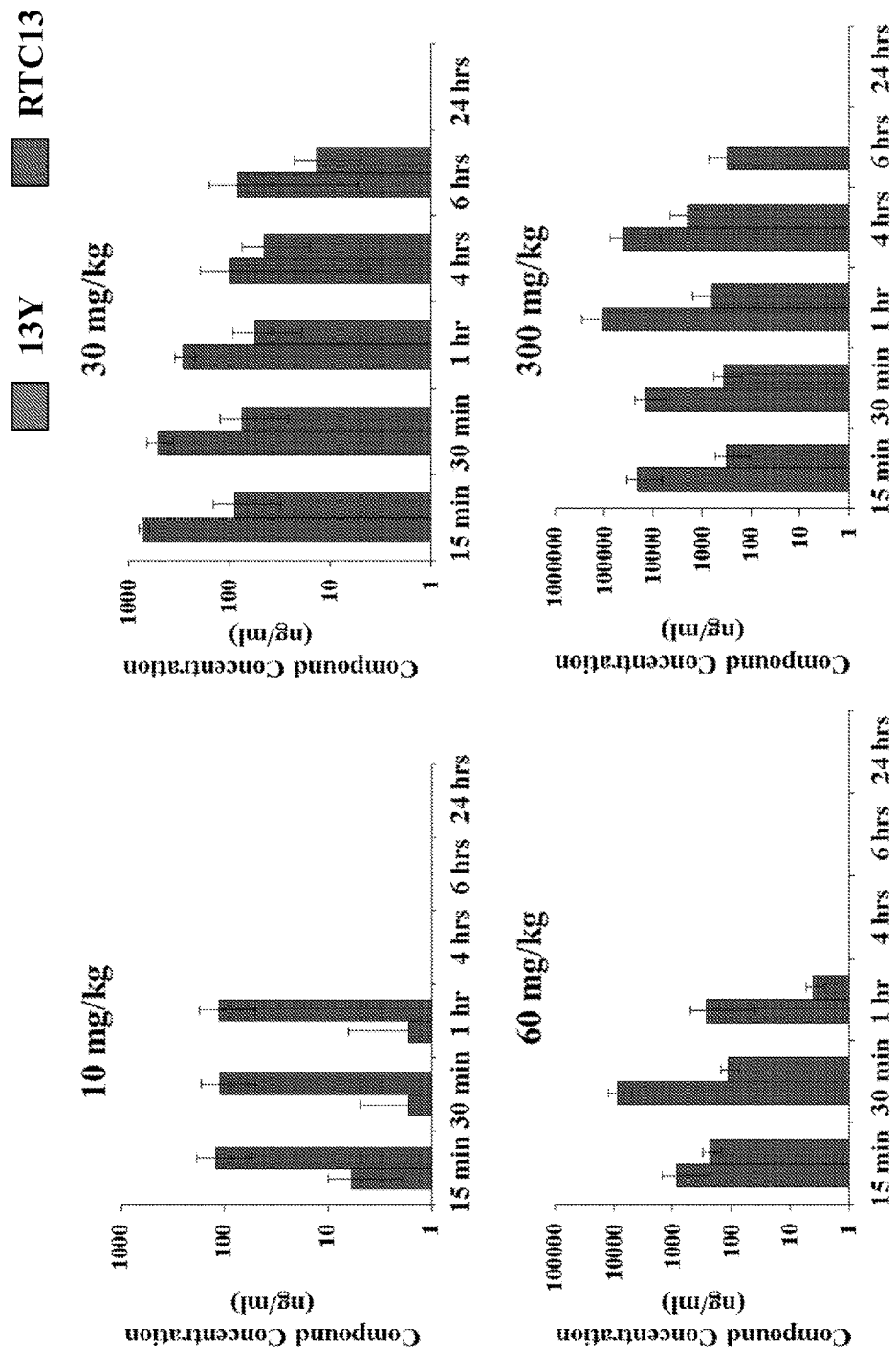
Figure 14. Pharmacokinetics studies in wild type mice after oral administration of 13Y.
The compound was administered at the indicated dosages in 6-8 weeks old C57BL/10 mice and tissues were analyzed in whole blood 15 min, 30 min, 1 hr, 4 hrs, 6 hrs and 24 hrs after gavage.
RTC13: compound 5; 13Y: compound 8.

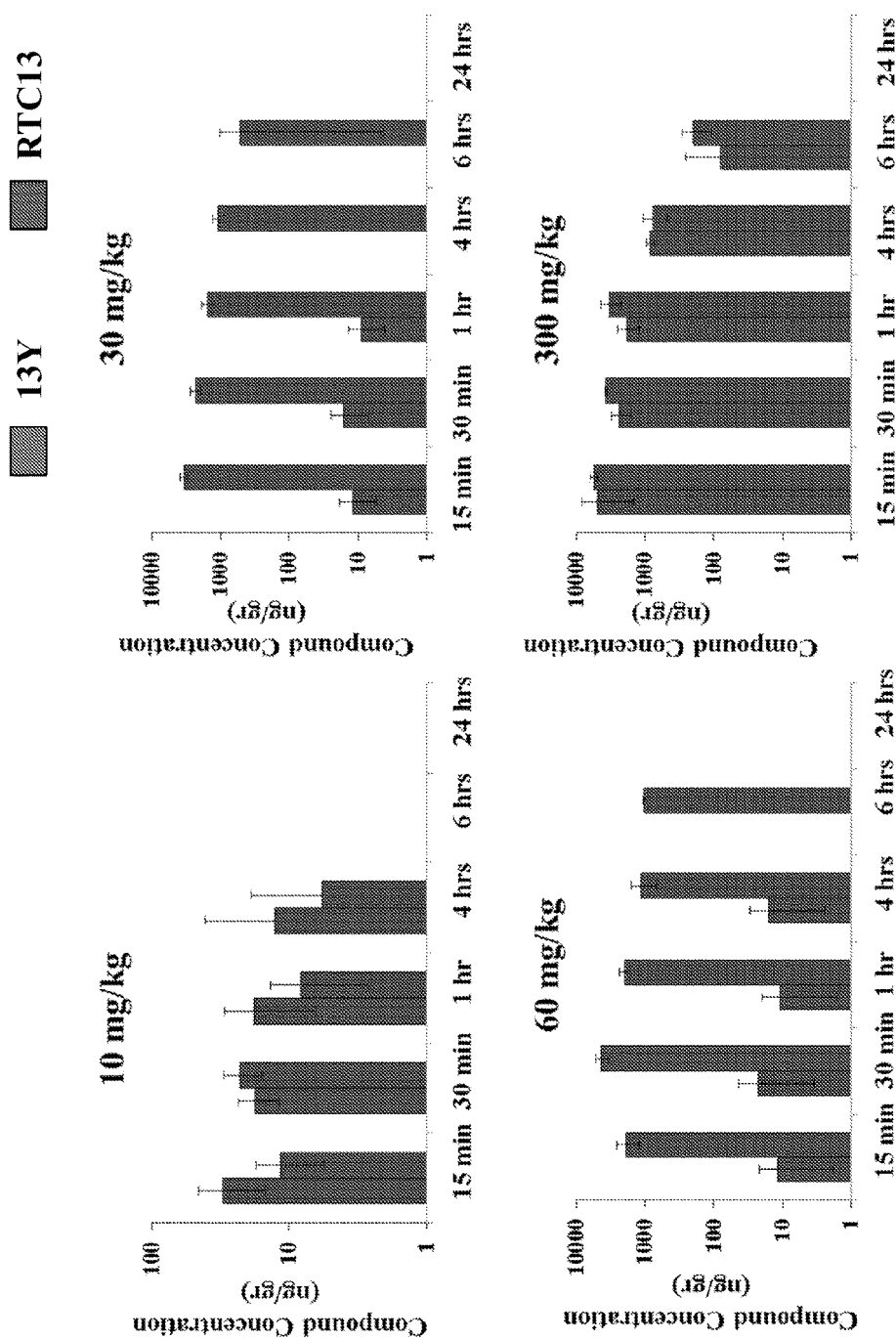
Figure 15. Pharmacokinetics studies in wild type mice after oral administration of 13Y.
The compound was administered at the indicated dosages in 6-8 weeks old C57BL/10 mice and tissues were analyzed in liver 15 min, 30 min, 1 hr, 4 hrs, 6 hrs and 24 hrs after gavage.
RTC13: compound 5; 13Y: compound 8.

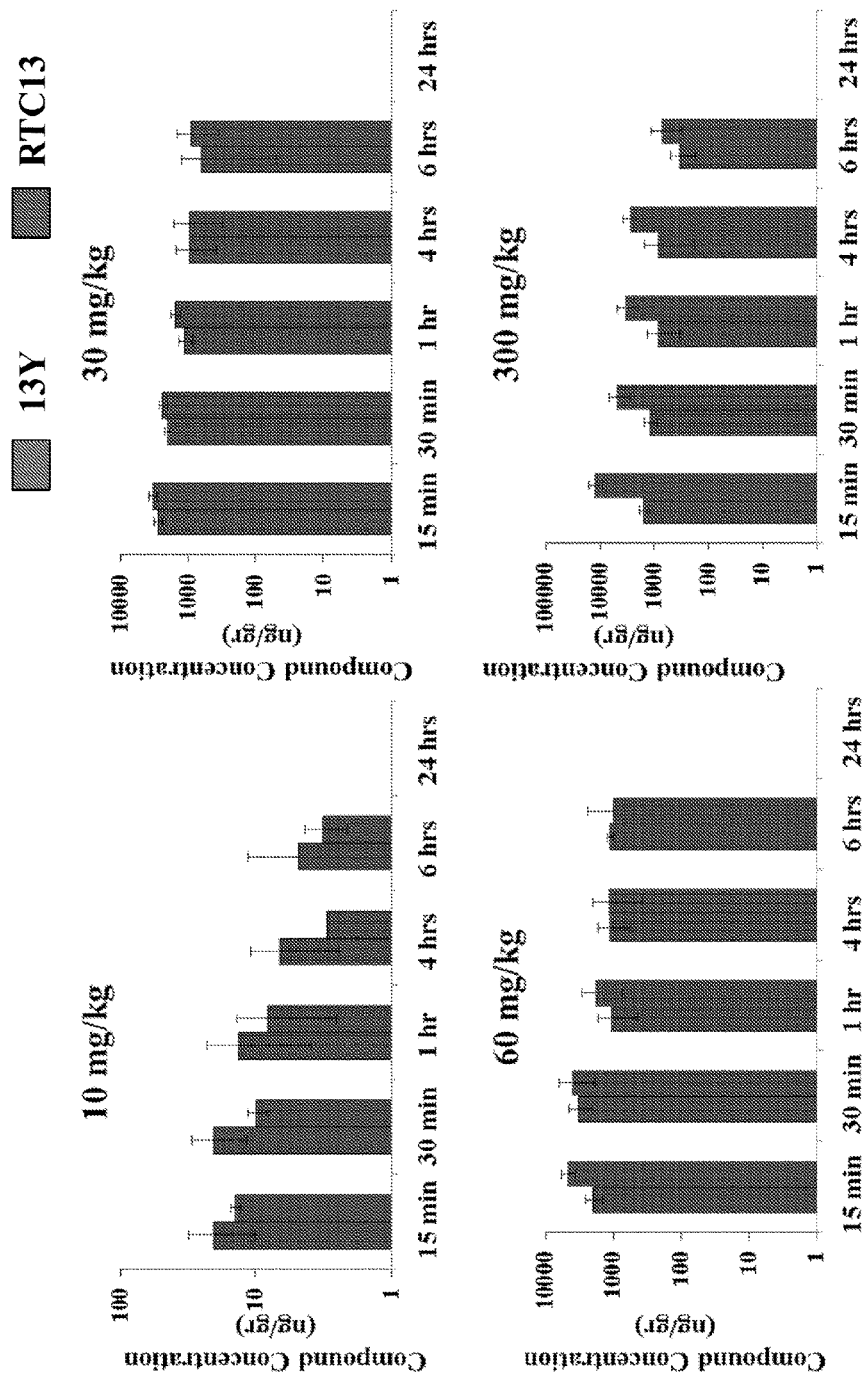
Figure 16. Pharmacokinetics studies in wild type mice after oral administration of 13Y.
The compound was administered at the indicated dosages in 6-8 weeks old C57BL/10 mice and tissues were analyzed in kidney 15 min, 30 min, 1 hr, 4 hrs, 6 hrs and 24 hrs after gavage.
RTC13: compound 5; 13Y: compound 8.

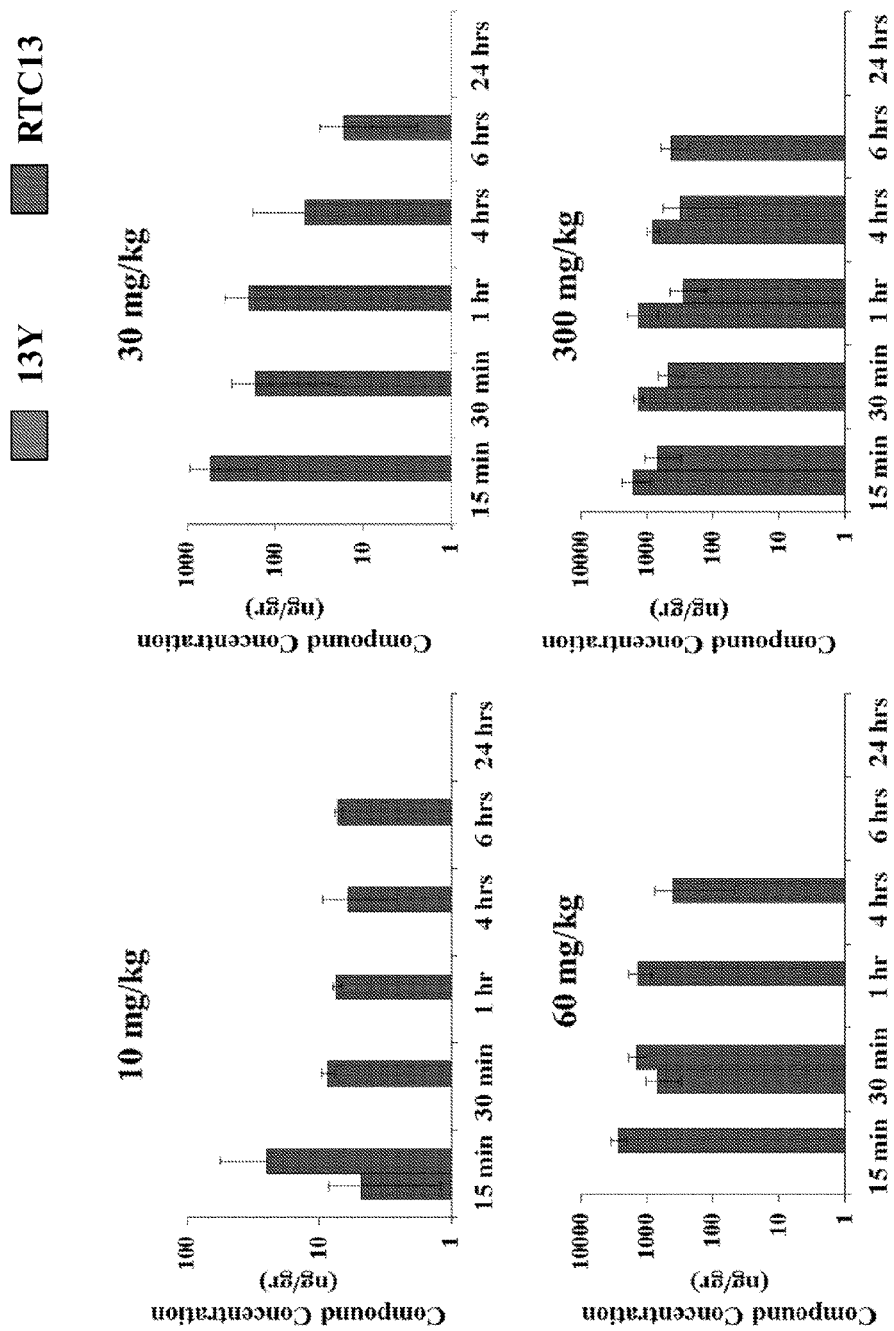
Figure 17. Pharmacokinetics studies in wild type mice after oral administration of 13Y. The compound was administered at the indicated dosages in 6-8 weeks old C57BL/10 mice and tissues were analyzed in quadriceps 15 min, 30 min, 1 hr, 4 hrs, 6 hrs and 24 hrs after gavage.
RTC13: compound 5; 13Y: compound 8.

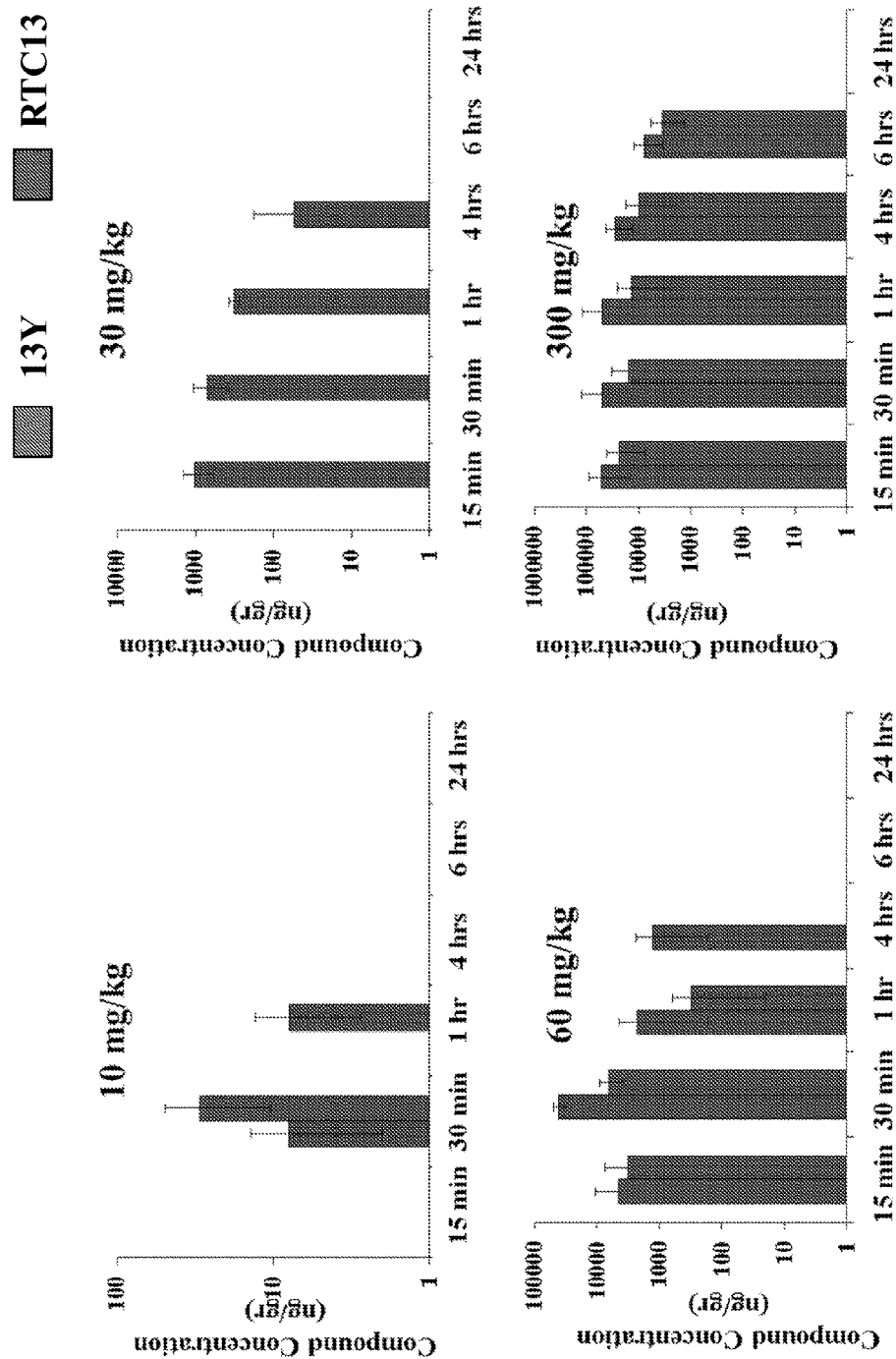
Figure 18. Pharmacokinetics studies in wild type mice after oral administration of 13Y.
The compound was administered at the indicated dosages in 6-8 weeks old C57BL/10 mice and tissues were analyzed in diaphragm 15 min, 30 min, 1 hr, 4 hrs, 6 hrs and 24 hrs after gavage.
RTC13: compound 5; 13Y: compound 8.

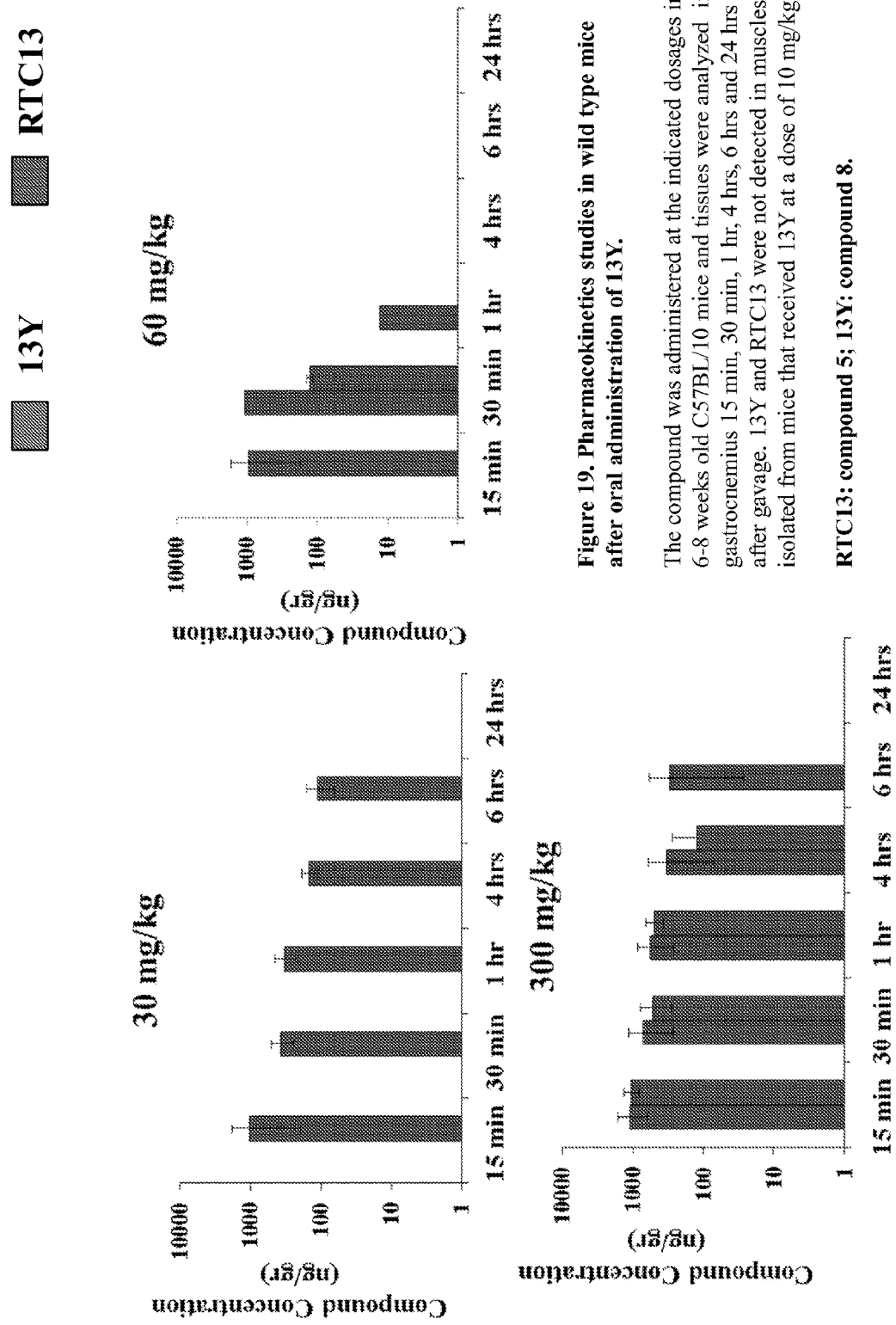
Figure 19. Pharmacokinetics studies in wild type mice after oral administration of 13Y.
The compound was administered at the indicated dosages in 6-8 weeks old C57BL/10 mice and tissues were analyzed in gastrocnemius 15 min, 30 min, 1 hr, 4 hrs, 6 hrs and 24 hrs after gavage. 13Y and RTC13 were not detected in muscles isolated from mice that received 13Y at a dose of 10 mg/kg.
RTC13: compound 5; 13Y: compound 8.

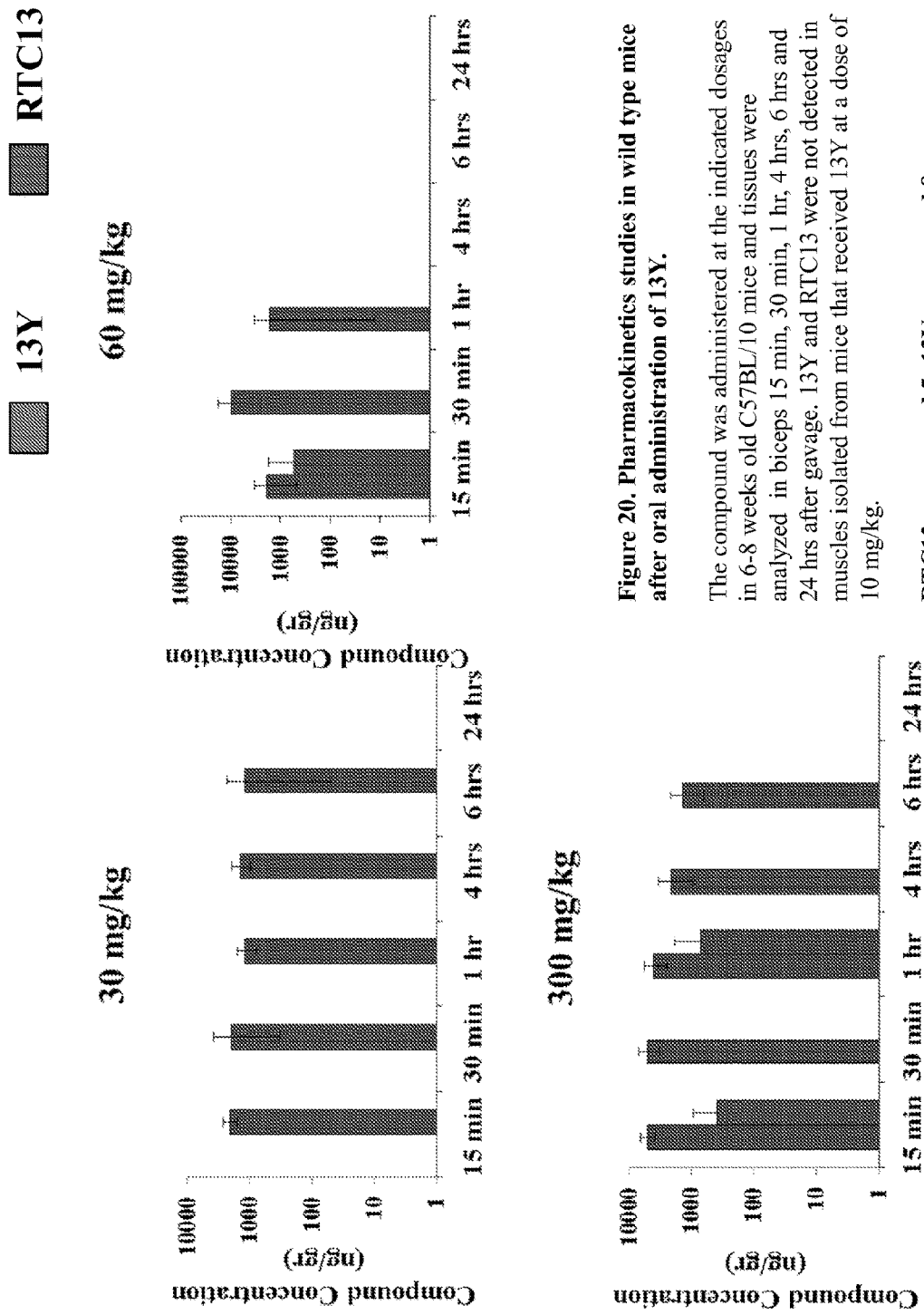
Figure 20. Pharmacokinetics studies in wild type mice after oral administration of 13Y.
The compound was administered at the indicated dosages in 6-8 weeks old C57BL/10 mice and tissues were analyzed in biceps 15 min, 30 min, 1 hr, 4 hrs, 6 hrs and 24 hrs after gavage. 13Y and RTC13 were not detected in muscles isolated from mice that received 13Y at a dose of 10 mg/kg.
RTC13: compound 5; 13Y: compound 8.

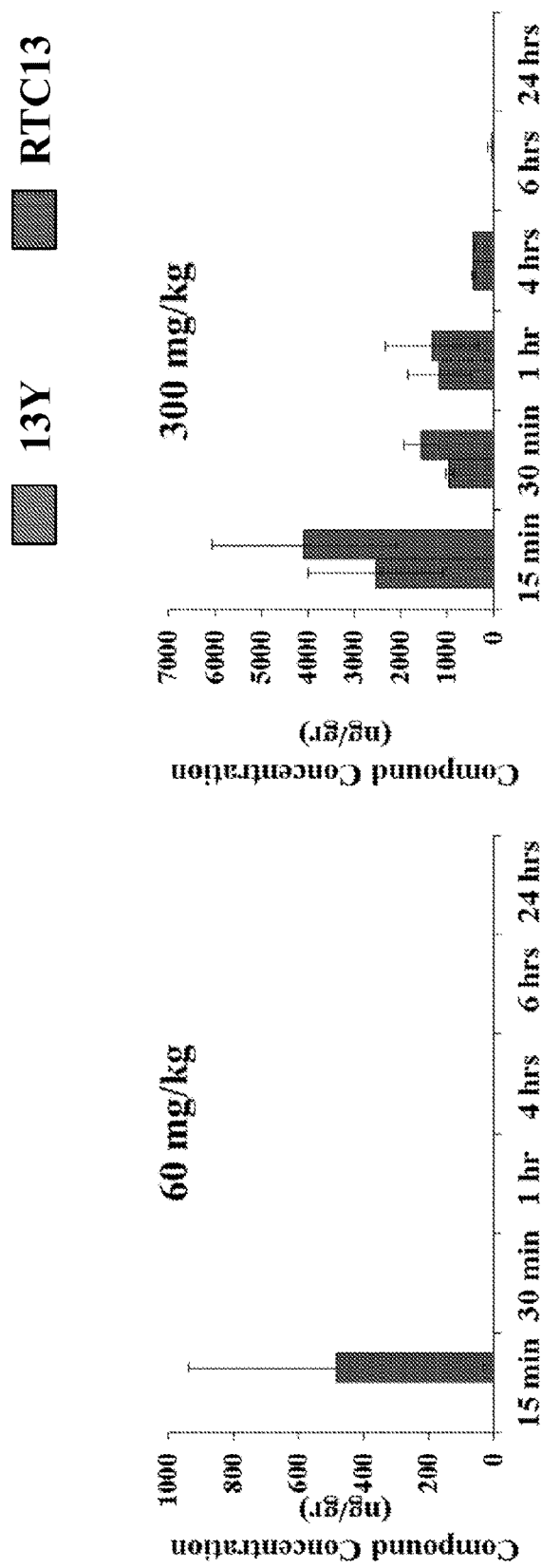
Figure 21. Pharmacokinetics studies in wild type mice after oral administration of 13Y.
The compound was administered at the indicated dosages in 6-8 weeks old C57BL/10 mice and tissues were analyzed in heart 15 min, 30 min, 1 hr, 4 hrs, 6 hrs and 24 hrs after gavage. 13Y and RTC13 were not detected in muscles isolated from mice that received 13Y at a dose of 10 mg/kg and 30 mg/kg.
RTC13: compound 5; 13Y: compound 8.

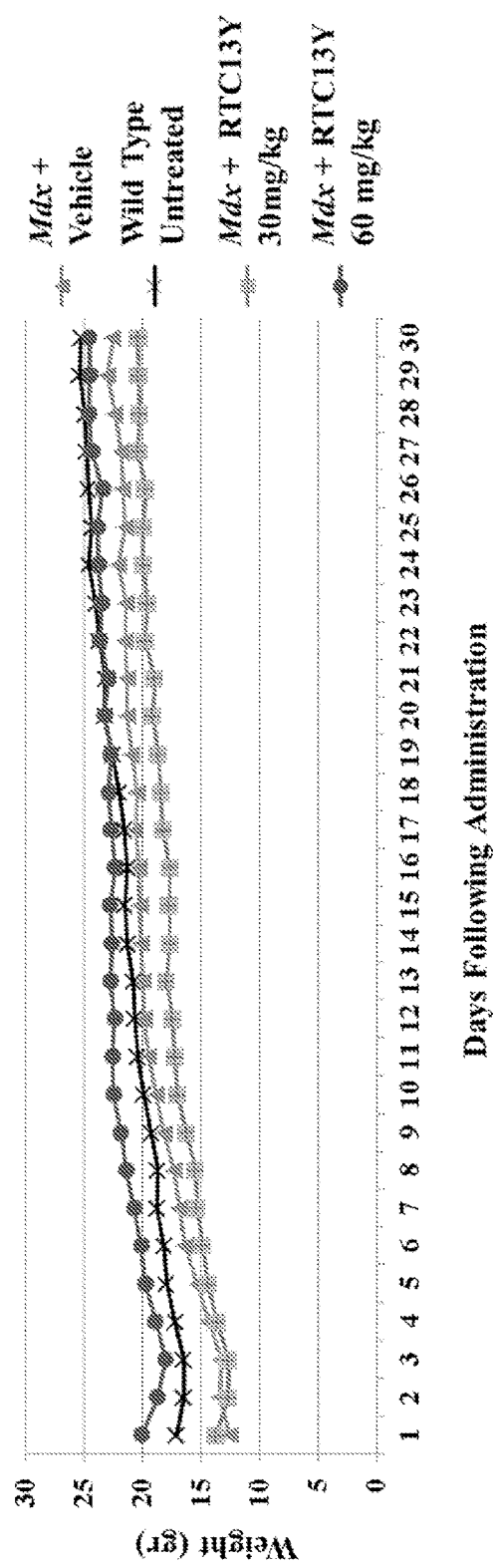
Figure 22. Effect of oral administration of 13Y on body weight.
The compound was administered in 6-8 weeks old *mdx* and C57BL/10 mice three times per day at the indicated dosages and weight was recorded daily.
13Y: compound 8

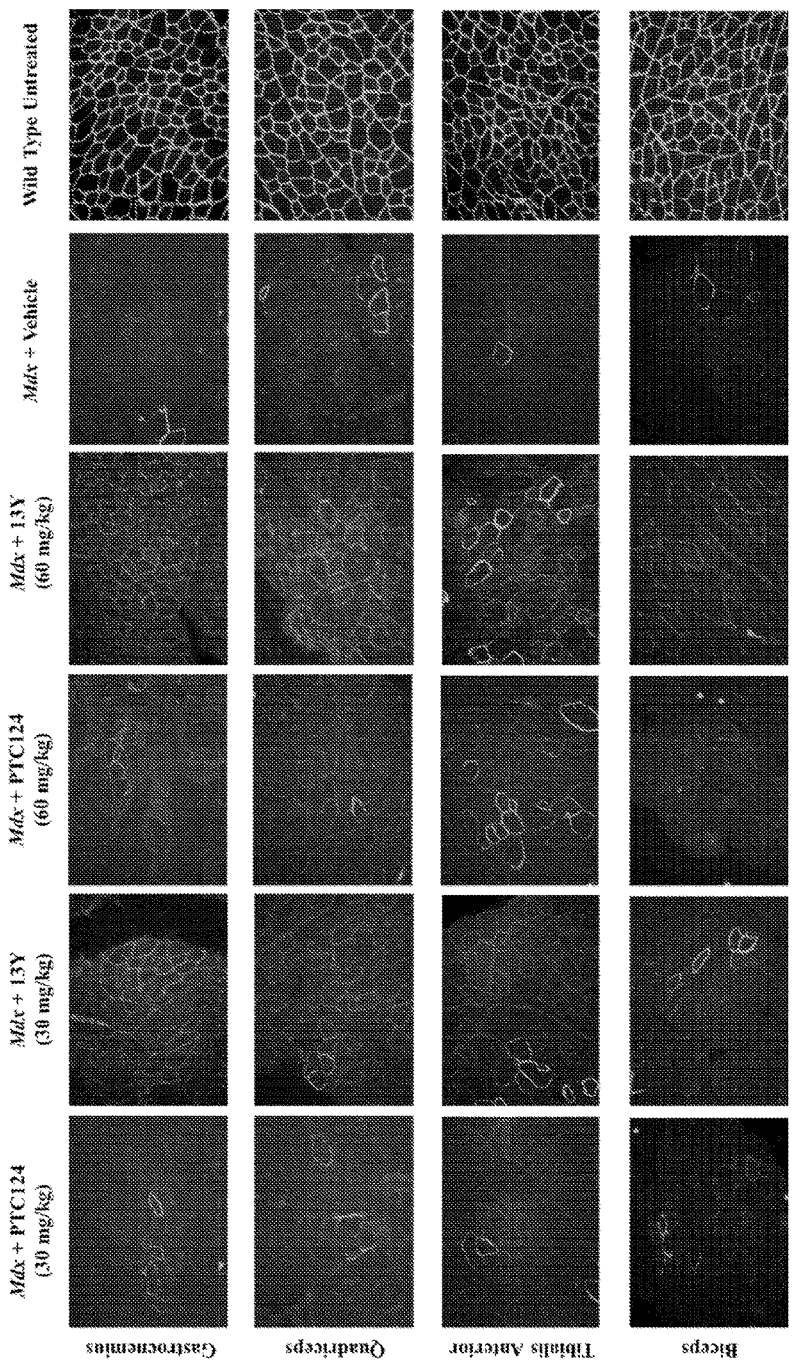

**Figure 23. Dystrophin expression in *mdx* mice following oral administration of 13Y**
Compounds were administered in 6-8 weeks old *mdx* mice three times per day for one month at the indicated dosages. Dystrophin expression was evident in muscles that received the compounds but not in sham-injected muscles. Muscles isolated from mice that received 13Y at a dose of 30 mg/kg or 60 mg/kg showed higher levels of dystrophin expression than muscles obtained from *mdx* mice treated with PTC124 (N = 6 muscles per compound; scale bar: 100 μm)

13Y: compound 8

**Figure 24. Functional improvement in *mdx* mice after treatment.**

(A) The forelimb grip test was used to assess the effects of systemic administration of RTCs on muscle strength. A significant force recovery was detected in *mdx* mice treated with 13Y compared to sham-injected control mice and mice that received PTC124. Muscle strength remained significantly lower than that detected in wild type mice. Similar results were obtained in duplicate experiments. (N = 5 mice per treatment group; * p < 0.05; ** p < 0.005).

(B) Mice that received 13Y showed a significant improvement in the ability to hang on a wire compared to sham-injected mice or mice treated with PTC124. No significant improvements were detected in mice that received PTC124 compared to untreated mice. Results were confirmed in duplicate experiments (N = 6 mice per treatment group; * p < 0.05; ** p = 0.005)

13Y: compound 8

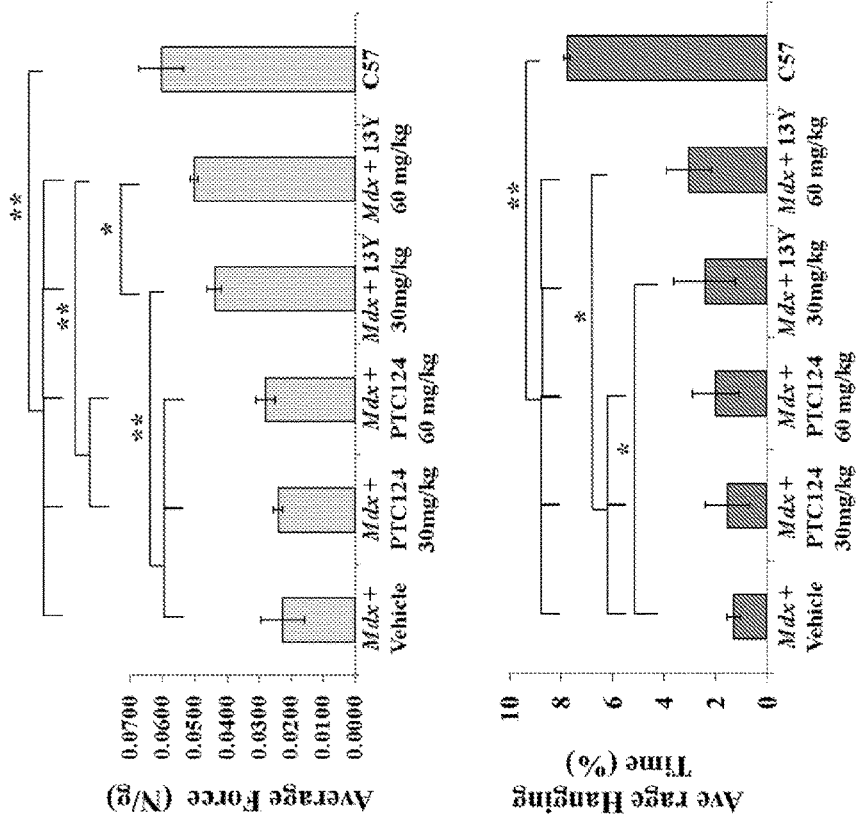

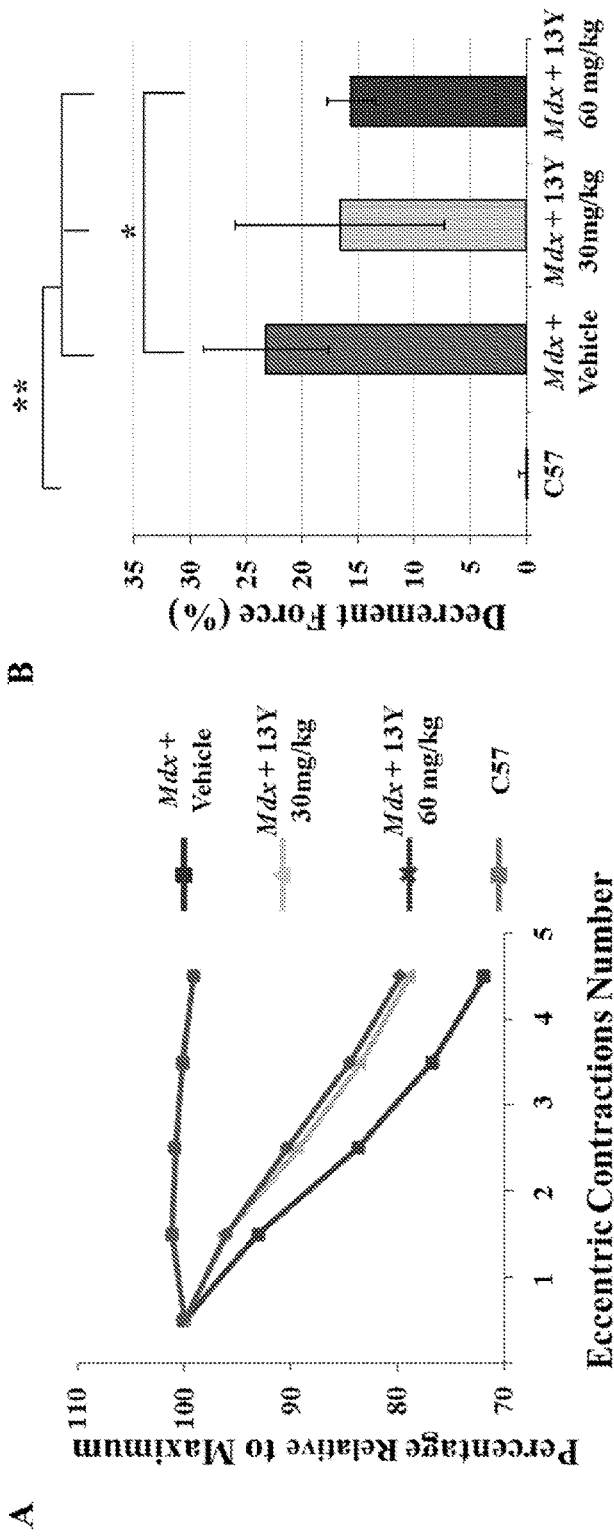

**Figure 25. Loss of specific force in diaphragm muscles of *mdx* mice treated with 13Y**

*In vitro* force measurement of diaphragm muscles of wild type and *mdx* mice treated with either vehicle, 13Y at a dose of 30 mg/kg or 13Y at a dose of 60 mg/kg three times per day at intervals of 4 hrs for up to one month. Muscles isolated from untreated and treated mice muscles were subjected to a series of five eccentric contractions with a 5-min rest between contractions.
(A) An improvement if loss of force was detected in mice that received 13Y at a dose of 30 mg/kg and 60 mg/kg).
(B) The decrement in force was significantly lower in mice that received 13Y at a dose of 60 mg/kg compared to mice that received vehicle only. (N=4, *: p ≤ 0.05; **: p ≤ 0.03)

13Y: compound 8

Figure 26. Table 2. Serum chemistry of *mdx* mice treated with RTCs three times a day for one month.

| | Mdx Untreated | Mdx + PTC124 (30 mg/kg) | Mdx + PTC124 (60 mg/kg) | Mdx + 13Y (30 mg/kg) | Mdx + 13Y (60 mg/kg) | Wild Type untreated |
|---|---|---|---|---|---|---|
| Direct Bilirubin | 0.175 (± 0.05) | 0.2025 (± 0.04) | 0.2 (± 0.01) | 0.18 (± 0.05) | 0.175 (± 0.08) | 0.2 (± 0) |
| Blood Urea Nitrogen | 27 (± 1.63) † | 22 (± 1.30) *,† | 19.75 (± 2.45) *,† | 20.2 (± 1.73) *,† | 22.5 (± 3.69) *,† | 29.25 (± 0.96) * |
| Creatine | 0.225 (± 0.02) † | 0.185 (± 0.05) | 0.2375 (± 0.06) *,† | 0.22 (± 0.03) | 0.275 (± 0.03) † | 0.19 (± 0) * |
| Alanine Aminotransferase (ALT) | 145.75 (± 33.17) † | 129.675 (± 68.77) † | 88.725 (± 51.3) *,† | 94.76 (± 29.13) † | 95.475 (± 43.47) *,† | 24.45 (± 12.9) * |
| Albumin (ALB) | 2.75 (± 0.06) † | 2.85 (± 0.09) * | 2.625 (± 0.17) *,† | 3.34 (± 0.1) | 3.75 (± 0.05) * | 2.95 (± 0.51) * |
| Alkaline Phosphatase (ALP) | 131.85 (± 60.71) | 132.8 (± 41.50) * | 104.2 (± 28.58) *,† | 67.28 (± 19.89) † | 34.475 (± 24.47) *,† | 93.85 (± 0.96) |
| Cholesterol | 110.75 (± 6.45) † | 106.5 (± 3.84) * | 138.75 (± 46.98) *,† | 126.6 (± 4.32) | 141 (± 12.18) *,† | 122.25 (± 4.92) * |
| Glucose | 300.5 (± 44.52) | 261 (± 33.39) * | 247.25 (± 84.18) * | 246 (± 27.8) | 248 (± 140.05) | 259.25 (± 70.22) |
| Lactate Dehydrogenase (LDH) | 1002.75 (± 802.38) † | 684.5 (± 84.59) † | 1097.25 (± 423.92) | 375.8 (± 1336.07) † | 1196.25 (± 734.1) † | 151.25 (± 36.1) * |
| Total Protein | 4.375 (± 0.359) † | 4.725 (± 1.038) | 4.575 (± 0.45) * | 5.38 (± 0.80) | 5.675 (± 0.1) † | 5.35 (± 0.65) |

Values are expressed as mean (± SD); *: Significant to *mdx* Treated with Vehicle Only; †: Significant to Wild Type Untreated. (N=4 mice per treatment group; $p \leq 0.05$)

13Y: compound 8.

README-THROUGH COMPOUND PRODRUGS SUPPRESSING PREMATURE NONSENSE MUTATIONS

PRIOR RELATED APPLICATION

This application is the U.S. National Stage of International Patent Application No. PCT/US2015/11842, which claims the benefit of, and priority to, U.S. Provisional Application No. 61/928,334, filed Jan. 16, 2014. Each of these applications is hereby fully incorporated by reference herein.

STATEMENT REGARDING FEDERALLY SPONSORED RESEARCH OR DEVELOPMENT

This invention was made with Government support under Grant No. NS076761, awarded by the National Institutes of Health and Grant No. W81XWH-13-1-0207, awarded by the United States Army Medical Research and Materiel Command. The Government has certain rights in this invention.

FIELD

Provided herein are compounds capable of targeting nonsense mutations and therefore allowing read-through of premature termination codons. In certain embodiments, the prodrugs are conjugates of compound 5 or its pharmaceutically acceptable salts, isomers, complexes, polymorphs, hydrates or esters thereof. The prodrugs are capable of conversion by natural biological processes into an active ingredient (for example, compound 5) which can suppress early termination of protein synthesis and therefore can treat genetic diseases characterized by nonsense mutations.

Also provided herein are pharmaceutical formulations of the compounds, methods of using the compounds to treat patients afflicted with genetic disorders characterized by nonsense mutations, and methods of synthesizing the compounds.

BACKGROUND

Translation termination is signaled by three stop codons: UAA, UAG, and UGA. This mechanism is highly conserved, although each stop codon has a different efficiency for terminating translation. UGA is considered to be a "leaky" stop codon with the highest intrinsic readthrough potential. UAA shows high fidelity and little intrinsic readthrough potential, whereas UAG has intermediate fidelity (see, e.g., Weiner and Weber, 1973, *J. Mol. Biol.* 80:837-855). Nonsense mutations create primary premature termination codons (PTCs) and result in either no formation of the target protein or truncated protein with impaired stability. Large numbers of genetic disorders are caused by nonsense mutations for Which compound-induced readthrough of premature termination codons (PTCs) can be exploited as a potential treatment strategy.

Certain compounds influence the fidelity of stop codon recognition and induce readthrough of primary PTCs, which allows translation of some full-length protein. In many cases, the readthrough-induced protein is functional, even when it contains a wrongly incorporated amino acid (Keeling and Bedwell, 2005, *Curr. Pharmacogenetics* 3:259-269; Zingman et al., 2007, *Clin. Pharmacol. Ther.* 81:99-103).

It is estimated that 30% of human disease-causing alleles are nonsense mutations (Du et al., 2009, *J. Exp. Med.,* 206 (10): 2285). Other types of mutations, such as frameshift and splicing mutations, lead to secondary PTCs; however, these are not therapeutic targets for readthrough compounds (RTCs). Considering that >1,800 distinct genetic disorders are caused by nonsense mutations, the readthrough of primary PTCs has treatment potential for large numbers of patients.

To date, most reported PTC-RTCs that are active in mammalian cells have belonged to the aminoglycoside antibiotics class (Keeling and Bedwell, 2005, *Curr. Pharmacogenomics,* 3:259-269; Zingman et al., 2007, *Clin. Pharmacol. Ther.,* 81:99-103). Certain types of aminoglycosides can induce ribosomes to read through PTC mutations via insertion of a random amino acid by near-cognate transfer RNA. The therapeutic potential of aminoglycosides has been evaluated in the laboratory for different genetic models, such as cystic fibrosis (see, e.g., Du et al., 2002, *J. Mol. Med.* 80:595-604), muscular dystrophy (see, e.g., Loufrani et al., 2004, *Arterioscler. Thromb. Vasc. Biol.* 24:671-676), Hurler syndrome (Keeling et al., 2001, *Hum. Mol. Genet.* 10:291-299), cystinosis (Helip-Wooley et al., 2002, *Mol. Genet. Metab.* 75:128-133), spinal muscular atrophy (Sossi et al., 2001, *Eur. J. Hum. Genet.* 9:113-120), ataxiatelangiectasia (Lai et al., 2004, *Proc. Natl. Acad. Sci. USA.* 101:15676-15681), and type 1 Usher syndrome (Rebibo-Sabbah et al., 2007, *Hum. Genet.* 122:373-381). Clinical trials also indicate that aminoglycosides can induce some functional protein production; however, the therapeutic benefits remain uncertain (see, e.g., Politano et al., 2003, *Acta Myol.* 22:15-21). Furthermore, the toxicity of most commercial aminoglycosides in mammals has greatly diminished their potential for successful readthrough therapy (Mingeot-Leclercq and Tulkens, 1999, *Antimicrob. Agents Chemother.* 43:1003-1012; Guan et al., 2000, *Hum. Mol. Genet.* 9:1787-1793). Therefore, efforts are underway to develop better aminoglycoside derivatives with reduced toxicity and enhanced activity (Nudelman et al., 2006, *Bioorg. Med. Chem. Lett.* 16:6310-6315; Rebibo-Sabbah et al., 2007, *Hum. Genet.* 122:373-381).

Recently, PTC Therapeutics (South Plainfield, N.J.) described a more efficient non-aminoglycoside RTC, PTC124, which was developed synthetically by screening >800,000 chemicals and analogues using a luciferase-based high-throughput screening (HTS) assay (see, e.g., Welch et al., 2007, *Nature.* 447:87-91). A phase-I clinical study in cystic fibrosis confirmed that PTC124 is generally well tolerated and appears to have more efficient readthrough activity than aminoglycosides (Hirawat et al., 2007, *J. Clin. Pharmacol.* 47:430-444). Moreover, PTC124 does not induce ribosomal readthrough of normal stop codons. A phase-II clinical trial is underway (Kerem et al., 2008, *Lancet.* 372:719-727). However, a recent study indicates that the initial discovery of PTC124 by HTS can have been biased by its direct effect on the FLuc (firefly luciferase) reporter used (Auld et al., 2009, *Proc. Natl. Acad. Sci. USA.* 106:3585-3590), indicating the importance of a luciferase-independent HTS assay for future drug screening.

Recent findings have demonstrated that the specificity of the HTS utilized for the identification of the read-through compound may have been compromised by the ligand-induced stabilization of the reporter protein used for the screen (Auld, et al., (2009), *Proc. Natl. Acad. Sci.* 106, 3585-3590). Although other interpretations have been offered (Peltz et al., P (2009), *Proc. Natl. Acad. Sci. USA,* 106, E64), strong evidence have been presented in support of the post-translational activity of PTC124 (Auld et al., 2010, *Proc. Natl. Acad. Sci. USA,* 107, 4878-4883; Thorne et al., 2010, *Chem. Biol.,* 17, 646-657). Despite the off-target effects, PTC124 has been shown to suppress nonsense mutations in different disease models and has reached clinical testing in patients (Sermet-Gaudelus et al., 2010, *Am. J. Respir. Crit. Care Med., Vol.* 182, No. 10, pp. 1262-1272; Welch et al., 2007, *Nature.* 447, 87-91). However, the indeterminate efficacy of Ataluren (PTC124) in clinical trials for Duchenne boys supports the need of identifying new drugs that could be used to suppress nonsense mutations in the clinical scenario.

Recently, a sensitive and quantitative high-throughput screening method was developed by Du et al. (Du et al., 2009, *J. Exp. Med.* 206, 2285-2297) and used to screen low-molecular mass non-aminoglycoside compound libraries to identify potential drugs with PTC read-through activity. The screening protocol involved the use of a protein transcription/translation (PTT)—enzyme-linked immunosorbent assay (ELISA), using ataxia-telangiectasia (A-T) as a genetic disease model. This PTT-ELISA was driven by plasmid templates containing prototypic ATM mutations, patterned after specific disease-causing A-T (Du et al., 2009, *J. Exp. Med.* 206, 2285-2297). The screen of nearly 34,000 compounds led to the identification of compound 5 (provided in FIG. 1). This compound was shown to have biological activity in different lymphoblastoid cell lines derived from A-T patients containing each of the three types of nonsense mutations (TGA>TAA>TAG). Furthermore, compound 5 restored full-length dystrophin in mdx cells in culture (Du et al., 2009, *J. Exp. Med.* 206, 2285-2297). Altogether, these data demonstrated that the compound has read-through activity on different types of proteins, in more than one species and cell lineage, and that activity is independent of the location of the premature stop codon within the transcript. Furthermore, compound 5 was shown to not read-through normal termination codons, thus confirming specificity for PTCs (Du et al., 2009, *J. Exp. Med.* 206, 2285-2297).

We have recently demonstrated that systemic administration of compound 5 restores functional levels of dystrophin expression in skeletal muscles of the mdx mice (Kayali et al., 2012, *Hum. Mol. Genet.,* 21, 4007-4020):

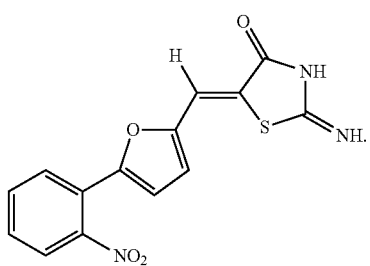

(5)

Dystrophin protein was detected in all muscle groups analyzed, including diaphragm and heart, two of the muscles most difficult muscle to target by any of the therapeutic approaches currently being developed. Dystrophin was significantly higher than that achieved by PTC124 and resulted in a significant increase in muscle strength over mice that did not receive the RTCs. The improvement in muscle function was paralleled by a decrease in creatine kinase (CK) levels a marker of muscle degeneration. These data demonstrate that compound 5 is a valid drug for the treatment of Duchenne muscular dystrophy (DMD) and suggest that many other disorders can benefit from its successful development into a drug.

However, one of the major limitations in further developing compound 5 for clinical applications is its low solubility.

SUMMARY

A successful commercialization of compound 5 is likely to require the optimization of a structure of compound 5 with improved solubility and oral viability as it is likely that oral administration is the best route to deliver the compound to target organs and at doses necessary to achieve an effect. Therefore, provided herein are compounds, compositions comprising the compounds, methods of making the compounds and compositions, and methods of using the compounds for treating or ameliorating a medical condition associated with premature termination codons (PTCs) in RNA. In certain embodiments the compounds provided herein have superior solubility, efficacy, and/or bioavailability for treating or ameliorating a medical condition associated with premature termination codons (PTCs) in RNA.

In certain embodiments, provided herein is a compound according to Formula Ia:

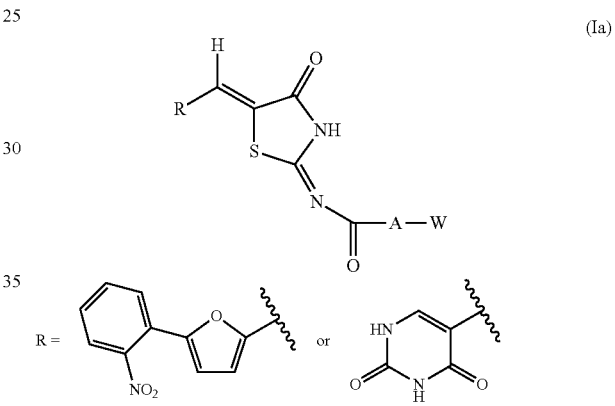

(Ia)

or a pharmaceutically acceptable salt, solvate, polymorph, hydrate, ester, isomer, stereoisomer, or tautomer thereof, wherein:

W is —NR$^a$R$^b$, —C(O)OR$^4$, —C(O)NR$^a$R$^b$, or -HetAr;
A is a bond from C(O) to W, —(CH$_2$)$_f$CH(R$^1$)(CH$_2$)$_g$—, —(CH$_2$)$_f$C(R$^a$R$^b$)(CH$_2$)$_g$—, —(CH$_2$CH$_2$O)$_h$(CH$_2$)$_t$—, —(CH$_2$)$_t$(OCH$_2$CH$_2$)$_h$—, —(CH$_2$)$_t$N(R$^e$)CH$_2$CH$_2$Z, or

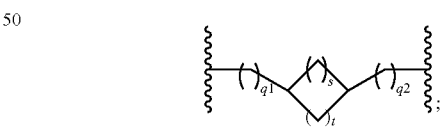

or, in the alternative, A and W combine to form

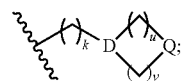

R$^1$ is —H, —(CH$_2$)$_n$CH$_3$, —CH(CH$_3$)CH$_2$CH$_3$, —CF$_3$, —CH$_2$(Ar), —CH$_2$(HetAr), —CH$_2$S(O)$_m$CH$_3$, —CH$_2$CH$_2$S(O)$_m$CH$_3$, —CH$_2$(CH$_2$)$_n$NR$^e$R$^d$, —CH$_2$OH, —CH(CH$_3$)OH, or —(CH$_2$)$_t$COOH;

R² is —H, —CH₃, —OH, or —CF₃;

each of $R^a$ and $R^b$ is independently $R^e$; or, in the alternative, $R^a$ and $R^b$, together with the nitrogen or carbon atom to which they are attached, combine to form a 4 to 7-membered ring heterocyclic ring which optionally contains additional heteroatoms selected from O, $NR^g$, and $S(O)_m$;

$R^c$ is —H, —CH₃, —(CH₂)ₙCH₃, —CH(R²)CH₃, —CH₂-pyridyl, or CH₂-imidazolyl;

$R^d$ is —H, —CH₃, or —(CH₂)ₙCH₃; or, in the alternative, $R^c$ and $R^d$, together with the nitrogen atom to which they are attached, form a 4-7 membered heterocyclic ring which optionally contains additional heteroatoms selected from O, $NR^e$, and $S(O)_m$;

each $R^e$ is independently —H, —(CH₂)ₙCH₃, —CH(CH₃)₂, —CH(CH₃)CH₂CH₃, —(CH₂CH₂O)ₚR³, or CH₂HetAr; each $R^g$ is independently —H, —(CH₂)ₙCH₃, —CH(CH₃)₂, —CH(CH₃)CH₂CH₃, —(CH₂CH₂O)ₚR³, —CH₂-phenyl or —CH₂-phenyl optionally substituted with F, Cl, —CH₃, —OCH₃, —OCF₃, or HetAr;

each R³ is independently —H, —CH₃, —OH, or —CF₃; alternatively, each R³ is independently —H, —CH₃, —CH₂CH₂—OH, or —CF₃;

each R⁴ is independently —H or —(CH₂)ₙNR^cR^d;

each HetAr is independently a heteroaryl group optionally selected from pyridyl, pyrimidyl, C-imidazolyl and N-imidazolyl;

D is CH or N;

Q is —O—, —NR^a—, —S(O)_m—, or —CH—W—;

each k is independently 1, 2, 3 or 4;
each u is independently 1, 2 or 3;
each v is independently 1, 2 or 3;
each p is independently 1 or 2;
each f is independently 0, 1 or 2;
each g is independently 0, 1 or 2;
each h is independently 1 or 2;
each n is independently 0, 1, 2, 3, or 4;
each m is independently 0, 1 or 2;
each of q₁ and q₂ is independently 0, 1, 2 or 3;
each s is independently 0, 1, 2 or 3; and
each t is independently 0, 1, 2 or 3.

In certain embodiments provided herein is a composition. The composition comprises at least one compound or a pharmaceutically acceptable salt or prodrug thereof in an amount effective for treating or ameliorating a medical condition associated with premature termination codons (PTCs) in RNA, as described herein.

In some embodiments of the composition, the composition comprises two compounds, each of the two compounds described herein.

In some embodiments of the compositions provided herein, the composition further comprises a pharmaceutically acceptable carrier.

In some embodiments of the compositions provided herein, the composition is formulated in a formulation for local or systemic delivery. Examples of such formulations are formulations for oral administration, injection, topical administration, pulmonary administration, or implant.

In still a further aspect, it is provided a method. The method comprises providing a compound having the ability to read through premature termination codons (PTCs) in RNA, and forming a composition comprising the compound, a pharmaceutically acceptable salt thereof, or a prodrug thereof. The compound is described herein.

In some embodiments of the method, the composition comprises two compounds, each of the two compounds described herein.

In some embodiments of the methods described herein, the composition further comprises a pharmaceutically acceptable carrier.

In some embodiments of the methods described herein, the composition is formulated in a formulation for local or systemic delivery. Examples of such formulations are formulations for oral administration, injection, topical administration, pulmonary administration, or implant.

In certain embodiments provided herein is a method of treating or ameliorating a medical condition associated with premature termination codons (PTCs) in RNA. The method comprises administering to a subject a compound described herein or a composition described herein.

BRIEF DESCRIPTION OF THE DRAWINGS

FIG. 1 provides the structure of (Z)-2-imino-5-((5-(2-nitrophenyl)furan-2-yl)methylene)thiazolidin-4-one, compound 5.

FIG. 2 provides a plots showing distribution of compound 5 in mdx mice after systemic administration. Pharmacokinetics and biodistribution of compound 5 after intravenous (IV) and intraperitoneal (IP) injections. Injections were performed at a concentration of 5 mg/kg and of 30 mg/kg for the IV and IP injection respectively. The predicted effective dose of the parent compound has been computed to be 2 mg/kg.

FIG. 3 provides a plot showing distribution of compound 5 in mdx mice after systemic administration. Oral administration of compound 5 was performed at a dose of 60 mg/kg. The distribution of the compound was assessed 60 min after oral gavage (OG) and compared to that achieved after IV injection administered at a dose of 5 mg/kg or IP injection given at a dose of 30 mg/kg.

FIG. 4 provides an exemplary chemical structure of prodrugs of compound 5. The derivatives contain a linker (R1) which can be identical for all analogs and a second group which can differs from prodrug to prodrug. The derivatives are designed to increase the solubility of the parent compound and improve its absorption. Groups R2 through R7 represent 6 possible structures that are conjugated to the linker to produce 6 different prodrugs. The predicted site of cleavage in the liver is shown by the red arrow.

FIG. 5 provides a plot showing microsomal stability assay results in liver extracts. Compounds (5 μg) were incubated at 37° C. in fresh liver homogenate (125 mg) isolated from C57 mice in the presence of NADPH (2 mM).

FIG. 6 provides plots showing rate of conversion of prodrug into parent drug (compound 5) in liver extract. Compounds (5 μg) were incubated at 37° C. in fresh liver homogenate (125 mg) isolated from C57 mice in the presence of NADPH (2 mM). Conversion of the prodrugs into the parent compound was detected in all samples analyzed as early as 1 min after incubation.

FIG. 7 provides plots showing dystrophin expression in mdx myotubes. Panel (A) provides a plot showing muscle cells isolated from mdx mouse which were induced to differentiate for 16 hrs and then exposed to the compounds for an additional 80 hrs prior to protein analysis. Dystrophin was detected by Western blot analysis in all cells treated with the prodrugs but not in cells exposed to DMSO or in untreated mdx myotubes. As positive control, protein isolated from wild type myotubes maintained in differentiation media for the same period of time (corresponding to 5% of total protein) were mixed with proteins isolated from untreated mdx. Equal loading was confirmed by Western blot using α-actinin as internal control. Panel (B) provides plots showing quantitative analysis of protein levels obtained from multiple independent experiments and showed a dose response increase in dystrophin expression in all compounds tested. (†: significant to compound 5-2 μM; §: significant to compound 5-10 μM; *≤0.03; **≤0.002)

FIG. 8 provides plots showing dystrophin expression after intramuscular injection. Panel (A) provides plots showing dystrophin staining in TA muscles of mdx mice injected with RTC13 or its derivatives and analyzed two weeks after delivery of compounds and compared to muscles treated with DMSO alone. Dystrophin expression was evident in muscles that received the compounds but not in sham-injected muscles. Weak expression was detected in TA muscles injected with gentamicin and RTC14. (N=4 muscles per compound; scale bar: 50 μm). Panel (B) provides plots showing the number of dystrophin positive fibers determined across the length of the muscle. TA injected with compound 5 showed a significantly higher number of positive fibers than muscles that received compounds 16 and 20. No significant differences were detected in muscles that received compound 5 when compared to muscles that received compounds 12 and 8. Shown here is the average number of dystrophin positive fibers per cross-sectional area containing the highest number of positives. (N=4 muscles per compound; *: p=0.0008; **: p≤0.04).

FIG. 9 provides a plot showing the rate of conversion of prodrugs into parent drug (compound 5) in muscle in vivo. Prodrugs were injected into Tibialis Anterior and muscles were isolated 24 hrs after intramuscular injection.

FIG. 10 provides a plot showing pharmacokinetic studies in mdx mice after oral administration of compound 12 in liver and kidney. The compound was administered at a dose of 60 mg/kg in 6-8 weeks old C57 BL/10 mice and tissues were analyzed after oral administration at the time points indicated.

FIG. 11 provides plots showing the results of pharmacokinetics studies in mdx mice after oral administration of compound 12 in muscle. The compound was administered at a dose of 60 mg/kg in 6-8 weeks old C57 BL/10 mice and tissues were analyzed after oral administration at the time points indicated.

FIG. 12 provides plots showing the results of pharmacokinetics studies in mdx mice after oral administration of compound 8. The compound was administered at a dose of 60 mg/kg in 6-8 weeks old C57 BL/10 mice and tissues were analyzed 60 min after oral administration.

FIG. 13 provides plots showing the results of pharmacokinetics studies in C57BL/10 mice after oral administration of compound 8 in plasma. The compound was administered at the indicated dosages in 6-8 weeks old C57BL/10 mice and tissues were analyzed in plasma 15 min, 30 min, 1 hr, 4 hrs, 6 hrs, and 24 hrs after gavage.

FIG. 14 provides plots showing the results of pharmacokinetics studies in C57BL/10 mice after oral administration of compound 8 in whole blood. The compound was administered at the indicated dosages in 6-8 weeks old C57BL/10 mice and tissues were analyzed in whole blood 15 min, 30 min, 1 hr, 4 hrs, 6 hrs, and 24 hrs after gavage.

FIG. 15 provides plots showing the results of pharmacokinetics studies in C57BL/10 mice after oral administration of compound 8 in liver. The compound was administered at the indicated dosages in 6-8 weeks old C57BL/10 mice and tissues were analyzed in liver 15 min, 30 min, 1 hr, 4 hrs, 6 hrs and 24 hrs after gavage.

FIG. 16 provides plots showing the results of pharmacokinetics studies in C57BL/10 mice after oral administration of compound 8 in kidney. The compound was administered at the indicated dosages in 6-8 weeks old C57BL/10 mice and tissues were analyzed in kidney 15 min, 30 min, 1 hr, 4 hrs, 6 hrs and 24 hrs after gavage.

FIG. 17 provides plots showing the results of pharmacokinetics studies in C57BL/10 mice after oral administration of compound 8 in quadriceps. The compound was administered at the indicated dosages in 6-8 weeks old C57BL/10 mice and tissues were analyzed in quadriceps 15 min, 30 min, 1 hr, 4 hrs, 6 hrs, and 24 hrs after gavage.

FIG. 18 provides plots showing the results of pharmacokinetics studies in C57BL/10 mice after oral administration of compound 8 in diaphragm. The compound was administered at the indicated dosages in 6-8 weeks old C57BL/10 mice and tissues were analyzed in diaphragm 15 min, 30 min, 1 hr, 4 hrs, 6 hrs, and 24 hrs after gavage.

FIG. 19 provides plots showing the results of pharmacokinetics studies in C57BL/10 mice after oral administration of compound 8 in gastrocnemius. The compound was administered at the indicated dosages in 6-8 weeks old C57BL/10 mice and tissues were analyzed in gastrocnemius 15 min, 30 min, 1 hr, 4 hrs, 6 hrs, and 24 hrs after gavage. Compound 8 and RTC13 (compound 5) were not detected in muscles isolated from mice that received compound 8 at a dose of 10 mg/kg.

FIG. 20 provides plots showing the results of pharmacokinetics studies in C57BL/10 mice after oral administration of compound 8 in biceps. The compound was administered at the indicated dosages in 6-8 weeks old C57BL/10 mice and tissues were analyzed in biceps 15 min, 30 min, 1 hr, 4 hrs, 6 hrs and 24 hrs after gavage. Compound 8 and RTC13 (compound 5) were not detected in muscles isolated from mice that received compound 8 at a dose of 10 mg/kg.

FIG. 21 provides plots showing the results of pharmacokinetics studies in C57BL/10 mice after oral administration of compound 8 in heart. The compound was administered at the indicated dosages in 6-8 weeks old C57BL/10 mice and tissues were analyzed in heart 15 min, 30 min, 1 hr, 4 hrs, 6 hrs, and 24 hrs after gavage. Compound 8 and RTC13 (compound 5) were not detected in muscles isolated from mice that received compound 8 at a dose of 10 mg/kg and 30 mg/kg.

FIG. 22 provides plots showing the weight of mdx mice after oral administration of compound 8 for up to one month. The compound was administered in 6-8 weeks old mdx and C57BL/10 mice three times per day at the indicated dosages and weight was recorded daily.

FIG. 23 provides images of microscopic images obtained from muscles isolated from mdx mice after oral administration of compound 8. Compounds were administered in 6-8 weeks old mdx mice three times per day for one month at the indicated dosages. Dystrophin expression was evident in muscles that received the compounds but not in sham-injected muscles. Muscles isolated from mice that received compound 8 at a dose of 30 mg/kg or 60 mg/kg showed higher levels of dystrophin expression than muscles obtained from mdx mice treated with PTC124 (N=6 muscles per treatment group; scale bar: 100 μm).

FIG. 24 provides plots showing functional improvement in mdx mice after oral administration of compound 8 for up to one month. Panel (A) provides plots showing the forelimb grip test that was used to assess the effects of systemic administration of RTCs on muscle strength. A significant force recovery was detected in mdx mice treated with compound 8 compared to sham-injected control mice and mice that received PTC124. Muscle strength remained significantly lower than that detected in wild type mice. No significant improvements were detected in mice that received PTC124 compared to untreated mice. (N=5 mice per treatment group; *p<0.05; **p<0.005). Panel (B) provides plots showing the results obtained using the wire test. The average hanging time of mice that received compound 8 was significant than that of sham-injected mice or mice treated with PTC124. No significant improvements were detected in mice that received PTC124 compared to untreated mice. (N=6 mice per treatment group; *p<0.05; **p=0.005).

FIG. 25 provides plots showing in vitro force measurement of diaphragm muscles of mdx mice treated with vehicle, compound 8 at a dose of 30 mg/kg or compound 8 at a dose of 60 mg/kg three times per day at intervals of 4 hrs for up to one month. Muscles isolated from untreated and treated mice muscles were subjected to a series of five eccentric contractions with a 5-min rest between contractions. Results were compared to those of wild type (C57BL/10) mice. Panel (A) provides plots showing the decrease in force (in percentage) obtaining following eccentric contractions over the course of the analyses. An improvement if loss of force was detected in mice that received compound 8 at a dose of 30 mg/kg and 60 mg/kg). Plot (B) show the results of the decrement in force (in percentage) obtained in mice treated with compound 8. The decrement was significantly lower in mice that received compound 8 at a dose of 60 mg/kg compared to mice that received vehicle only. (N=4 mice per treatment group, *:p≤0.05; **:p≤0.03).

FIG. 26 Table 2 provides the results of the serum chemistry analyses of mdx mice treated with vehicle, PTC124 at a dose of 30 mg/kg, PTC124 at a dose of 60 mg/kg, compound 8 at a dose of 30 mg/kg or compound 8 at a dose of 60 mg/kg three times per day at intervals of 4 hrs for up to one month. The serum levels of albumin, alkaline phosphatase (ALP), total bilirubin, lactate dehydrogenase (LDH), cholesterol, total protein, and glucose were within normal range. Mice that received compound 8 showed a decrease in blood urea nitrogen (BUN), alanine aminotransferase (ALT) and creatinine when compared to mice that received vehicle alone. Values are expressed as mean plus or minus Standard Deviation (±SD). The symbol * indicates statistical significance compared to mdx treated with vehicle only. The symbol † indicates statistical significance compared to wild type (C57BL/10) untreated mice. (N=4 mice per treatment group; p≤0.05)

DETAILED DESCRIPTION

Compounds

In an embodiment, provided herein is a compound which is a prodrug of the following compound 5 or 101:

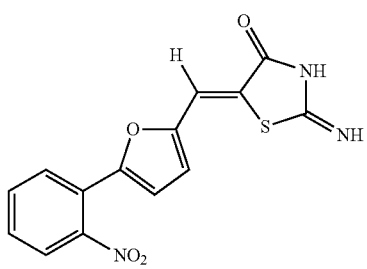
(5)

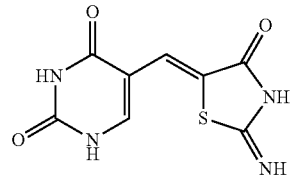
(101)

or a pharmaceutically acceptable salt, solvate, polymorph, hydrate, ester, isomer, stereoisomer, or tautomer thereof.

In an embodiment, provided herein is a compound which is an acyl derivative of the following compound 5 or 101:

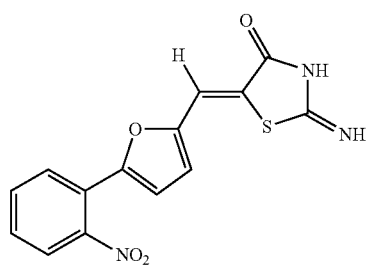
(5)

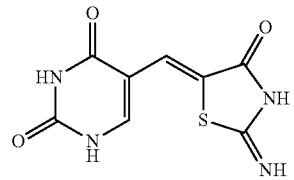
(101)

or a pharmaceutically acceptable salt, solvate, polymorph, hydrate, ester, isomer, stereoisomer, or tautomer thereof.

In an embodiment, provided herein is a compound which is a prodrug of the following compound 5:

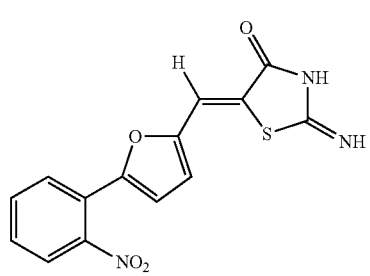
(5)

or a pharmaceutically acceptable salt, solvate, polymorph, hydrate, ester, isomer, stereoisomer, or tautomer thereof.

In an embodiment, provided herein is a compound which is an acyl derivative of the following compound 5:

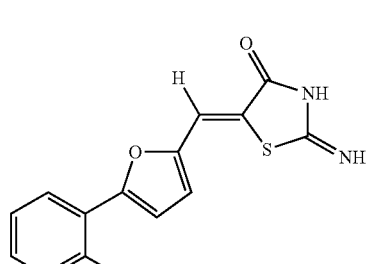
(5)

or a pharmaceutically acceptable salt, solvate, polymorph, hydrate, ester, isomer, stereoisomer, or tautomer thereof.

In an embodiment, provided herein is a compound which is a prodrug of the following compound 101:

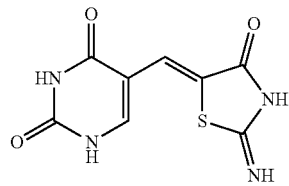
(101)

or a pharmaceutically acceptable salt, solvate, polymorph, hydrate, ester, isomer, stereoisomer, or tautomer thereof.

In an embodiment, provided herein is a compound which is an acyl derivative of the following compound 101:

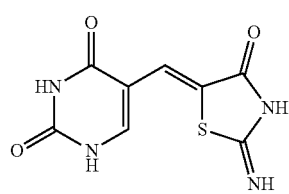
(101)

or a pharmaceutically acceptable salt, solvate, polymorph, hydrate, ester, isomer, stereoisomer, or tautomer thereof.

In an embodiment, provided herein is compound according to Formula Ia:

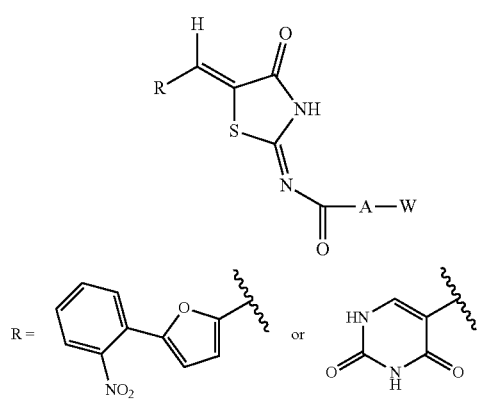
(Ia)

or a pharmaceutically acceptable salt, solvate, polymorph, hydrate, ester, isomer, stereoisomer, or tautomer thereof, wherein: W is —$NR^aR^b$, —$C(O)OR^4$, —$C(O)NR^aR^b$, or -HetAr; A is a bond from C(O) to W, —$(CH_2)_f CH(R^1)(CH_2)_g$—, —$(CH_2)_f C(R^aR^b)(CH_2)_g$—, —$(CH_2CH_2O)_h(CH_2)_t$—, —$(CH_2)_t(OCH_2CH_2)_h$—, —$(CH_2)_t N(R^e)CH_2CH_2Z$, or

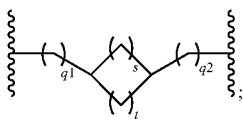

or, in the alternative, A and W combine to form

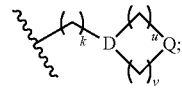

$R^1$ is —H, —$(CH_2)_n CH_3$, —$CH(CH_3)CH_2CH_3$, —$CF_3$, —$CH_2(Ar)$, —$CH_2(HetAr)$, —$CH_2S(O)_m CH_3$, —$CH_2CH_2S(O)_m CH_3$, —$CH_2(CH_2)_n NR^cR^d$, —$CH_2OH$, —$CH(CH_3)OH$, or —$(CH_2)_f COOH$; $R^2$ is —H, —$CH_3$, —OH, or —$CF_3$; each of $R^a$ and $R^b$ is independently $R^e$; or, in the alternative, $R^a$ and $R^b$, together with the nitrogen or carbon atom to which they are attached, combine to form a 4 to 7-membered ring heterocyclic ring which optionally contains additional heteroatoms selected from O, $NR^g$, and $S(O)m$; $R^c$ is —H, —$CH_3$, —$(CH_2)_n CH_3$, —$CH(R^2)CH_3$, —$CH_2$-pyridyl, or $CH_2$-imidazolyl; $R^d$ is —H, —$CH_3$, or —$(CH_2)_n CH_3$; or, in the alternative, $R^c$ and $R^d$, together with the nitrogen atom to which they are attached, form a 4-7 membered heterocyclic ring which optionally contains additional heteroatoms selected from O, $NR^e$, and $S(O)_m$; each $R^e$ is independently —H, —$(CH_2)_n CH_3$, —$CH(CH_3)_2$, —$CH(CH_3)CH_2CH_3$, —$(CH_2CH_2O)_p R^3$, or $CH_2HetAr$; each $R^g$ is independently —H, —$(CH_2)_n CH_3$, —$CH(CH_3)_2$, —$CH(CH_3)CH_2CH_3$, —$(CH_2CH_2O)_p R^3$, —$CH_2$-phenyl or —$CH_2$-phenyl optionally substituted with F, Cl, —$CH_3$, —$OCH_3$, —$OCF_3$, or HetAr; each $R^3$ is independently —H, —$CH_3$, —OH, or —$CF_3$; or, alternatively, each $R^3$ is independently —H, —$CH_3$, —$CH_2CH_2$—OH, or —$CF_3$; each $R^4$ is independently —H or —$(CH_2)_n NR^cR^d$; each HetAr is independently a heteroaryl group optionally selected from pyridyl, pyrimidyl, C-imidazolyl and N-imidazolyl; D is CH or N; Q is —O—, —$NR^a$—, —$S(O)_m$—, or —CHW—; each k is independently 1, 2, 3 or 4; each u is independently 1, 2 or 3; each v is independently 1, 2 or 3; each p is independently 1 or 2; each f is independently 0, 1 or 2; each g is independently 0, 1 or 2; each h is independently 1 or 2; each n is independently 0, 1, 2, 3, or 4; each m is independently 0, 1 or 2; each of $q_1$ and $q_2$ is independently 0, 1, 2 or 3; each s is independently 0, 1, 2 or 3; and each t is independently 0, 1, 2 or 3. In certain embodiments, compounds according to Formula Ia are provided with the proviso that when D is CH, then Q is not —O—. In certain embodiments, compounds according to Formula Ia are provided with the proviso that when D is N and Q is —$NR^a$—, then u and v are not both equal to 1. In certain embodiments, compounds according to Formula Ia are provided with the proviso that when D is N and Q is —$NR^a$—, —O—, or —$S(O)_m$—, then u and v are not both equal to 1. In embodiments of Formula Ia when A is

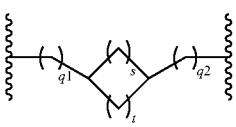

and s and t are both 0, then A is

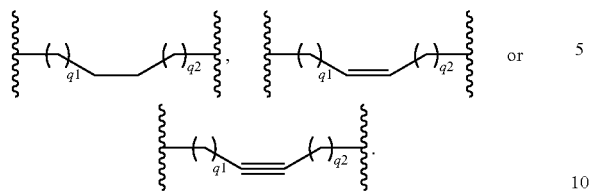

In an embodiment, provided herein is a compound of Formula Ia according to Formula Ib:

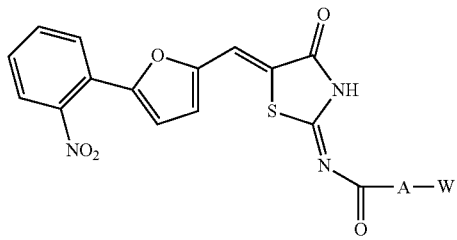

(Ib)

or a pharmaceutically acceptable salt, solvate, polymorph, hydrate, ester, isomer, stereoisomer, or tautomer thereof, where A and W are as described in the context of Formula Ia.

In an embodiment, provided herein is a compound of Formula Ia according to Formula II:

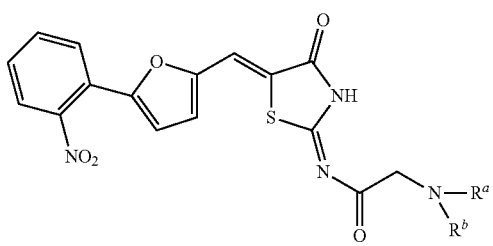

(II)

or a pharmaceutically acceptable salt, solvate, polymorph, hydrate, ester, isomer, stereoisomer, or tautomer thereof and where $R^a$ and $R^b$ are as described in the context of Formula Ia.

In an embodiment, provided herein is a compound of Formula Ia according to Formula III:

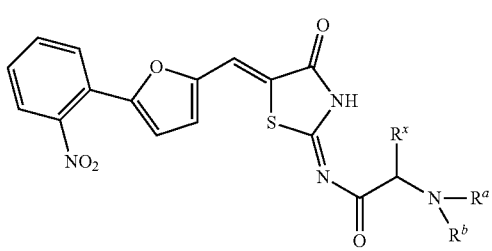

(III)

or a pharmaceutically acceptable salt, solvate, polymorph, hydrate, ester, isomer, stereoisomer, or tautomer thereof, where $R^a$ and $R^b$ are as described in the context of Formula Ia and wherein $R^x$ is a side chain of a naturally occurring amino acid, or $R^x$ is —CH₃, -iPr, —CH₂NH₂, —CH₂CH₂NH₂, —CH₂CH₂CH₂NH₂, —CH₂COOH, —CH₂CH₂COOH,

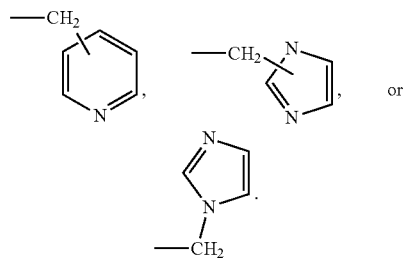

In an embodiment, provided herein is compound of Formula Ia according to Formula IV:

(IV)

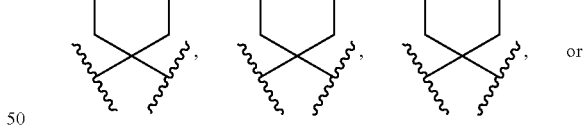

or a pharmaceutically acceptable salt, solvate, polymorph, hydrate, ester, isomer, stereoisomer, or tautomer thereof, where $R^a$ and $R^b$ are as described in the context of Formula Ia and wherein ring G is a 5 to 6-membered heterocyclic ring. In an embodiment, provided herein is a compound according to Formula IV, wherein ring G is

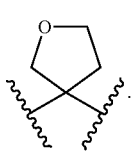

In an embodiment, provided herein is a compound of Formula Ia according to Formula V:

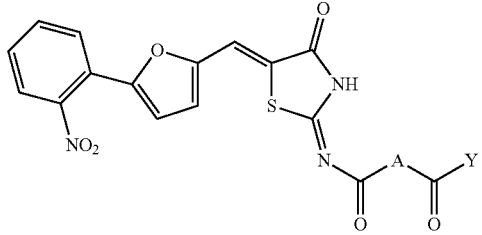

(V)

or a pharmaceutically acceptable salt, solvate, polymorph, hydrate, ester, isomer, stereoisomer, or tautomer thereof, wherein Y is —$OR^4$ or —$NR^aR^b$ and where A, $R^4$, $R^a$ and $R^b$ are as described in the context of Formula Ia.

In an embodiment, provided herein is a compound according to any of Formulas I-V, wherein —$NR^aR^b$ is —$NH_2$, —$NHCH_3$, —$N(CH_3)_2$,

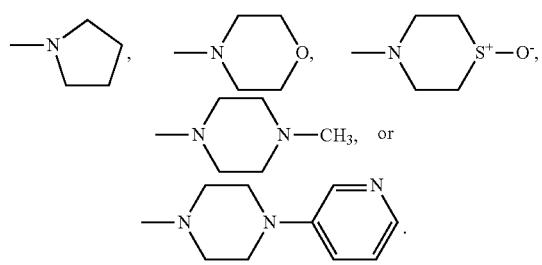

In an embodiment, provided herein as a compound according to any of Formulas I-V wherein —$NR^aR^b$ is —$NH_2$, —$NHCH_3$, —$N(CH_3)_2$,

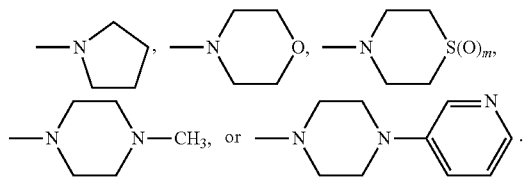

In an embodiment, provided herein is a compound according to any of Formulas I-V, wherein A is —$(CH_2)_f$—$CH(R^1)(CH_2)_g$—, where $R^1$, f and g are as described in the context of Formula Ia.

In an embodiment, provided herein is a compound of any of Formulas I-V, wherein W is HetAr.

In an embodiment, provided herein is a compound of any of Formulas I-V, wherein A is

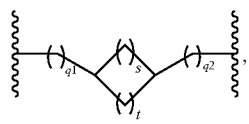

where $q_1$, $q_2$, s and t are as described in the context of Formula Ia. In an embodiment, provided herein is a compound of any of Formulas I-V, wherein A is —$(CH_2CH_2O)_h$ $(CH_2)_t$— or —$(CH_2)_t(OCH_2CH_2)_h$—, and h and t are as described in the context of Formula Ia.

In an embodiment, provided herein is a compound of Formula Ia according to Formula VI:

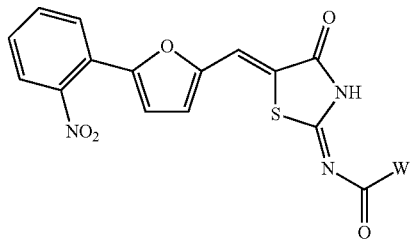

(VI)

or a pharmaceutically acceptable salt, solvate, polymorph, hydrate, ester, isomer, stereoisomer, or tautomer thereof, where W is as described in the context of Formula Ia.

In an embodiment, provided herein is a compound of any of Formulas I-VI, wherein A and W combine to form

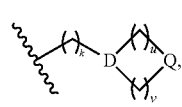

where D, Q, k, u and v are as described in the context of Formula Ia.

In an embodiment, provided herein is a compound according to any of the following formulas:

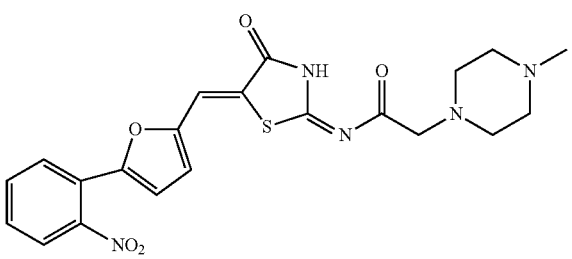

(8)

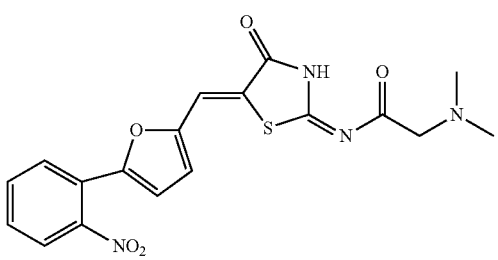

(12)

(16)

[Structure 16: furan-phenyl-NO2 with thiazolidinone linked via C(=N)–NH–C(O)– to piperidine-4-yl (NH)]

(20)

[Structure 20: furan-phenyl-NO2 with thiazolidinone linked via C(=N)–N–C(O)–CH2–morpholine]

(22)

[Structure 22: furan-phenyl-NO2 with thiazolidinone linked via C(=N)–NH–C(O)–CH(CH3)–NH–C(O)–O-tBu]

or a pharmaceutically acceptable salt, solvate, polymorph, hydrate, ester, isomer, stereoisomer, or tautomer thereof.

In certain embodiments, provided herein are:

(i) compounds as described herein, for example of Formula I-VI, 8, 12, 16, 20 or 22, provided as a pharmaceutically acceptable salt; and (ii) pharmaceutical compositions comprising: a compound as described herein, for example of Formula I-VI, 8, 12, 16, 20 or 22, or a pharmaceutically acceptable salt thereof, in an amount effective for treating or ameliorating a medical condition associated with premature termination codons (PTCs) in RNA; and a pharmaceutically acceptable excipient or pharmaceutically acceptable carrier.

In an embodiment, provided herein are compounds according to Formula Ia, wherein —C(O)-A-W combine to form:

(i)

$$OC-CH_2-NRaRb$$

(f = j = 0, zero)

NRaRb = NH2, NHCH3, N(CH3)2,

—N-pyrrolidine, —N-morpholine, —N-thiomorpholine S-oxide,
—N-piperazine-N-CH3, —N-piperazine-N-(2-pyridyl)

(ii)

$$OC-CH(Rx)-NRaRb$$

(f = j = 0, zero)

Rx = side chain of amino acids: CH3, iPr, CH2NH2, CH2CH2—NH2, CH2CH2CH2—NH2, CH2COOH, CH2CH2—COOH, and

[H2C-pyridyl], [H2C-imidazolyl (N-linked via CH2)], [imidazolyl-CH2]

(iii)

$$OC-C(Ra)(Rb)-NRaRb$$

(f = j = 0, zero)

[4-N(CH3)2-tetrahydropyran-4-yl], [4-N(CH3)2-4-methoxy-tetrahydropyran], [4-N(CH3)2-thiane S-oxide], [3-N(CH3)2-tetrahydrofuran-3-yl]

(iv)

$$OC-C(Ra)(Rb)-CO_2-R'$$   $$OC_f(H_2C)-C(Ra)(Rb)-(CH_2)_g-W$$

(f = j = 0, zero)
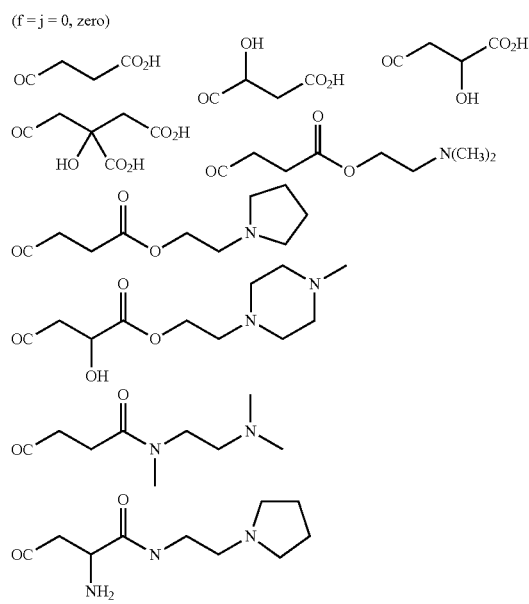
W=NRaRb =
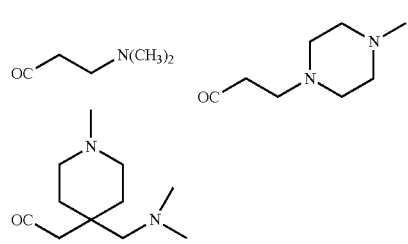
W=HetAr =
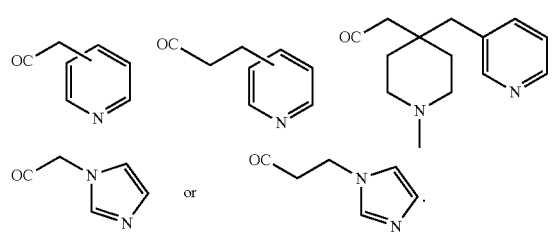
In an embodiment, provided herein are compounds according to Formula I, wherein —C(O)-A-W combine to form:
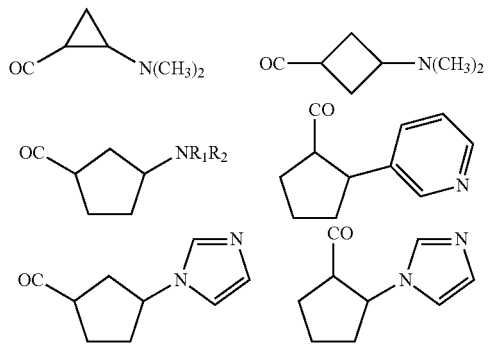
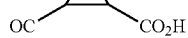
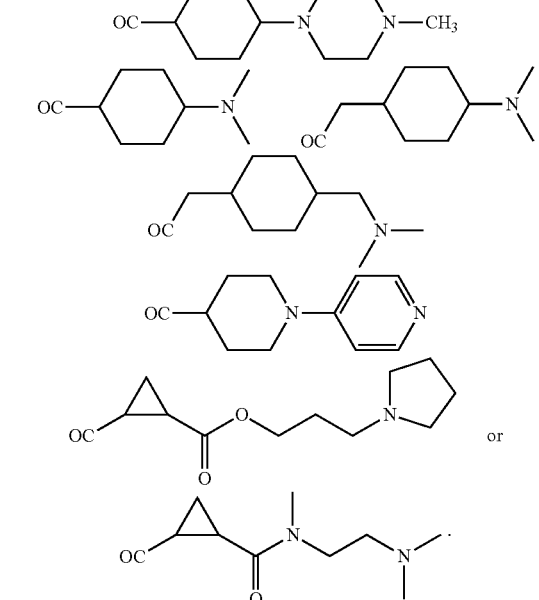
R1 = H, CH3, CH2—CH2—OH, —CH2CH2—N(CH3)2, —CH2—Py, —CH2—(C-Imidazole), —CH2CH2—N(Imidazole)
In an embodiment, provided herein are compounds according to Formula I, wherein —C(O)-A-W combine to form:
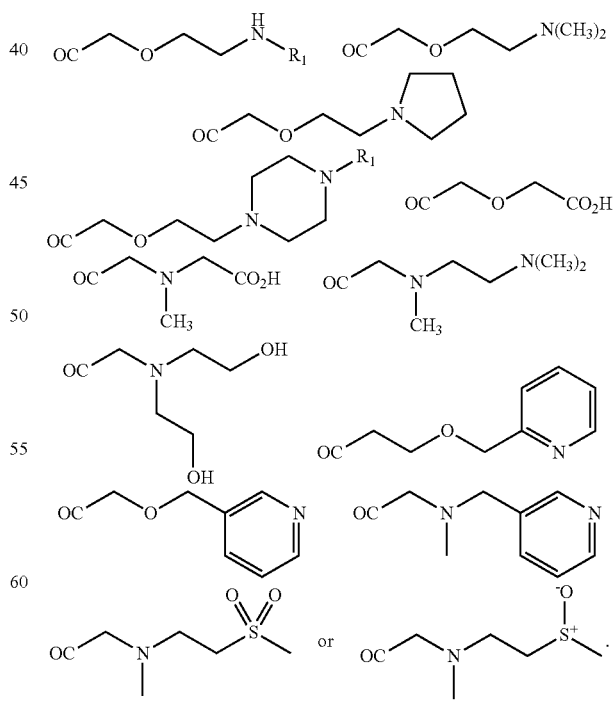
R1 = H, CH3, CH2—CH2—OH, —CH2CH2—N(CH3)2, —Py, —CH2—Py, —CH2-(C-Imidazole), —CH2CH2-N(Imidazole)

In an embodiment, provided herein are compounds according to Formula I, wherein —C(O)-A-W combine to form:

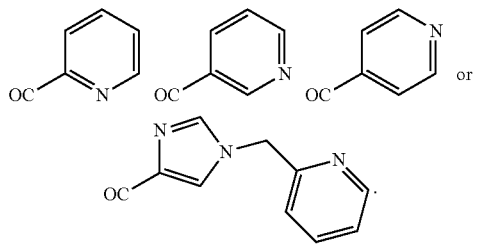

In an embodiment, provided herein are compounds according to Formula I, wherein —C(O)-A-W combine to form:

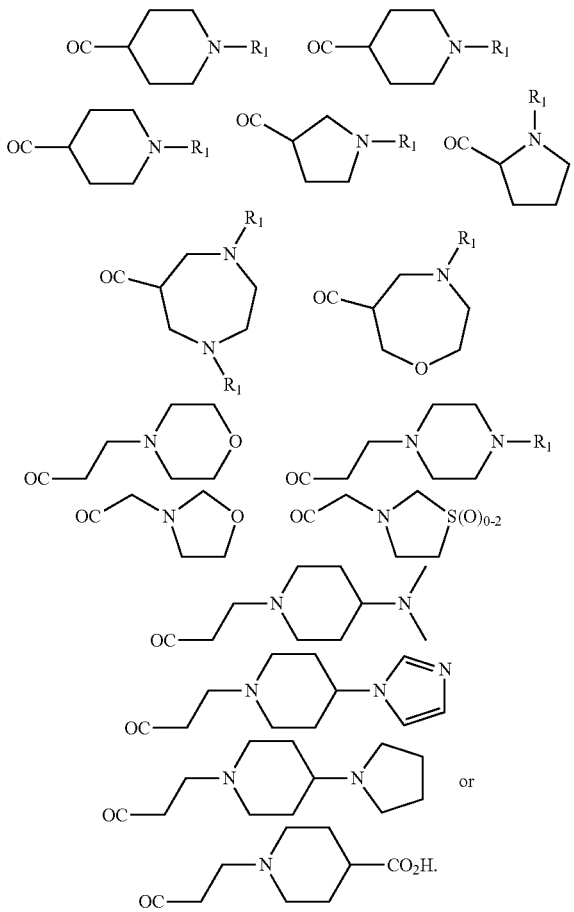

R1 = H, CH3, CH2—CH2—OH, —CH2CH2—N(CH3)2, —Py, —CH2—Py, —CH2-(C-Imidazole), —CH2CH2-N(Imidazole)

Methods of Making

Compounds provided herein can be readily prepared according to established methodology in the art of organic synthesis. Several General Synthetic Methods for preparation of compounds described herein are provided.

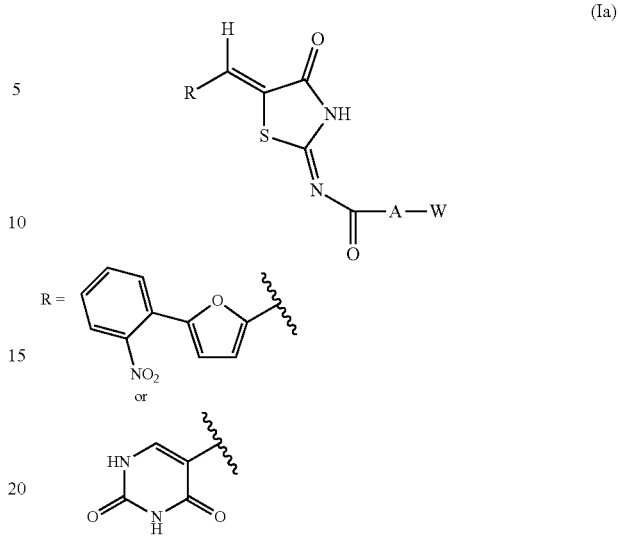

Synthesis of the compounds with the Formula Ia are prepared essentially by acylation of the imino-thiazolidinone G2. The 5-aryl/heteroaryl-2-imino-1,3-thiazolidin-4-one derivatives (G2) can be prepared by reaction of an appropriate aryl/heteroaryl aldehyde G3 with 2-imino-1,3-thiazolidin-4-one (G4) as shown in scheme 1. The aryl/heteroaryl aldehydes can be purchased from commercial sources or prepared following literature reports. Some of these reports include the method described by Jung et al. (*Bioorg. Med. Chem. Lett.* 21 (2011) 5842-5848); and some selective derivatives can be prepared as reported by Chiacchio et al. (*Tetrahedron*, 59 (2003) 4733-4738) or as shown in Specific Example 1 or alternatively by variations of these, and related, reported methods.

Scheme 1. General route to 5-(aryl/heterocyclic)ene-2-imino-1,3-thiazolidin-4-one (G2)

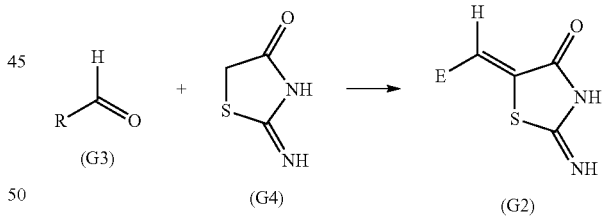

Reaction of an appropriately protected acid (G5), which is bearing a basic or an acidic functionality that would ultimately allow salt formation, with G2 using a variety of peptide coupling reagents provide the protected derivatives G6. The —COOH or the primary/secondary amino functionality in G5 are preferably protected with an acid labile protecting group such as tert-butyl ester or BOC—, respectively. An array of coupling reagents are available commercially. Some of these include a carbodiimide (EDCI, DCC etc.) with added coupling enhancers such as HOBt, HOAt or alternatively using TBTU, HBTU. Alternatively, the carboxylic acid can be converted to an activated acyl derivative such as acid chloride, acid fluoride, or an active ester such as acylimidazolide or succinamide esters, prior to reaction with G2. If the acyl derivative G6 contains an acid labile protecting group (e.g. —O-tert-butyl or N—BOC), treatment with an acid such as HCl in an organic solvent (MTBE, methyl-tert-butyl ether, THF, p-dioxane, EtOAC, or Et2O) provides the corresponding hydrochloride salt of the amine or the free carboxylic acid containing compound G7. The amine-salt forms can be exchanged to an alternate salt form or the —COOH can be converted to the carboxylate salt form using an appropriate anion or cation ion-exchange resin, respectively.

Scheme 2. Preparation of acyl-imino derivative G6

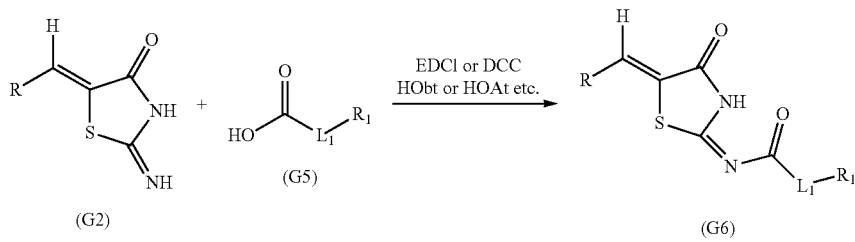

R1 = CO2tBu
or NH—BOC
or N(R)BOC
or N(R'R")

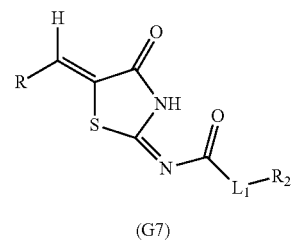

(G7)

R2 = CO2H
or NH2•HCl
or NH(R)•HX
or N(R'R")•HCl

Alternatively, the acid G5 can be converted to either a mixed anhydride (G8) or a symmetrical anhydride and subsequently reacted with the imino derivative G2 to provide acylimino compounds G6 (Scheme 3).

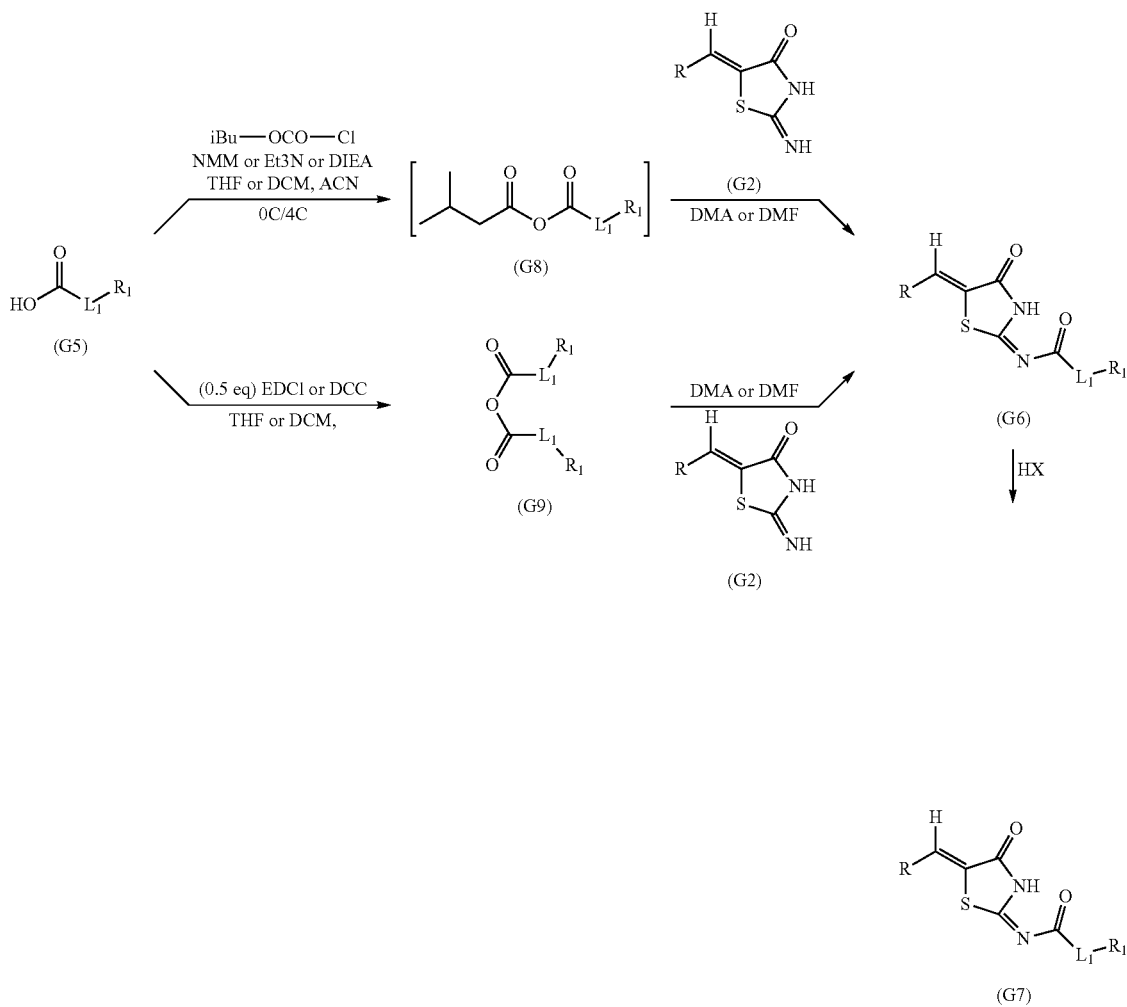

Scheme 3.

R2 = CO2H
 or NH2•HCl
 or NH(R)•HX
 or N(R'R")•HCl

The dicarboxylic acids (G10) can be converted to the anhydride (G11) which can be reacted directly with G2 to provide acylimino derivatives G12 (Scheme 4), and these can then be reacted with, for example, an ethanolamine derivative to introduce a tertiary amine on to G12, if desired. Otherwise, the anhydride G11 can be converted to the mono-acid monoester derivative G13, which can then be reacted with G2 as shown in scheme 2 or 3.

Scheme 4.

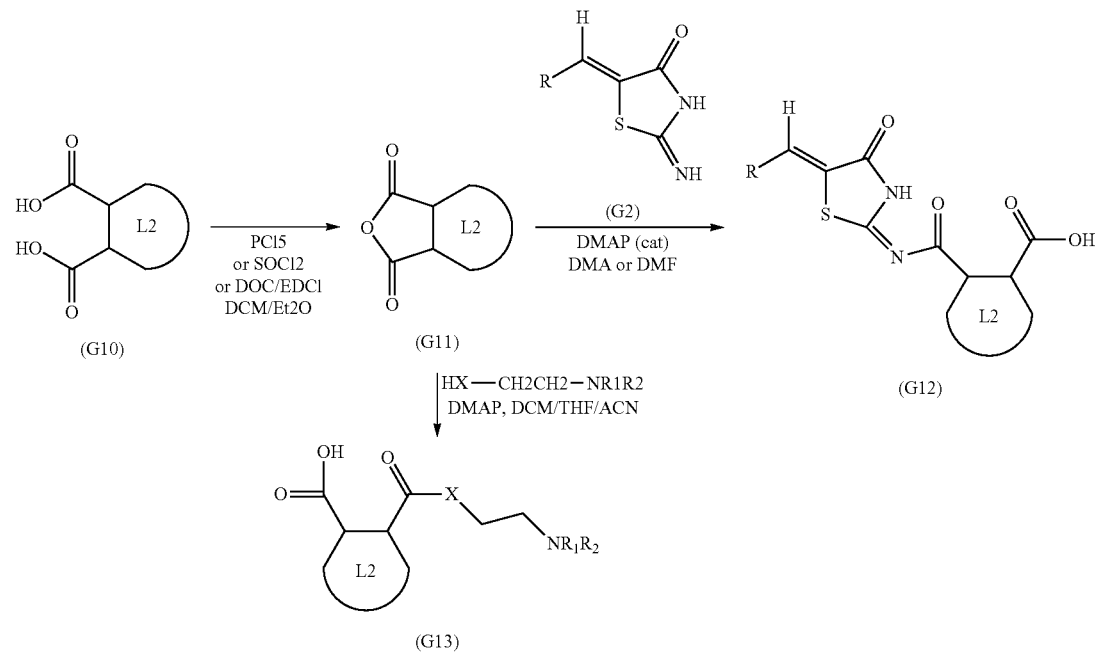

X = O, NH,
N(R) {e.g.
N(CH3)}

A wide variation of acids bearing diverse functionalities and structural variations at L1 are commercially available, or such desired inputs can be prepared by numerous methods reported in the art. For example, reaction on a secondary amine (G14) with a halide G15/G19 (scheme 5 and 6) or corresponding cycloalkyl/heterocyclic-keto-ester G22/G23 via reductive amination (scheme 5) would allow access to such acid derivatives. Subsequent hydrolysis of the ester (G16/G20/G24) provides the corresponding acid or the carboxylate (G17/G21/G25). These can then be used as inputs for scheme 2/3. Moreover, the carboxylates itself can also be used for acylation reactions, where the —COOH is generated in-situ, as exemplified in Specific Examples 2 and 4.

Scheme 5.

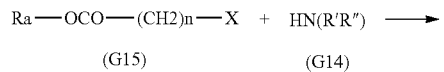

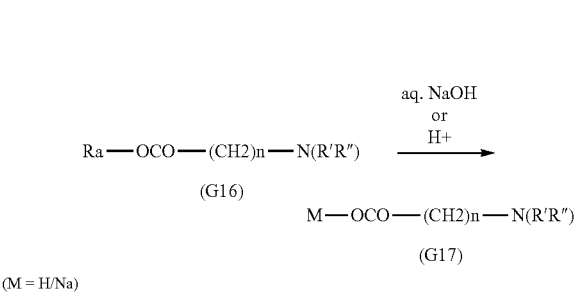

(M = H/Na)

Scheme 6.

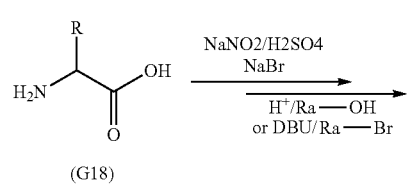

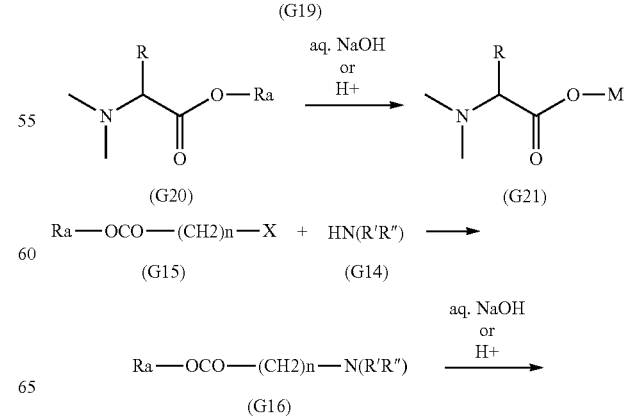

M—OCO—(CH2)n—N(R'R")

(G17)

(M = H / Na)

Scheme 7.

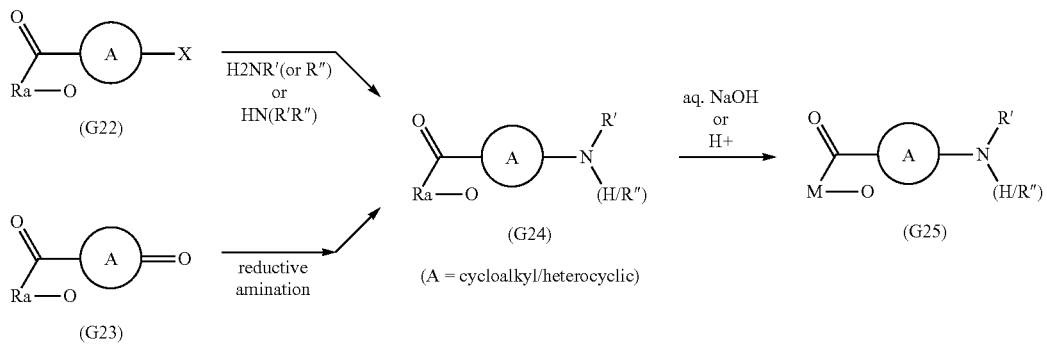

(A = cycloalkyl/heterocyclic)

Additional methods of synthesizing the compound can be found in, e.g., Stuart Warren and Paul Wyatt, *Workbook for Organic Synthesis: The Disconnection Approach*, second Edition, Wiley, 2010. Synthesis of the compound is exemplified in the Examples where the preparation additional compounds is described in detail.

Methods of Use

In an embodiment, provided herein is a method of using the RTC. The method comprises applying the RTC to a subject an RTC described herein to treat, prevent, or ameliorate a medical condition. The medical condition can be any disease or disorder caused by or otherwise associated with PTC.

In some embodiments, the method can be conducted in living bodies of mammals. In such a case, the compounds can be administered to the mammals. In one embodiment, the mammals can be patients with genetic diseases caused by nonsense mutation, and the method can be conducted as a treatment method of genetic diseases caused by nonsense mutation.

In an embodiment, provided herein are:

(i) methods of treating a disease or disorder in a subject caused by or associated with one or more premature termination codons of the subject, the method comprising administering a therapeutically effective amount of a compound or composition as described herein, for example of Formula I-VI, 8, 12, 16, 20 or 22, or prodrug or acyl derivative of compound 5 or 101, to the subject;

(ii) a method according to (i), wherein the disease or disorder is selected from the group consisting of central nervous system diseases, ataxia-telangiectasia, muscular dystrophy, Duchenne muscular dystrophy (DMD), Dravet syndrome, myotonic dystrophy, multiple sclerosis, infantile neuronal ceroid lipofuscinosis, Alzheimer's disease, Tay-Sachs disease, neural tissue degeneration, Parkinson's disease, autoimmune diseases, chronic rheumatoid arthritis, lupus erythematosus, graft-versus-host disease, primary immunodeficiencies, severe combined immunodeficiency, DNA Ligase IV deficiency, DNA repair disorders, Nijmegen breakage disorders, xeroderma pigmentosum (XP), inflammatory diseases, rheumatoid arthritis, blood diseases, hemophilia, von Willebrand disease, thalassemia, familial erythrocytosis, nephrolithiasis, collagen diseases, osteogenesis imperfecta, cirrhosis, neurofibroma, bullous disease, lysosomal storage disease, Hurler's disease, familial cholesterolemia, cerebellar ataxia, tuberous sclerosis, immune deficiency, kidney disease, lung disease, cystic fibrosis, familial hypercholesterolemia, pigmentary retinopathy, amyloidosis, atherosclerosis, gigantism, dwarfism, hypothyroidism, hyperthyroidism, aging, obesity, diabetes mellitus, Niemann-Pick disease, Marfan syndrome, neuromuscular diseases, Becker muscular dystrophy (BMD), spinal muscular atrophy, cancer, and any genetic disorder caused by nonsense mutation(s);

(iii) a method of (i) or (ii), wherein the disease or disorder is associated with a premature stop codon in an ATM or dystrophin gene of the subject;

(iv) a method according to (iii), where the disease or disorder is selected from ataxia-telangiectasia, breast cancer, and lymphoreticular malignancies;

(v) a method for enhancing production in a subject of a functional protein from a gene disrupted by the presence of a premature stop codon in the coding region of the gene, comprising administering to the subject a compound or composition described herein, for example a compound of Formula I-VI, 8, 12, 16, 20 or 22, or prodrug or acyl derivative of compound 5 or 101, in an amount effective to suppress the premature stop codon and increase transcription of the gene, optionally wherein the gene is an ATM or dystrophin gene; and (vi) a method for enhancing production in a subject of a functional protein, where production of the protein is disrupted by a genetic mutation, comprising administering to the subject a compound or composition described herein, for example a compound of Formula I-VI, 8, 12, 16, 20 or 22, or prodrug or acyl derivative of compound 5 or 101, in an amount effective to suppress the genetic mutation and/or correct a defect caused by the mutation and to increase transcription of the gene, optionally wherein the gene is an ATM or dystrophin gene.

As used herein, the term disorder and medical condition can be used interchangeably and generally refer to a disease attributable to an internal termination codon in a gene (a premature termination codon) generated by such as a point mutation, deletion, and insertion in the gene which leads to inhibition of expression of protein having a normal function, or attributable to degradation of mRNA that contains the premature termination codon which leads to inhibition of protein expression. The genetic disease caused by nonsense mutation is not specifically limited, but is exemplified by the following: central nervous system diseases such as muscular dystrophy, Duchenne muscular dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis and graft-versus-host disease; inflammatory diseases such as arthritis; blood diseases such as hemophilia, von Willebrand disease, ataxia telangiectasia, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesterolemia; cerebellar ataxia; tuberous sclerosis; immune deficiency; kidney disease; lung disease; cystic fibrosis; familial hypercholesterolemia; pigmentary retinopathy; amyloidosis; atheroscleroses; gigantism; dwarfism; hypothyroidism; hyperthyroidism; aging; obesity; diabetes mellitus; Niemann-Pick disease; Marfan syndrome; and cancer. The term "cancer", such as cancer associated with a nonsense mutation of a suppressor gene such as p53 gene, includes all types of cancer, which is exemplified by lung cancer, colon and rectal cancer, stomach cancer, esophagus cancer, kidney cancer, pancreatic cancer, prostate cancer, breast cancer, uterus cancer, ovary cancer, skin cancer and brain tumor.

Pharmaceutical Compositions

In another aspect, a pharmaceutical composition for use in treatment or prevention of the genetic diseases caused by nonsense mutation is provided, wherein the pharmaceutical composition comprises as an effective ingredient a compound expressed by any one of the aforementioned formulae a pharmacologically acceptable salt or prodrug thereof The pharmaceutical composition preferably comprises a compound described above or a pharmacologically acceptable salt or prodrug thereof.

The pharmaceutical composition more preferably comprises a compound shown in the aforementioned table.

In the aforementioned aspect, the pharmaceutical composition can contain a pharmacologically acceptable carrier or excipients. An amount of the compound used in the pharmaceutical composition is not limited as far as it is an effective amount for treatment. The genetic disease caused by nonsense mutation is not specifically limited, but is exemplified by the following: central nervous system diseases such as muscular dystrophy, Duchenne muscular dystrophy, multiple sclerosis, infantile neuronal ceroid lipofuscinosis, Alzheimer's disease, Tay-Sachs disease, neural tissue degeneration, and Parkinson's disease; autoimmune diseases such as chronic rheumatoid arthritis and graft-versus-host disease; inflammatory diseases such as arthritis; blood diseases such as hemophilia, von Willebrand disease, ataxia telangiectasia, thalassemia, familial erythrocytosis, and nephrolithiasis; collagen diseases such as osteogenesis imperfecta and cirrhosis; neurofibroma; bullous disease; lysosomal storage disease; Hurler's disease; familial cholesterolemia; cerebellar ataxia; tuberous sclerosis; immune deficiency; kidney disease; lung disease; cystic fibrosis; familial hypercholesterolemia; pigmentary retinopathy; amyloidosis; atherosclerosis; gigantism; dwarfism; hypothyroidism; hyperthyroidism; aging; obesity; diabetes mellitus; Niemann-Pick disease; Marfan syndrome; and cancer. The term "cancer", such as cancer associated with a nonsense mutation of a suppressor gene such as p53 gene, includes all types of cancer, which is exemplified by lung cancer, colon and rectal cancer, stomach cancer, esophagus cancer, kidney cancer, pancreatic cancer, prostate cancer, breast cancer, uterus cancer, ovary cancer, skin cancer and brain tumor.

The pharmaceutical composition in the aspect can contain, as active ingredients, the aforementioned compound and other compounds, or can contain a mixture of two or more aforementioned compounds.

The pharmacologically acceptable salt in the present specification is not specifically limited as far as it can be used in medicaments. Examples of a salt that the compounds described herein forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts can be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

Further, the compounds described herein include hydrates thereof, various pharmaceutically acceptable solvates thereof, and polymorphic crystals thereof.

The pharmaceutical compositions described herein can be formulated in various dosage forms, which are exemplified by the following: oral administration forms such as tablets, capsules, powders, granules, pills, liquids, emulsions, suspensions, solutions, spirits, syrups, extracts, and elixirs; parenteral administration forms such as injections, for example, subcutaneous injections, intravenous injections, intramuscular injections, and intraperitoneal injections; transdermal administration forms, plasters and pressure sensitive adhesives, ointments or lotions; intramouth administration forms such as sublingual forms and oral patch preparations; and nasal administration forms such as aerosols, but are not limited thereto. These preparations can be manufactured by using a known method generally used in a drug manufacturing process. In one embodiment, the pharmaceutical composition described herein can be administered for treating muscular disease as an injection such as an intramuscular injection for administering directly into muscle.

The pharmaceutical compositions can contain various kind of ingredients generally used, for example, one or more pharmaceutically acceptable fillers, disintegrators, diluents, lubricants, flavoring agents, colorants, sweetening agents, corrigents, suspending agents, humectants, emulsifying agents, dispersing agents, auxiliary agents, preservatives, buffers, binders, stabilizers, and coating agents. In addition, the pharmaceutical composition described herein can be sustained-release dosage forms or extended-release dosage forms.

Dosage ranges of the pharmaceutical compositions are not particularly limited, and can be determined in accordance with the following: effectiveness of the ingredients contained therein; the administration form; the route of administration; the type of disease; the characteristics of the subject (e.g., body weight, age, symptomatic conditions, and whether a subject is taking other pharmaceutical agents); and the judgment of a physician in charge. In general, a suitable dosage can fall, for example, within a range of about 0.01 μg to 100 mg, per 1 kg of the body weight of the subject, and preferably within a range of about 0.1 μg to 1 mg, per 1 kg of body weight. However, the dosage can be altered using conventional experiments for optimization of a dosage that are well-known in the art. The aforementioned dosage can be divided for administration once to several times a day. Alternatively, periodic administration once every few days or few weeks can be employed.

The pharmaceutical compositions can be administered to a patient whose biological sample obtained in advance is subjected to a study for presence or absence of premature termination codons in genes contained therein and is found to have a detected premature termination codon. A biological sample can be any ones insofar as it contains nucleic acids, and is exemplified by cells, bloods, cerebrospinal fluids, bronchoalveolar lavage fluids, expectorations, or other body fluids as well as biopsy tissues. Nucleic acid samples can be prepared from the biological samples for use. The nucleic acid samples can be prepared by well-known nucleic acid preparation methods. The nucleic acid samples can be DNA or RNA. The nucleic acid samples prepared can be used directly for detection, or can be subjected to enzymatic amplification of predetermined region thereof by PCR or other amplification methods in advance for analysis. Detection of a termination codon can be carried out by using well-known methods for detecting genetic mutations such as DNA sequencing, Southern blot, polymerase chain reaction (PCR), short tandem repeat (STR), or restricted fragment length polymorphism. The detection method is not limited to the exemplified methods, and any method can be used insofar as it can detect a premature termination codon. Alternatively, the presence of a premature termination codon can be detected by measuring an amount of mRNA derived from the predetermined gene in the biological sample and detecting reduction of the amount of the mRNA compared to an amount of mRNA derived from the gene in a biological sample obtained from healthy subject. mRNA can be measures by using known analysis methods such as northern blotting.

In terms of a route of administration of the pharmaceutical composition, it can be either systemic administration or local administration. The route of administration that is appropriate for a particular disease, symptomatic condition, or other factors, should be selected. For example, parenteral administration including normal intravenous injection, intra-arterial administration, subcutaneous administration, intra-cutaneous administration, and intramuscular administration can be employed. Oral administration can be also employed. Further, transmucosal administration or transdermal administration can be employed.

The term "read-through" herein means to skip over a premature termination codon in ribosomal translation, or to substitute an amino acid, or to suppress degradation of mRNA that comprises a premature termination codon.

In the aforementioned aspect, a sequence that comprises a premature termination codon derive from responsible genes for diseases caused by nonsense mutation is not specifically limited insofar as it is a sequence comprising a termination codon such as TAA, TAG, or TGA, in a reading flame. The sequence is preferably around 20 to 150 by long.

In one embodiment, the sequence can be a sequence containing a sequence that comprises a premature termination codon of humans or animals having genetic disease caused by nonsense mutation including animal models for the diseases. For example, such a gene can contain a premature termination codon in the dystrophin gene of mdx mice.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragées, or gelatin capsules per day. However, the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch, or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds described herein. Agents which can advantageously be combined with compounds described herein in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds described herein in single formulations are in accord with the doses used in standard clinical practice. Established safe and effective dose ranges for certain representative compounds are set forth above.

The invention is described in more detail in the following illustrative examples. Although the examples can represent selected embodiments described herein, it is intended that the following examples are illustrative and not limiting.

EXAMPLES

Example 1

Comparative

Preparation of (5Z)-2-imino-5-{[5-(2-nitrophenyl)furan-2-yl]methylidene}-1,3-thiazolidin-4-one (compound 5)

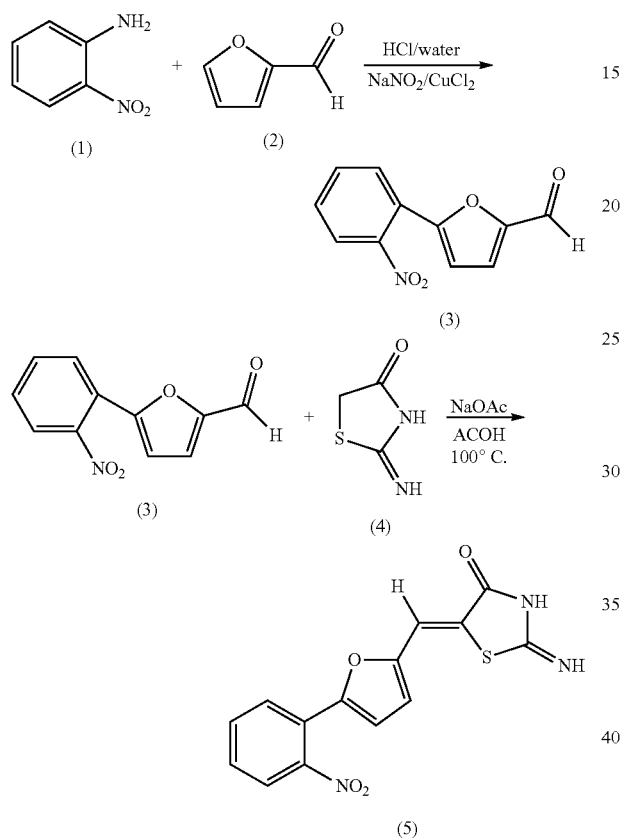

Step-1: 5-(2-nitrophenyl)furan-2-carbaldehyde (3). To a stirred solution of 2-nitro aniline (100 g, 0.72 mol) in 6 N HCl (1000 mL) was heated up to 80° C. and stirred for 30 min. The solution was cooled to 0° C. and a solution of sodium nitrite (55 g, 0.796 mol in 180 mL of water was added drop wise over 30 min. To the ice cold solution of the diazonium salt was added 2-furfuraldehyde (70 g, 0.724 moles) over 30 min, followed by drop wise addition of solution of cupric chloride (17 g, 0.1264 mol in 180 mL water) over 20 min at 0° C. Reaction mass was stirred at room temperature for 30 h. Solid was filtered and wet cake was stirred in 1:1 dioxane/ethanol (150 mL) for 15 min, solid was filtered, washed with hexane (100 mL) and air dried to provide 55 g of (3) as a light yellow solid. (Yield: 35%). M.P:98-100° C. $^1$H-NMR (CDCl3): ppm 9.71 (1H, s), 7.86 (1H, m), 7.04 (1H, m), 7.67 (1H, m), 7.35, (1H, m), 7.34 (1H, s), 6.81 (1H, m).

Step-2: (5Z)-2-imino-5-{[5-(2-nitrophenyl)furan-2-yl]methylidene}-1,3-thiazolidin-4-one (5) [RTC-13]. To a stirred solution of aldehyde (50 g, 0.23 mol) in acetic acid (1500 mL) was added 2-imino-1,3-thiazolidin-4-one (27 g, 0.23 mol) and sodium acetate (75 g, 0.924 mol) was heated to 100° C. for 18 h. Reaction mass at 70° C. was filtered (undissolved solid was discarded), filtrate was cooled to room temperature and 500 mL of water was added. The resulting solid was filtered and washed with water (500 mL). The wet cake was dried at 70° C. for 8 h under reduced pressure. The above solid was refluxed in toluene (600 mL) for 1 h, filtered while hot and the solid compound was dried in a vacuum oven at 60° C. under reduced pressure (520 mmHg) to provide 27 g (yellow solid), isolated yield: 38%. HPLC=98% purity (area percent, 254 nm). M.P: 263-265° C. $^1$H-NMR (DMSO-d6): ppm 9.4 (1H, s), 9.2 (1H, s), 8.0 (1H, d, 6 Hz), 7.9 (1H, d, 6 Hz), 7.8 (1H, t, 6 Hz), 7.65 (1H, t, 6H), 7.45 (1H, s), 7.11 (2H, m). LC-MS: 316 (MH+, ES+APCI, positive mode). Elemental Analysis: calculated for Cl4H9N3O4S, Element: Expt. (Theory)=C: 53.08 (53.33), H: 3.00 (2.88), N: 12.96 (13.33) and S: 10.26 (10.17).

Example 2

Preparation of prodrug derivative 2-(4-methylpiperazin-1-yl)-N-[(2E,5Z)-5-{[5-(2-nitrophenyl)furan-2-yl]methylidene}-4-oxo-1,3-thiazolidin-2-ylidene]acetamide dihydrochloride (8)

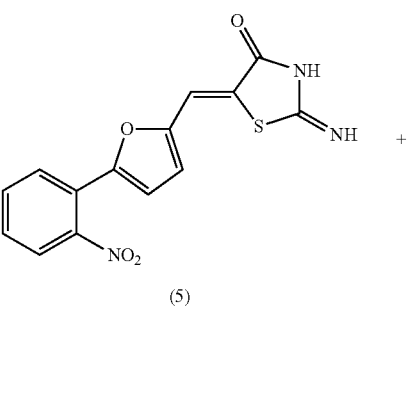

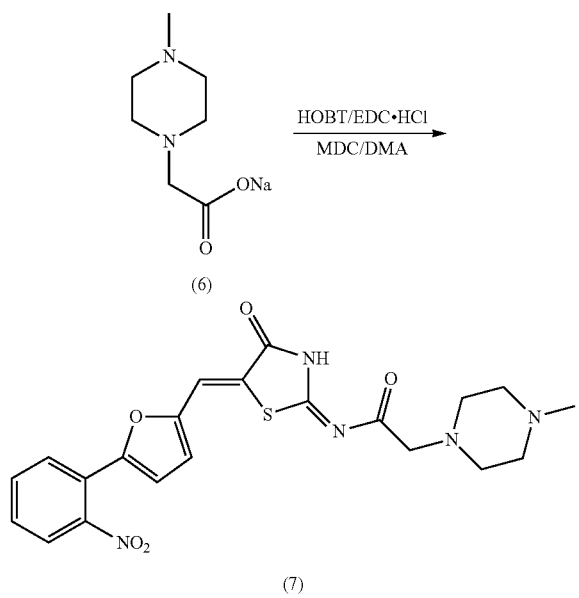

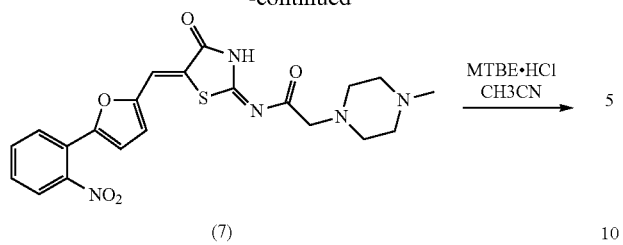

Example 3

Preparation of prodrug derivative: 2-(4-methylpiperazin-1-yl)-N-[(2E,5Z)-5-{[5-(2-nitrophenyl)furan-2-yl]methylidene}-4-oxo-1,3-thiazolidin-2-ylidene] acetamide dihydrochloride (8)

Step-1: 2-(4-methylpiperazin-1-yl)-N-[(2E,5Z)-5-{[5-(2-nitrophenyl)furan-2-yl]methylidene}-4-oxo-1,3-thiazolidin-2-ylidene]acetamide (7). To a stirred solution of sodium (4-methylpiperazin-1-yl)acetate (0.50 g, 2.77 mmol) in dichloromethane (15 mL) was added EDCI.HCl (0.6 g, 3.04 mmol), HOBt (0.4 g, 3.04 mmol) and DIPEA (0.386 g, 3.04 mmol) at 0° C., mixture was stirred at 0° C. for 30 min. A solution of RTC-13 (0.8 g, 0.00253 mol) in 15 mL DMA was added at 0° C. Reaction mixture was stirred at room temperature for 5 h. Reaction mass was diluted with MTBE and water (1:1 v/v, 200 mL), the turbid mass was filtered, the layers were separated, aq. layer was extracted with 10% MeOH/CHCl$_3$ (50 ml×2), the organic (CHCl$_3$) layer was dried over anhydrous sodium sulphate, and evaporated to provide 0.6 g of a yellow solid as free-base (7) (Yield: 54%). HPLC=93% purity (area percent, 254 nm). HPLC-93%. LC-MS: 456 (MH+, ES+APCI, positive mode).

Step-2: A suspension of (7) (0.20 g, 0.439 mmol) in acetonitrile (6 mL) was cooled to 0° C. added 15% HCl in MTBE (158 mg, 4.329 mmol) and stirred at same temperature for 1 h. The solid was filtered and washed with hexane (20 mL) to provide, after drying 0.20 g of (8) as a yellow solid. (Yield: 87%). HPLC (area percent, 254 nm) 97% purity. M.P:198-202° C. $^1$H-NMR: (DMSO-d6) ppm 11.5 (0.6H, bs), 8.15 (1H, d, 6 Hz), 7.92 (1H, d, 6 Hz), 7.85 (1H, t, 6 Hz), 7.75 (1H, t, 6 Hz), 7.70 (1H, s), 7.35 (1H, d, 3 Hz), 7.20 (1H, d, 3 Hz), 4.10 (2H, bs), 3.2-3.6 (8H, m), 2.8 (3H, s). Elemental Analysis calculated for C21H21N5O5S.2HCl.2H2O, Element: Expt (Theory)=C: 44.69 (44.09), H: 4.82 (4.86), N: 12.41 (12.28), S: 5.68 (5.93).

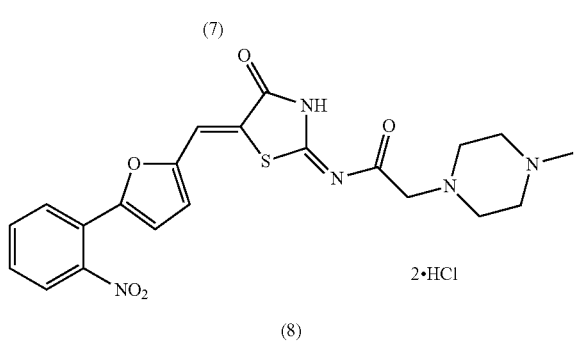

Step-1: 2-(4-methylpiperazin-1-yl)-N-[(2E,5Z)-5-{[5-(2-nitrophenyl)furan-2-yl]methylidene}-4-oxo-1,3-thiazolidin-2-ylidene]acetamide (7). To a stirred solution of (4-methyl-1-piperzinnyl)acetic acid (6.62 g, 0.03809 mol) in dichloromethane (100 ml) was added EDCI.HCl (7.35 g, 0.03809 mol), HOBT (5.82 g, 0.03809 mol) and DIPEA (11.2 ml, 0.063 mol) at 0° C., stirred at same temperature for 30 mints and at room temperature for 30 mint. A solution of (5) (10 g, 0.03174 mol in 1100 ml DMA, dissolved at 60° C., and then cooled to room temperature) drop wise in 20 mints at 0° C. Further mixture was stirred at room temperature for 24 h. Solid was separated out from the mixture, filtered and washed with dichloromethane (25 ml). The obtained compound (8 g) was stirred in water (80 ml) for 1 h and filtered, dried at 50° C. to get a constant weight (7 g). The dry compound was stirred in methanol (200 mL) for 1 h and filtered, dried under high vacuum pump at room temperature to get a constant weight, to provide 6.7 g of a yellow color solid, the free-base (7). Yield: 47%. HPLC=98% purity (area percent, 254 nm). ¹HNMR: matched with spectra from example 2, step-1. LC-MS: 465 (MH+, ES+APCI, positive mode). Elemental Analysis: calculated for C21H21N5O5S, Element: Expt. (Theory)=C: 54.83 (55.37), H: 5.12 (4.65), N: 15.10 (15.38) and S: 6.74 (7.04).

Step-2: Salt formation. A suspension of (7) (0.20 g, 0.439 mmol) in acetonitrile (6 mL) was cooled to 0° C., 15% HCl in MTBE (158 mg, 4.329 mmol) was added and stirred at 0° C. for 1 h. The solid was filtered and washed with hexane (20 mL), dried under high vacuum to provide 0.20 g of (8) as a yellow solid, (yield 87%). HPLC (area percent, 254 nm) 97% purity. M.P:198-202° C. ¹H-NMR: (DMSO-d6) ppm 11.5 (0.6H, bs), 8.15 (1H, d, 6 Hz), 7.92 (1H, d, 6 Hz), 7.85 (1H, t, 6 Hz), 7.75 (1H, t, 6 Hz), 7.70 (1H, s), 7.35 (1H, d, 3 Hz), 7.20 (1H, d, 3 Hz), 4.10 (2H, bs), 3.2-3.6 (8H, m), 2.8 (3H, s). ¹H-NMR: (TFA-d6) ppm 8.22 (1H, bs), 8.15 (1H, m), 7.65 (2H, bs), 7.58 (1H, m), 7.50 (1H, d, 3 Hz), 7.18 (1H, d, 3 Hz), 5.05 (2H, bs), 4.40 and 4.30 (8H, two overlapping broad singlets), 3.30 (3H, s). Elemental Analysis calculated for C21H21N5O5S.2HCl, Element: Expt (Theory) C: 47.97 (47.73), H: 4.92 (4.39), N: 13.24 (13.25), and S: 6.05 (6.07).

Step-2: Salt formation. To a stirred suspension of (7) (6.2 g, 13.6 mmol) in acetonitrile (185 mL) was cooled to 0° C., 25% MTBE.HCl (tert-butylmethylether.HCl) (3.4 g (14 ml), 95 mmol) was added drop wise in 20 min and stirred at 0° C. for 2 h. The solid was filtered and the wet cake was triturated with 200 mL of methanol, sonicated for 5 min and filtered, solid was dried under high vacuum at room temperature to a constant weight to provide 6.1 g of (8) as a yellow color solid, (Yield: 80%). HPLC=99.0% purity (area percent, 254 nm). M.P:198-202° C. ¹HNMR: consistent with data shown for example 2 and 3, step-2. Elemental Analysis calculated for C21H21N5O5S-2HCl-1.5H2O: Element: Expt (Theory)=C: 45.41 (45.53), H: 4.72 (5.02), N: 12.61 (12.51), S: 5.77 (5.87).

Example 4

Preparation of prodrug derivative: (E)-N²,N²-dimethyl-N-[(5Z)-5-{[5-(2-nitrophenyl)furan-2-yl]methylidene}-4-oxo-1,3-thiazolidin-2-ylidene]glycinamide hydrochloride (12)

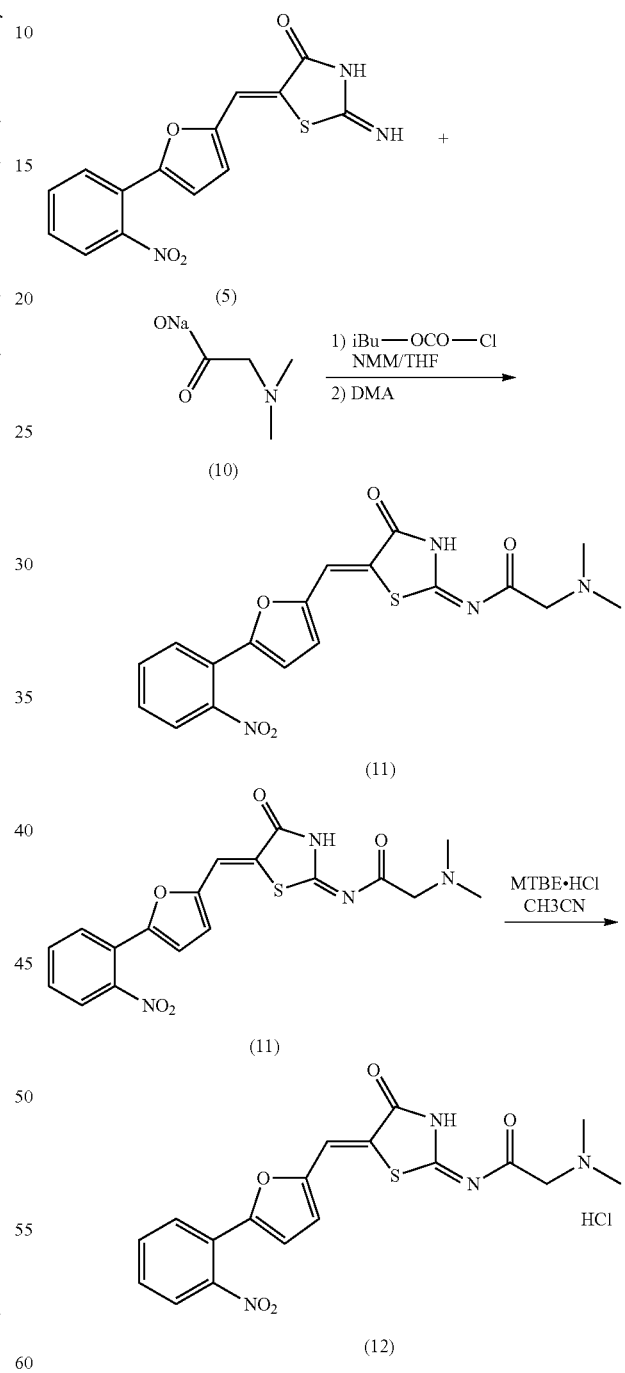

Step-1: (E)-N²,N²-dimethyl-N-[(5Z)-5-{[5-(2-nitrophenyl)furan-2-yl]methylidene}-4-oxo-1,3-thiazolidin-2-ylidene]glycinamide (11). A solution of sodium salt (0.70 g, 5.6 mmol) in THF (20 mL) was cooled to 0° C., isobutyl chloroformate (0.76 g, 5.7 mmol) was added, followed by N-methylmorpholine (1.14 g, 11.4 mmol), reaction mixture stirred at same temperature for 1 h. A solution of (5) (1.2 g, 3.8 mmol) in dimethylacetamide (15 mL) was added at 0° C. over 5 min. The reaction mixture was stirred at 0° C. for 6 h. Reaction mass was diluted with MTBE and water (1:1 v/v, 200 mL), and the solid was filtered. The solid obtained solid (600 mg) was purified by silica gel column eluting with 20% acetone/CHCl$_3$ to provide 0.3 g of a yellow solid (11). (Yield: 20%). $^1$HNMR (DMSO-d6) ppm 8.00 (1H, d, 6 Hz), 7.93 (1H, d, 6 Hz), 7.85 (1H, t, 6 Hz), 7.65 (1H, t, 6 Hz), 7.35 (1H, s), 7.1 (2H, s), 3.8 (2H, s), 3.2-3.5 (bs), 2.65 (6H, s).

Setp-2: Salt formation. A suspension of 9× (0.180 g, 0.45 mmol) in acetonitrile (6 mL) was cooled to 0° C., 1 mL of 15% MTBE.HCl (162 mg, 4.5 mmol) was added and stirred at same temperature for 1 h. The resulting compound was filtered and washed with hexane (20 mL), dried under vacuo to provide 0.20 g of (12) as a light greenish solid. (Yield: 98%). HPLC=99.0% purity (area percent, 254 nm). LC-MS: 401 (MH+, ES+APCI, positive mode). $^1$HNMR (DMSO-d6) ppm 8.07 (1H, d, 6 Hz), 7.95 (1H, d, 6 Hz), 7.85 (1H, t, 6 Hz), 7.75 (1H, t, 6 Hz), 7.70 (1H, s), 7.35 (1H, d, 3 Hz), 7.25 (2H, d, 3 Hz), 4.4 (2H, s), 3.35 (1H, bs), 2.9 (6H, s).

Example 5

Preparation of prodrug derivative: N-[(2E,5Z)-5-{[5-(2-nitrophenyl)furan-2-yl]methylidene}-4-oxo-1,3-thiazolidin-2-ylidene]piperidine-4-carboxamide hydrochloride (16)

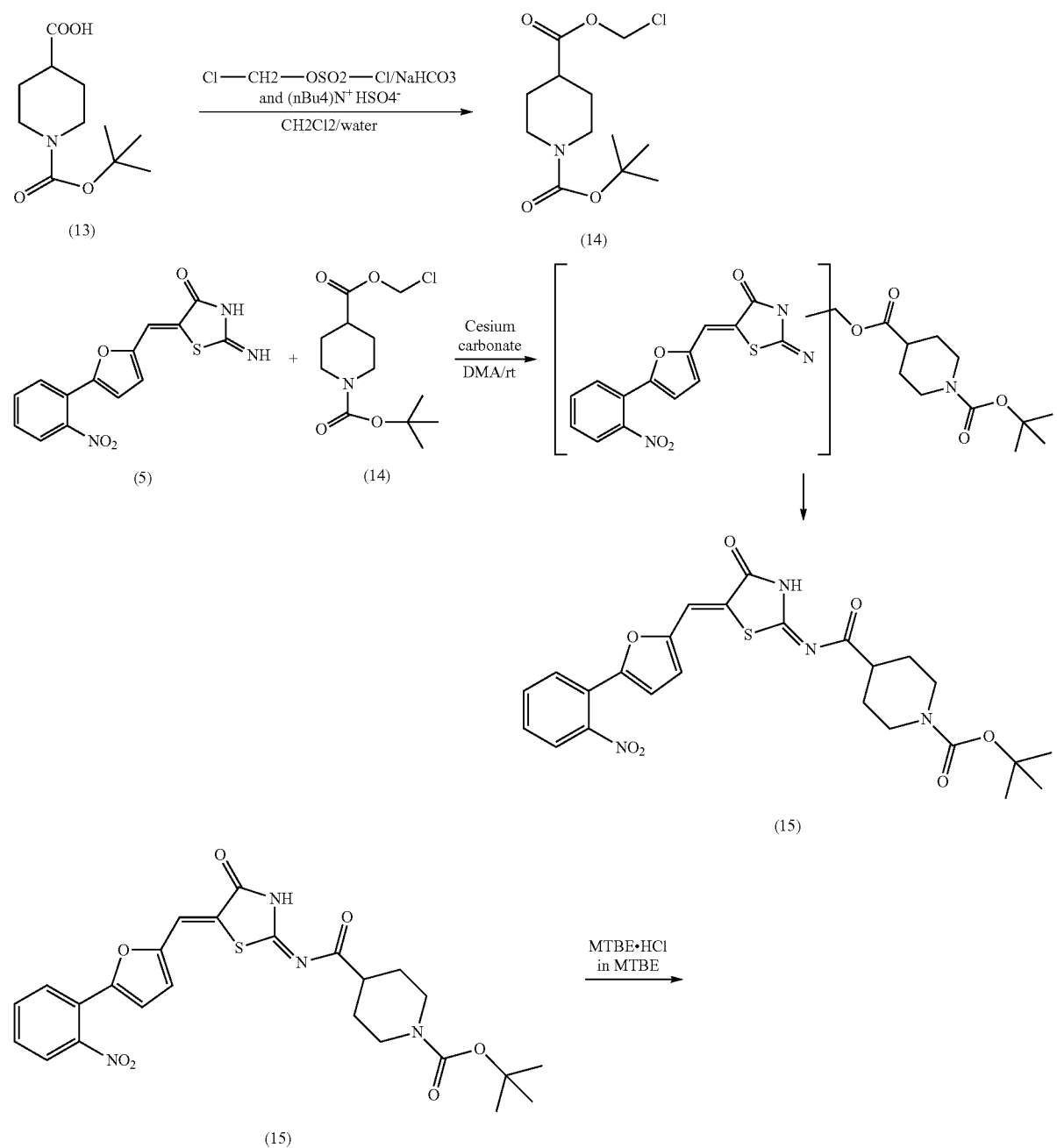

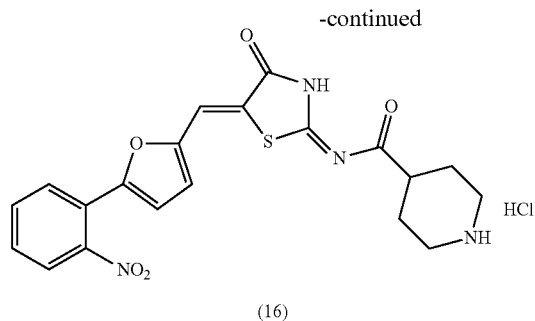

(16)

Step-1: To a solution of 1-(tert-butoxycarbonyl)piperidine-4-carboxylic acid (5 g, 21.8 m mol) in a mixture of dichloromethane and water (60 mL:80 mL) was added chloromethyl chlorosulfonate (4.3 g, 26 mmol) drop wise, subsequently solid NaHCO$_3$ (7 g, 84 mmol) was added portion wise, followed by n-tetrabutylammonium hydrogen sulphate (TBAHS) (0.7 g, 2.1 mmol) at room temperature. The resulting reaction mixture was stirred at room temperature for 5 h. The organic layer was separated, washed with water and dried over anhydrous sodium sulfate, filtered and concentrated in vacuo to provide 5.2 g of a white solid, yield: 86%. This was confirmed by LCMS and used as such for next step.

Step-2: To a solution of (5) (2 g, 6.3 mmol) in DMA (25 mL) was added cesium carbonate (2.45 g, 7.5 mmol) at room temperature, stirred for 15 min, and then cooled to 0° C., followed by addition of (14) (2.25 g, 8.1 mmol). The reaction mixture was stirred at room temperature for 5 h. Reaction mass was diluted with MTBE and water (1:1 v/v, 100 mL). Layers were separated and aq. layer was extracted with 10% MeOH/CHCl$_3$ (50 mL×2). The combined organic layer was dried over anhydrous sodium sulphate, filtered and concentrated in vacuo to provide 0.4 g of (15) a yellow solid. This was the only product observed during the reaction and was isolated. $^1$HNMR (DMSO-d6) ppm 12.5 (0.8H, bs), 8.05 (1H, d, 6 Hz), 7.90 (1H, d, 6 Hz), 7.85 (1H, t, 6 Hz), 7.70 (1H, t, 6 Hz), 7.62 (1H, s), 7.25 (1H, d, 3 Hz), 7.15 (2H, d, 3 Hz), 3.95 (1H, m), 2.7-2.9 (4H, m), 1.85 (2H, m), 1.45 (2H, m), 1.35 (9H, s).

Step-3: To a suspension of (15) (0.4 g, 0.76 mmol) in MTBE (20 mL) 15% MTBE.HCl (1.8 mL, 0.27 g, 15 mmol) was added at 0-5° C. and stirred at same temperature for 24 h, still starting material was observed, further added 1.8 mL of MTBE.HCl (0.27 g, 0.015 mol) and stirred for additional 18 h. Reaction mass was diluted with ACN (15 mL) and filtered. The solid was stirred in hexane (20 mL) for 10 min and filtered to provide 0.208 g of a light yellow solid, (yield: 48%). MP: 290-293° C. HPLC=95.8% purity (area percent, 254 nm). LC-MS: 427 (MH+, ES+APCI, positive mode). $^1$HNMR (DMSO-d6) ppm 9.0 (1H, bs), 8.75 (1H, bs), 8.05 (1H, d, 6 Hz), 7.90 (1H, d, 6 Hz), 7.85 (1H, t, 6 Hz), 7.73 (1H, t, 6 Hz), 7.65 (1H, s), 7.35 (1H, d, 3 Hz), 7.18 (2H, d, 3 Hz), 3.3 (1H, m), 2.8-3.0 (4H, m), 2.02 (2H, m), 1.80 (2H, m).

Example 6

Preparation of prodrug derivative: 2-(morpholin-4-yl)-N-[(2E,5Z)-5-{[5-(2-nitrophenyl)furan-2-yl]methylidene}-4-oxo-1,3-thiazolidin-2-ylidene]acetamide (20)

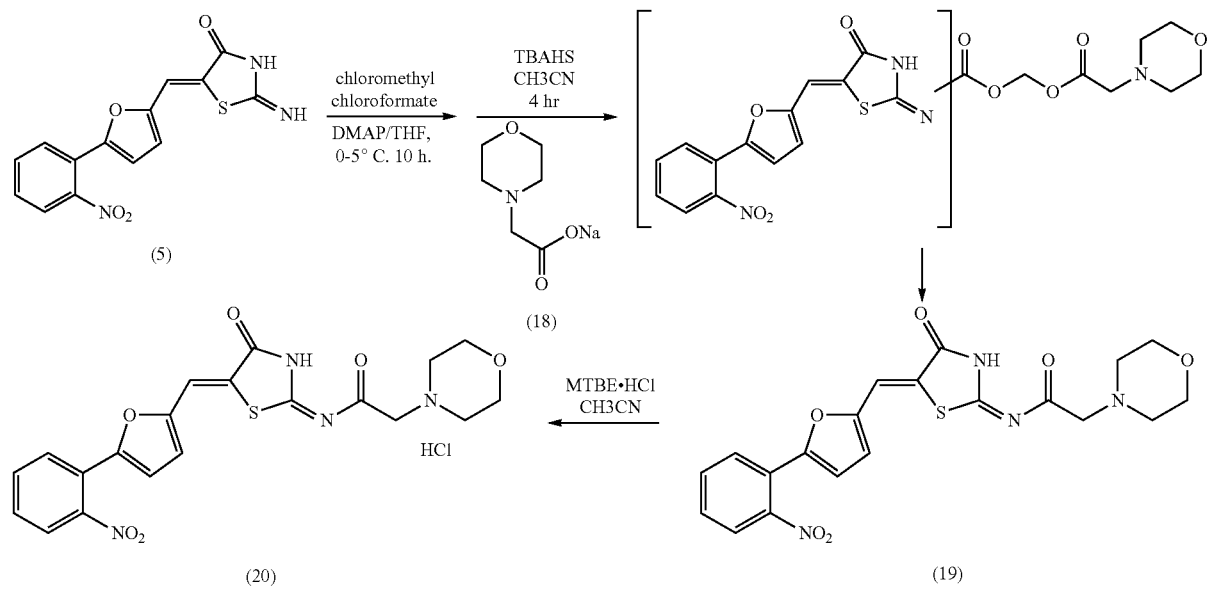

Step-1: To a solution of (5) (3 g, 9.5 mmol) in THF (250 mL) DMAP (1.5 g, 1.2 mmol) was added at −5° C., and chloromethyl chloroformate (1.2 mL, 11.8 mmol) drop wise at 0-5° C. and further stirred at 0° C. for 12 h. Reaction mass was diluted with water (700 mL) and filtered, the compound was dried at rt for 5 h to provide 3 g of a pale yellow solid (LC/MS confirmed) and was used as such for the next step. To a 1 g (2.45 mmol) solution in acetonitrile (100 mL) was added sodium morpholin-4-ylacetate (18) (0.82 g, 4.9 mmol) followed by TBAHS (1.2 g, 3.5 mmol) at room temperature and stirred at ambient temperature for 5 h. HPLC of the reaction mixture indicated a new product and small amounts of the starting (5). Reaction mass was filtered and the solid was stirred in water and filtered, the compound was dried at 50° C. for 5 h under vacuo to provide 0.38 g of (19) as a yellow solid, (yield 35%). $^1$HNMR (DMSO-d6) ppm 8.05 (1H, d, 6 Hz), 7.92 (1H, d, 6 Hz), 7.85 (1H, t, 6 Hz), 7.70 (1H, t, 6 Hz), 7.65 (1H, s), 7.30 (1H, d, 3 Hz), 7.15 (1H, d, 3 Hz), 3.6 (4H, m), 3.45 (2H, s), 2.6 (4H, m).

Step-3: A suspension of (19) (0.150 g, 0.339 mmol) in acetonitrile (5 mL) was cooled to 0° C., 15% MTBE.HCl (0.8 ml, 122 mg, 3.34 mmol) was added and stirred at same temperature for 30 min. The compound was filtered, washed with hexane (20 ml) and dried under vacuo to provide 0.110 g of (20) as a yellow solid, (yield: 68%). HPLC=95.3% purity (area percent, 254 nm). LC-MS: 443 (MH+, ES+APCI, positive mode). M.Pt.: 226-230° C. 1HNMR (DMSO-d6) ppm 8.1 (1H, d, 6 Hz), 7.95 (1H, d, 6 Hz), 7.90 (1H, 7, 6 Hz), 7.5 (2H, m), 7.4 (1H, d, 3 Hz), 7.25 (1H, d, 3 Hz), 4.45 (2H, s), 3.90 (4H, bs), 3.2-3.5 (4H, bs). $^1$H-NMR: (TFA-d6) ppm 8.15 (1H, s), 8.10 (1H, d, 6 Hz), 7.80 (2H, s), 7.75 (1H, m), 7.50 (1H, d, 3 Hz), 7.10 (1H, d, 3 Hz), 4.80 (2H, bs), 4.40 (4H, bs), 3.80 (2H, m), 3.65 (2H, m).

Example 7

Preparation of derivative tert-butyl [(2S)-1-{[(2E, 5Z)-5-{[5-(2-nitrophenyl)furan-2-yl]methylidene}-4-oxo-1,3-thiazolidin-2-ylidene]amino}-1-oxopropan-2-yl]carbamate (22)

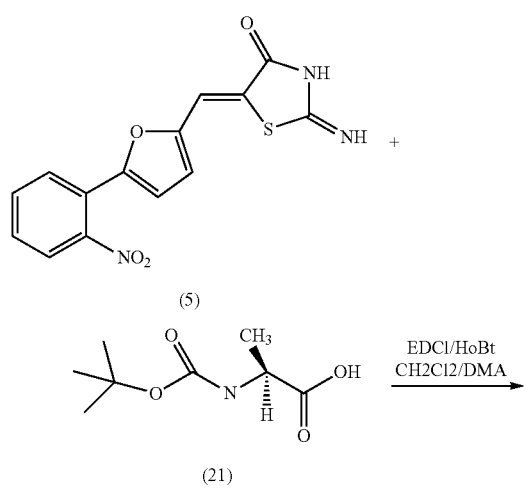

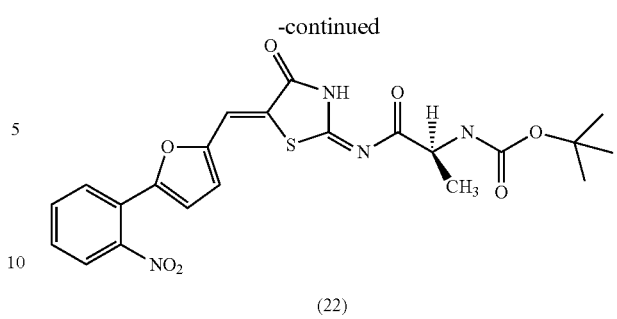

(22)

To a stirred solution of BOC-L-alanine (21) (59 mg, 0.32 mmoles) in dichloromethane (5 mL) and diisopropylethylamine (61 mg, 0.47 mmol) at 0-5° C. were added EDCI.HCl (73 mg, 0.378 mmol) and HOBt (51 mg, 0.37 mmol). The resulting reaction mixture was stirred at 0-5° C. for 30 min. A solution of (5) (100 mg, 0.317 mmol) in DMA (5 mL) was added and the mixture was stirred overnight at room temperature. The completion of the reaction was monitored by TLC. The reaction mixture was poured into ice-cold water (25 mL) and extracted with dichloromethane (3×20 mL). The combined organic layer was washed with water and dried over anhydrous Na2SO4, filtered and concentrated under reduced pressure, to provide 45 mg of (22) as a yellow solid. $^1$HNMR (CDCl3) ppm 12.0 (0.85H, bs), 7.90 (1H, d, 6 Hz), 7.55 (1H, d, 6 Hz), 7.75 (2H, m), 7.55 (1H, t, 6 Hz), 7.0 (1H, d, 3 Hz), 6.85 (1H, d, 3 Hz), 6.35 (0.7H, bs), 4.65 (1H, m), 1.6 (3H, d), 1.35 (9H, s).

Example 8

Aqueous Solubility

The solubility of selected compounds was tested and compared to that of comparative compound 5. To 5 mg of each test compound, water was slowly added initially in 0.5 mL and then 0.1 mL increments with vortexing for approximately 1 minute in between each aliquot of water addition and visually inspected for homogeneity. Comparative compound 5 was diluted to 1 L with water and vigorously stirred for up to 12 hr, but still the sample did not appear to dissolve fully. Table 1 provides the aqueous solubility of various prodrugs.

TABLE 1

Aqueous Solubility of Selected Compounds

| Compound No. | Solubility in (mg/mL) water at ambient pH, at room temperature |
|---|---|
| 5 (Comparative) | <0.005 |
| 8 | 3.3 |
| 12 | 10.0 |
| 16 | 0.18 |
| 20 | 0.1 |

While particular embodiments described herein have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. A compound according to Formula Ia:

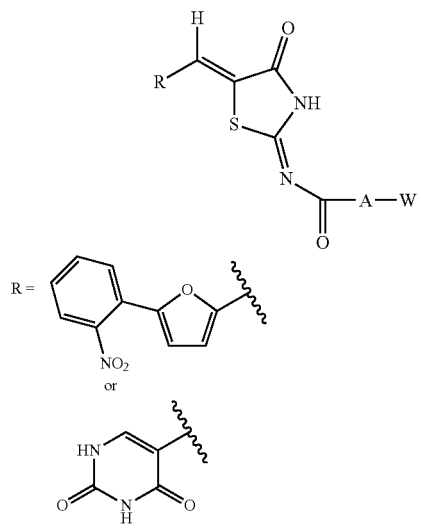

or a pharmaceutically acceptable salt, stereoisomer, or tautomer thereof, wherein:

W is —NR$^a$R$^b$, —C(O)OR$^4$, —C(O)NR$^a$R$^b$, or -HetAr;
A is a bond from C(O) to W, —(CH$_2$)$_f$CH(R$^1$)(CH$_2$)$_g$—, —(CH$_2$)$_f$C(R$^a$R$^b$)(CH$_2$)$_g$—, —(CH$_2$CH$_2$O)$_h$(CH$_2$)$_t$—, —(CH$_2$)$_t$(OCH$_2$CH$_2$)$_h$—, —(CH$_2$)$_t$N(R$^e$)CH$_2$CH$_2$Z, or

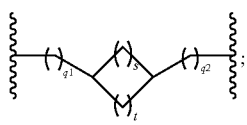

or A and W combine to form

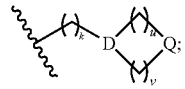

R$^1$ is —H, —(CH$_2$)$_n$CH$_3$, —CH(CH$_3$)CH$_2$CH$_3$, —CF$_3$, —CH$_2$(Ar), —CH$_2$(HetAr), —CH$_2$S(O)$_m$CH$_3$, —CH$_2$CH$_2$S(O)$_m$CH$_3$, —CH$_2$(CH$_2$)$_n$NR$^c$R$^d$, —CH$_2$OH, —CH(CH$_3$)OH, or —(CH$_2$)$_t$COOH;
R$^2$ is —H, —CH$_3$, —OH, or —CF$_3$;
each of R$^a$ and R$^b$ is independently R$^e$; or, in the alternative, R$^a$ and R$^b$, together with the nitrogen or carbon atom to which they are attached, combine to form a 4 to 7-membered heterocyclic ring, optionally containing heteroatoms selected from O, NR$^g$, and S(O)m;
R$^c$ is —H, —CH$_3$, —(CH$_2$)$_n$CH$_3$, —CH(R$^2$)CH$_3$, —CH$_2$-pyridyl, or CH$_2$-imidazolyl;
R$^d$ is —H, —CH$_3$, or —(CH$_2$)$_n$CH$_3$; or, in the alternative, R$^c$ and R$^d$, together with the nitrogen atom to which they are attached, form a 4-7 membered heterocyclic ring optionally containing heteroatoms selected from O, NR$^e$, and S(O)$_m$;
each R$^e$ is independently —H, —(CH$_2$)$_n$CH$_3$, —CH(CH$_3$)$_2$, —CH(CH$_3$)CH$_2$CH$_3$, —(CH$_2$CH$_2$O)$_p$R$^3$, or —CH$_2$HetAr;

each R$^g$ is independently —H, —(CH$_2$)$_n$CH$_3$, —CH(CH$_3$)$_2$, —CH(CH$_3$)CH$_2$CH$_3$, —(CH$_2$CH$_2$O)$_p$R$^3$, —CH$_2$-phenyl or —CH$_2$-phenyl optionally substituted with F, Cl, —CH$_3$, —OCH$_3$, —OCF$_3$, or -HetAr;
each R$^3$ is independently —H, —CH$_3$, —CH$_2$CH$_2$—OH, or —CF$_3$;
each R$^4$ is independently —H or —(CH$_2$)$_n$NR$^c$R$^d$;
each HetAr is independently a heteroaryl group;
D is CH or N;
Q is —O—, —NR$^a$—, —S(O)$_m$—, or —CHW—;
each k is independently 1, 2, 3 or 4;
each u is independently 1, 2 or 3;
each v is independently 1, 2 or 3;
each p is independently 1 or 2;
each f is independently 0, 1 or 2;
each g is independently 0, 1 or 2;
each h is independently 1 or 2;
each n is independently 0, 1, 2, 3, or 4;
each m is independently 0, 1 or 2;
each of q$_1$ and q$_2$ is independently 0, 1, 2 or 3;
each s is independently 0, 1, 2 or 3; and
each t is independently 0, 1, 2 or 3.

2. The compound of any of the above claim 1, with the proviso that when D is CH, then Q is not —O—; and with the proviso that when D is N and Q is —NR$^a$—, then u and v are not both equal to 1.

3. The compound of claim 1, wherein the compound is a compound of Formula Ib:

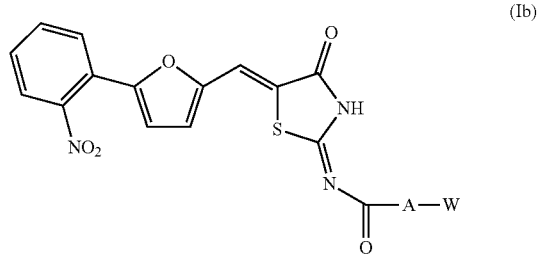

or a pharmaceutically acceptable salt, stereoisomer, or tautomer thereof.

4. The compound any of claim 1, wherein the compound is a compound of Formula II:

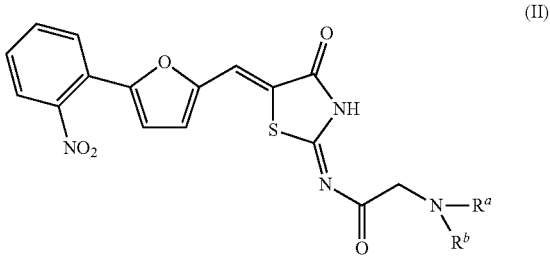

or a pharmaceutically acceptable salt, stereoisomer, or tautomer thereof.

5. The compound of claim 1, wherein the compound is a compound of Formula III:

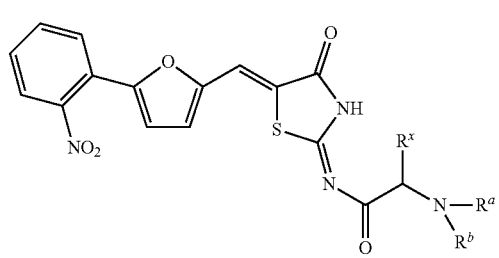

(III)

or a pharmaceutically acceptable salt, stereoisomer, or tautomer thereof.

6. The compound of claim 5, wherein $R^x$ is —CH$_3$, -iPr, —CH$_2$NH$_2$, —CH$_2$CH$_2$NH$_2$, —CH$_2$CH$_2$CH$_2$NH$_2$, —CH$_2$COOH, —CH$_2$CH$_2$COOH,

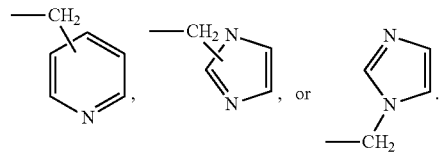

7. The compound of claim 1, wherein the compound is a compound of Formula IV:

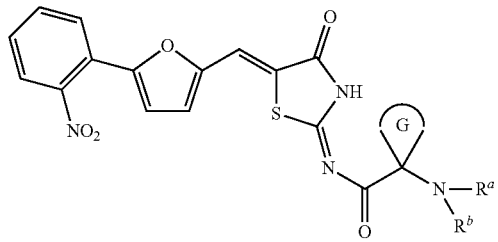

(IV)

or a pharmaceutically acceptable salt, stereoisomer, or tautomer thereof, and wherein ring G is a 5 to 6-membered heterocyclic ring.

8. The compound of claim 7, wherein ring G is

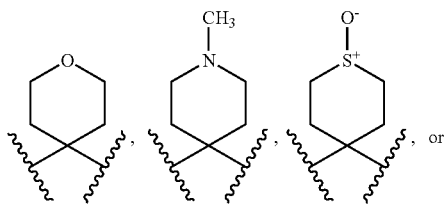

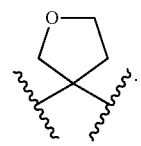

9. The compound of claim 1, wherein the compound is a compound of Formula V:

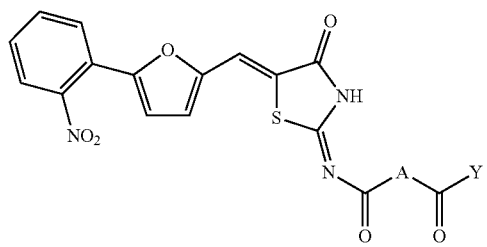

(V)

or a pharmaceutically acceptable salt, stereoisomer, or tautomer thereof, wherein Y is —OR$^4$ or —NR$^a$R$^b$.

10. The compound of any one of claims 1-5, wherein W is —NH$_2$, —NHCH$_3$, N(CH$_3$)$_2$,

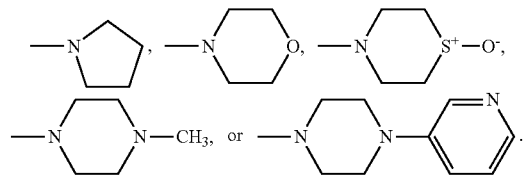

11. The compound of any of claims 1-5, wherein A is —(CH$_2$)$_f$CH(R$^1$)(CH$_2$)$_g$—.
12. The compound of claim 1, wherein W is HetAr.
13. The compound of claim 1, wherein A is

14. The compound of claim 1, wherein A is —(CH$_2$CH$_2$O)$_h$(CH$_2$)$_t$— or —(CH$_2$)$_t$(OCH$_2$CH$_2$)$_h$—.
15. The compound of claim 1, wherein the compound is a compound of Formula VI:

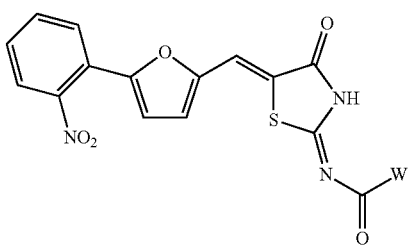

(VI)

or a pharmaceutically acceptable salt, stereoisomer, or tautomer-thereof.

16. The compound of claim 1, wherein A and W combine to form

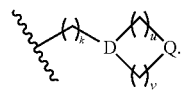

17. The compound of claim 1, wherein the compound is a compound of Formula 8, Formula 12, Formula 16, Formula 20, Formula 22:

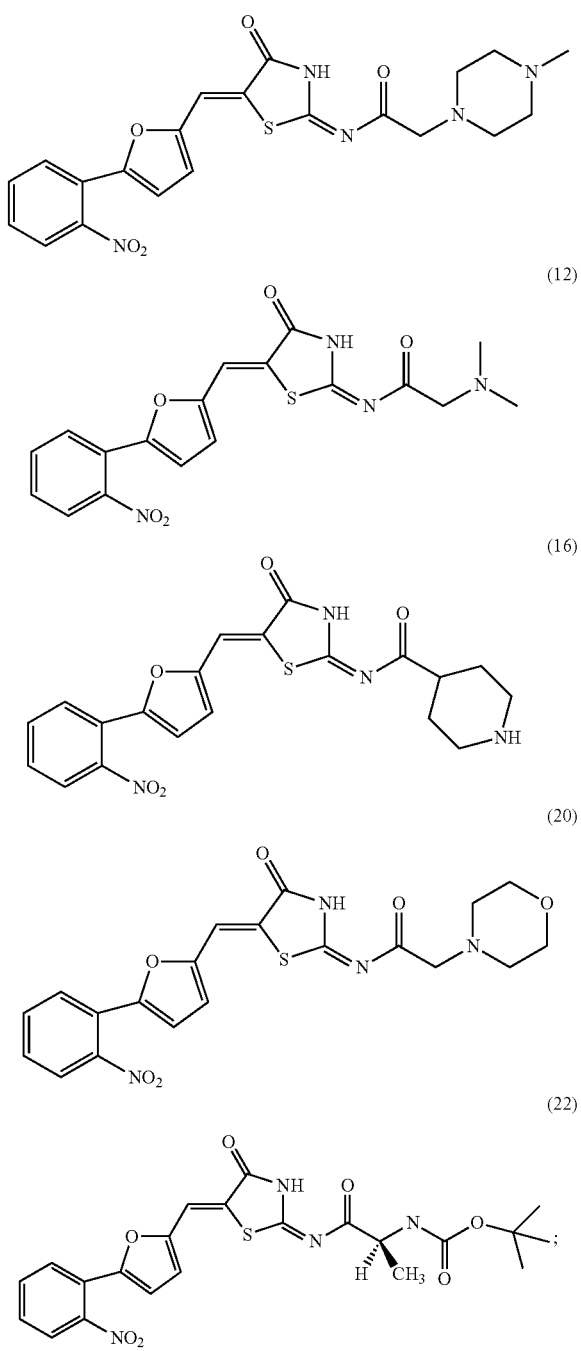

or a pharmaceutically acceptable salt, stereoisomer, or tautomer thereof.

18. The compound of claim 1, wherein the compound is a pharmaceutically acceptable salt.

19. A pharmaceutical composition comprising:
a compound, or a pharmaceutically acceptable salt thereof, in an amount effective for treating or ameliorating a medical condition associated with premature termination codons (PTCs) in RNA, wherein the compound is a compound according to claim 1; and
a pharmaceutically acceptable excipient or pharmaceutically acceptable carrier.

20. A compound according to Formula (9001):

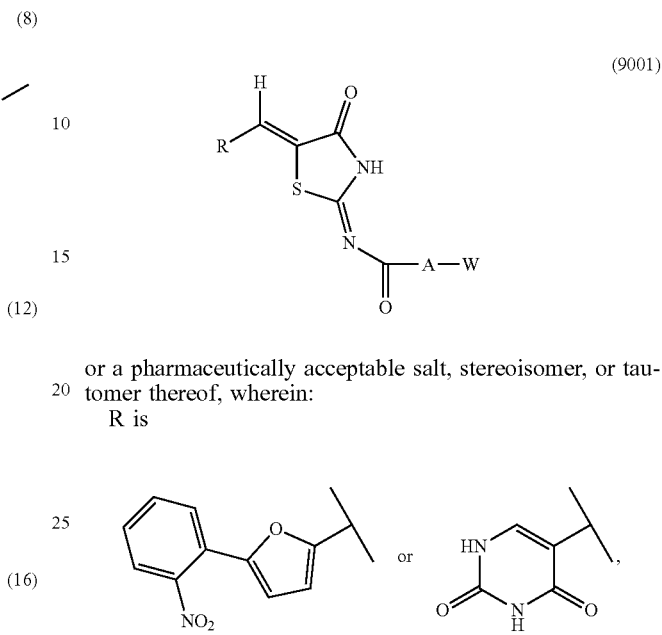

or a pharmaceutically acceptable salt, stereoisomer, or tautomer thereof, wherein:
R is

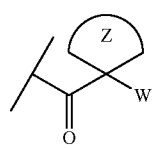

W is —NR$^a$R$^b$, —COOH, -HetAr;
A is A$^1$, A$^2$ or A$^3$;
A$^1$ is —(CH$_2$)$_f$—CH(R$^1$R$^2$)—(CH$_2$)$_g$—;
R$^1$ is —H, —(CH$_2$)$_n$CH$_3$, —CH(CH$_3$)CH$_2$CH$_3$, —CF$_3$, —CH(Ar), —CH(HetAr), —CH$_2$S(O)$_m$CH$_3$, —CH$_2$CH$_2$S(O)$_m$CH$_3$, —CH$_2$(CH$_2$)$_n$—NR$^c$R$^d$, —CH$_2$OH, —CH(CH$_3$)OH, or —(CH$_2$)$_f$—COOH;
R$^c$ is —H, —CH$_3$, —(CH$_2$)$_n$CH$_3$, —CH(R$^2$)CH$_3$, —CH$_2$-pyridyl, or —CH$_2$-Imidazolyl;
R$^d$ is —H, —(CH$_2$)$_n$CH$_3$; or R$^c$ and R$^d$ taken together form a 4-7 membered ring optionally containing O, NR$^e$, or S(O)$_m$;
R$^e$ is —H, —(CH$_2$)$_n$CH$_3$, —CH(CH$_3$)$_2$, —CH(CH$_3$)CH$_2$CH$_3$, —(CH$_2$CH$_2$O)$_p$R$^2$, or —CH$_2$-HetAr;
f is 0-2;
g is 0-2;
n is 0-4;
p is 1-2;
m is 0-2;
R$^2$ is —H, —CH$_3$, —OH, —CF$_3$, or R$^1$ and R$^2$ taken together can form a 4-7 membered ring optionally containing O, NR$^f$, or S(O)$_m$;
R$^f$ is —H, —(CH$_2$)$_n$CH$_3$, —CH(CH$_3$)$_2$, —CH(CH$_3$)CH$_2$CH$_3$, —(CH$_2$CH$_2$O)pR$^2$, a 4-7 member carbocyclic ring, or a 4-7 member heterocyclic ring;
or wherein —C(O)—A—W of Formula 9001 is of Formula 9002:

(9002)

where Z = O, N—R$^e$, S(O)$_{0-2}$ $A^2$ is

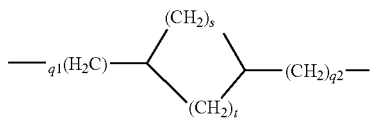
(9003)

q1 and q2 are independently 0-3;
s is 0-3;
t is 1-3;
$A^3$ is —(CH$_2$CH$_2$—O)$_h$—(CH$_2$)$_t$—, —(CH$_2$)$_t$—(O—CH$_2$CH$_2$)$_h$—, —(CH$_2$)$_t$—N(R$^e$)—CH$_2$CH$_2$—Z;
h is 1-2; or
A-W' are taken together as Formula 9004:

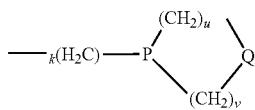
(9004)

wherein P is —CH— or —N—;
Q is —O—, NR$^a$, S(O)$_m$, or —CH—W;
k is 1-4;
u is 1-3;
v is 1-3;

with the proviso that when P is —CH, Q cannot be —O—, and u and v each cannot be 1 when P is —N— and Q is —NR$^a$;

R$^a$ or R$^b$ can independently be R$^e$, or R$^a$ and R$^b$ together with the nitrogen atom to which they are attached, form a 4-7 membered ring which can optionally contain a O, NR$^g$, or S(O)$^m$;

R$^g$ is —H, —(CH$_2$)$_n$CH$_3$, —CH(CH$_3$)$_2$, —CH(CH$_3$)CH$_2$CH$_3$, —(CH$_2$CH$_2$O)$_p$R$^2$, —(CH$_2$)phenyl or —(CH$_2$)phenyl optionally substituted with —F, —Cl, —CH$_3$, —OCH$_3$, —OCF$_3$, or heteroaromatics; and HetAr is pyridyl, pyrimidyl, C-imidazolyl, or N-imidazolyl.

21. A composition, comprising at least one compound or a pharmaceutically acceptable salt or prodrug thereof, wherein the compound is a compound according to claim 20.

22. The composition of claim 21, comprising two compounds, wherein each of the two compounds is according to claim 20.

23. The composition of claim 21, further comprising a pharmaceutically acceptable carrier.

24. The compound of claim 1, wherein each HetAr is independently pyridyl, pyrimidyl, C-imidazolyl or N-imidazolyl.

25. The compound of claim 20, wherein Rf is cyclobutane, cyclopentane, cyclohexane, cycloheptane, oxetane, tetrahydrofurane, dioxane, oxepine, azetidine, pyrrolidine, piperidine, thioxetane, tetrahydrofurane, or a corresponding sulfoxide or sulfone thereof.

* * * * *

UNITED STATES PATENT AND TRADEMARK OFFICE
CERTIFICATE OF CORRECTION

PATENT NO. : 10,077,260 B2
APPLICATION NO. : 15/112100
DATED : September 18, 2018
INVENTOR(S) : Carmen Bertoni et al.

Page 1 of 1

It is certified that error appears in the above-identified patent and that said Letters Patent is hereby corrected as shown below:

In the Claims

In Column 48, Lines 28-31, Claim 2, cancel the text:
"The compound of any of the above claim 1, with the proviso that when D is CH, then Q is not –O–; and with the proviso that when D is N and Q is –$NR^a$–, then u and v are not both equal to 1."

And insert:
--The compound of claim 1, with the proviso that when D is CH, then Q is not –O–; and with the proviso that when D is N and Q is –$NR^a$–, then u and v are not both equal to 1.--

In Column 54, Lines 25-29, Claim 25, cancel the text:
"The compound of claim 20, wherein Rf is cyclobutane, cyclopentane, cyclohexane, cycloheptane, oxetane, tetrahydrofurane, dioxane, oxepine, azetidine, pyrrolidine, piperidine, thioxetane, tetrahydrofurane, or a corresponding sulfoxide or sulfone thereof."

And insert:
--The compound of claim 20, wherein Rf is cyclobutane, cyclopentane, cyclohexane, cycloheptane, oxetane, tetrahydrofurane, dioxane, oxepine, azetidine, pyrrolidine, piperidine, thioxetane, tetrahydrothiofurane, or a corresponding sulfoxide or sulfone thereof.--

Signed and Sealed this
Thirtieth Day of April, 2019

Andrei Iancu
*Director of the United States Patent and Trademark Office*